United States Patent
Courtney et al.

(10) Patent No.: US 10,482,582 B2
(45) Date of Patent: Nov. 19, 2019

(54) SYSTEMS AND METHODS FOR NOISE REDUCTION IN IMAGING

(71) Applicant: SUNNYBROOK RESEARCH INSTITUTE, Toronto (CA)

(72) Inventors: Brian Courtney, Toronto (CA); Naimul Mefraz Khan, Toronto (CA); Natasha Alves-Kotzev, Thornhill (CA)

(73) Assignee: SUNNYBROOK RESEARCH INSTITUTE, Toronto, ON (CA)

( * ) Notice: Subject to any disclaimer, the term of this patent is extended or adjusted under 35 U.S.C. 154(b) by 135 days.

(21) Appl. No.: 15/904,134

(22) Filed: Feb. 23, 2018

(65) Prior Publication Data

US 2018/0253830 A1 Sep. 6, 2018

Related U.S. Application Data

(60) Provisional application No. 62/463,431, filed on Feb. 24, 2017.

(51) Int. Cl.
| | |
|---|---|
| *G06T 5/00* | (2006.01) |
| *G06T 5/10* | (2006.01) |
| *G01R 33/56* | (2006.01) |
| *A61B 5/00* | (2006.01) |

(52) U.S. Cl.
CPC .......... *G06T 5/002* (2013.01); *G01R 33/5608* (2013.01); *G06T 5/10* (2013.01); *A61B 5/7203* (2013.01); *G06T 2207/10088* (2013.01); *G06T 2207/10132* (2013.01)

(58) Field of Classification Search
CPC .. G06T 5/00; G06T 5/002; G06T 5/50; G06T 5/10; G06T 2207/10088–10096; G06T 2207/10132–10136; G01R 33/5608; A61B 5/7203
See application file for complete search history.

(56) References Cited

U.S. PATENT DOCUMENTS

| | | |
|---|---|---|
| 6,678,209 B1 | 1/2004 | Peng et al. |
| 6,814,701 B1 | 11/2004 | Tamura |
| 7,421,377 B2 | 9/2008 | Zhang |

(Continued)

OTHER PUBLICATIONS

Van Moer et al., Instrumentation and Measurement Technology Conference (I2MTC), 2013 IEEE International, 2013; DOI: 10.1109/I2MTC.2013.6555393.

(Continued)

*Primary Examiner* — Sean T Motsinger
(74) *Attorney, Agent, or Firm* — Hill & Schumacher

(57) ABSTRACT

Systems and methods are provided for the denoising of images in the presence of broadband noise based on the detection and/or estimation of in-band noise. According to various example embodiments, an estimate of broadband noise that lies within the imaging band is made by detecting or characterizing the out-of-band noise that lies outside of the imaging band. This estimated in-band noise may be employed for denoise the detected imaging waveform. According to other example embodiments, a reference receive circuit that is sensitive to noise within the imaging band, but is isolated from the imaging energy, may be employed to detect and/or characterize the noise within the imaging band. The estimated reference noise may be employed to denoise the detected in-band imaging waveform.

22 Claims, 28 Drawing Sheets

(56) References Cited

U.S. PATENT DOCUMENTS

| | | | |
|---|---|---|---|
| 7,513,873 B2 | 4/2009 | Shifrin | |
| 7,593,815 B2 | 9/2009 | Willen et al. | |
| 7,611,467 B2 | 11/2009 | Zhang | |
| 7,933,741 B2 | 4/2011 | Willen et al. | |
| 7,946,990 B2 | 5/2011 | Srinivasan et al. | |
| 8,232,799 B2 | 7/2012 | Hajian et al. | |
| 8,326,621 B2 | 12/2012 | Hetherington et al. | |
| 8,660,226 B2 | 2/2014 | Narayanan et al. | |
| 8,666,092 B2 | 3/2014 | Zavarehei | |
| 9,786,056 B2* | 10/2017 | Courtney | G06T 15/08 |
| 2007/0016045 A1 | 1/2007 | Zhang | |
| 2007/0189635 A1 | 8/2007 | Borsdorf | |
| 2008/0239094 A1* | 10/2008 | Baqai | H04N 1/00 348/223.1 |
| 2008/0309424 A1* | 12/2008 | Shen | H03B 5/366 331/158 |
| 2009/0136104 A1 | 5/2009 | Hajian et al. | |
| 2013/0322753 A1* | 12/2013 | Lim | G06T 5/001 382/167 |
| 2013/0329981 A1* | 12/2013 | Hiroike | G06T 7/0012 382/132 |
| 2014/0140634 A1* | 5/2014 | Hayashida | H04N 5/32 382/264 |
| 2014/0219422 A1* | 8/2014 | Nishino | G06T 11/005 378/62 |
| 2014/0270563 A1* | 9/2014 | Bailey | G06T 5/005 382/254 |
| 2014/0314333 A1* | 10/2014 | Takahashi | A61B 6/5258 382/264 |
| 2015/0296193 A1* | 10/2015 | Cote | H04N 9/646 382/167 |
| 2016/0180541 A1* | 6/2016 | Romanenko | G06K 9/0051 382/103 |
| 2016/0182841 A1* | 6/2016 | Iwasaki | H04N 5/217 348/362 |
| 2016/0331340 A1* | 11/2016 | Mako | A61B 6/5258 |
| 2016/0358330 A1* | 12/2016 | Asai | A61B 6/52 |
| 2016/0366352 A1* | 12/2016 | Kobayashi | G06T 5/40 |
| 2016/0366353 A1* | 12/2016 | Kobayashi | H04N 5/361 |
| 2017/0270643 A1* | 9/2017 | Baek | G06T 5/002 |
| 2018/0253830 A1* | 9/2018 | Courtney | G06T 5/002 |

OTHER PUBLICATIONS

Gonzales-Fuentes, Lee, Kurt Barbe, and Wendy Van Moer. "Adaptive noise tracking for Cognitive Radios under more realistic operation conditions." Instrumentation and Measurement Technology Conference (I2MTC) Proceedings, 2014 IEEE International. IEEE, 2014.

International Search Report for the corresponding PCT application CA2018/050212, dated May 11, 2018.

* cited by examiner

| | Classification of windows before neighborhood consideration | | | | | | | | | |
|---|---|---|---|---|---|---|---|---|---|---|
| Arr \Win | 1 | 2 | 3 | 4 | 5 | 6 | 7 | 8 | 9 | 10 |
| Array1 | S | S | S | S | S | S | S | S | S | S |
| Array2 | N | S | S | N | N | S | S | S | N | S |
| Array3 | N | S | S | S | S | S | S | N | N | S |
| Array4 | S | S | S | S | S | S | S | S | N | S |
| Array5 | S | N | N | S | N | N | S | S | S | S |

FIG. 6E

| | Classification of windows after neighborhood consideration | | | | | | | | | |
|---|---|---|---|---|---|---|---|---|---|---|
| Arr \Win | 1 | 2 | 3 | 4 | 5 | 6 | 7 | 8 | 9 | 10 |
| Array1 | S | S | S | S | S | S | S | S | S | S |
| Array2 | N | S | S | replace | replace | S | S | S | N | S |
| Array3 | N | S | S | S | S | S | S | N | N | S |
| Array4 | S | S | S | S | S | S | S | S | N | S |
| Array5 | S | N | N | N | N | N | S | S | S | S |

FIG. 6F

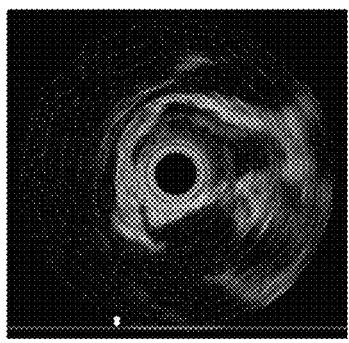 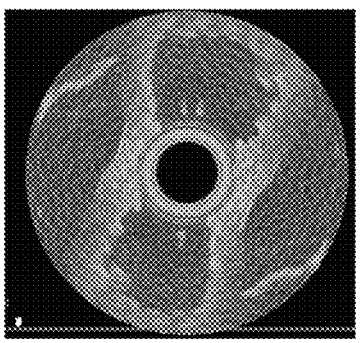 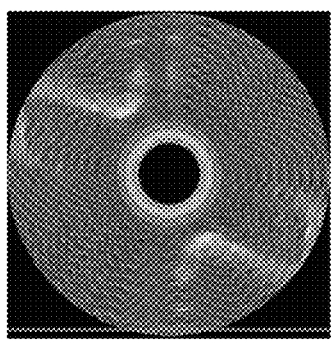
FIG. 10A    FIG. 10B    FIG. 10C
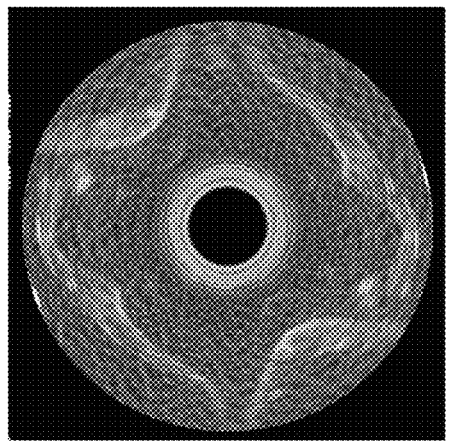 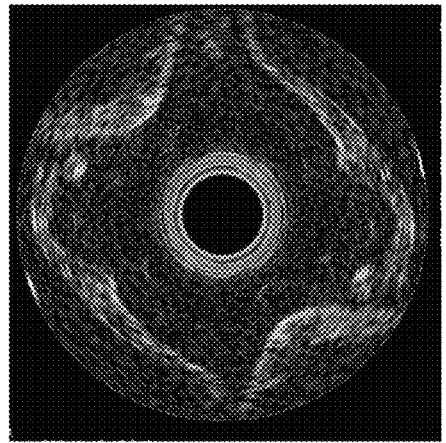
FIG. 11A    FIG. 11B

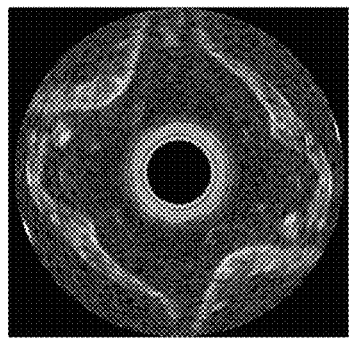 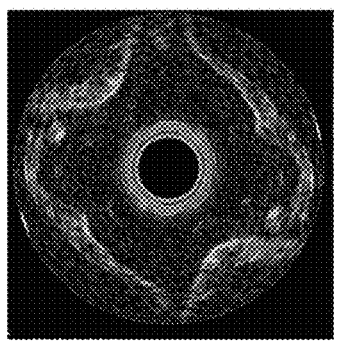 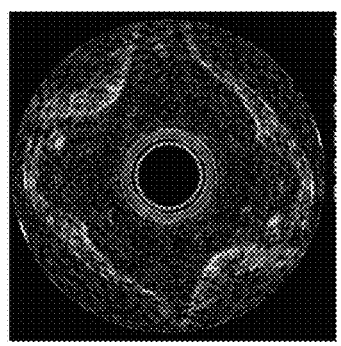
FIG. 11C      FIG. 11D      FIG. 11E
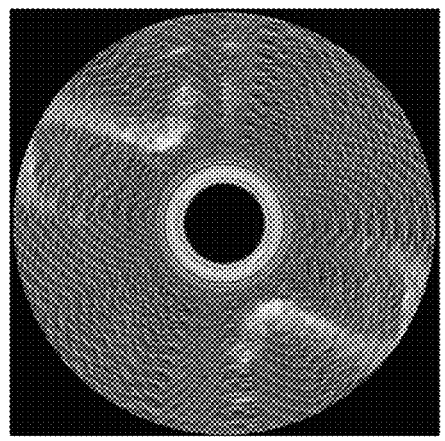 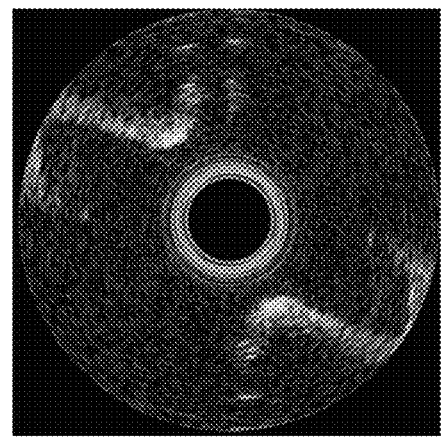
FIG. 12A      FIG. 12B

|  | Imaging transducer Receive Channel | | Reference Receive Channel |
| --- | --- | --- | --- |
|  | | Noise-Detection Waveform | |
|  | Imaging band | Noise-Detection band | |
|  | | detection-band waveform | |
|  | "in-band" | "out-of-band" | "within-band" | |
| Imaging Mode | | Noise-detection imaging waveform | |
| | in-band imaging waveform | detection-band imaging waveform | | reference noise-detection waveform |
| | | out-of-band noise-detection imaging waveform | (optional) within-band noise-detection imaging waveform | |
| Characterization mode | | Noise-Characterization waveforms | |
| | in-band noise-characterization waveform | detection-band noise-characterization waveform | | reference noise-characterization waveform |
| | | out-of-band noise-characterization waveform | (optional) within-band noise-characterization waveform | |
| | in-band baseline noise characterization waveform | detection-band baseline noise characterization waveform | | |

FIG. 14

SYSTEMS AND METHODS FOR NOISE REDUCTION IN IMAGING

CROSS-REFERENCE TO RELATED APPLICATION

This application claims priority to U.S. Provisional Application No. 62/463,431, titled "SYSTEMS AND METHODS FOR NOISE REDUCTION IN IMAGING" and filed on Feb. 24, 2017, the entire contents of which is incorporated herein by reference.

BACKGROUND

The present disclosure relates to imaging technologies and the processing of imaging data for the removal of noise.

Medical imaging with ultrasound and MRI imaging relies on detecting low amplitude signals in the radiofrequency spectrum, typically spanning from 2 MHz to 200 MHz. Image quality is greatly influenced by the signal-to-noise ratio. In intravascular ultrasound (IVUS), intracardiac echocardiography (ICE) and other forms of minimally invasive ultrasound, the ultrasound transducer detects ultrasound signals from the surrounding structures and converts the acoustic energy into an electrical signal. This signal is then transmitted along one or more conductive channels (such as coaxial conductors, twisted pair conductors, flex circuits etc.). For many reasons, (including cost, manufacturability, safety, biocompatibility, thermal concerns, and requirements for provision of power) the portion of the minimally invasive imaging probe that can be inserted intracorporeally often does not contain an amplifier to boost the signal strength. The electrical signals detected by minimally invasive ultrasound transducers can be very small (<10 mV and more typically <1 mv), and much of the information about tissue structures that can be imaged with ultrasound tends to lie in the lower portion of the dynamic range of the electrical signals that are detected. The signal amplitude of a received ultrasound signal is limited by any or all of the mechanical efficiency of the transducer, the low amplitude of the acoustic signals detected, the small size of the transducer and attenuation along the conductors that carry the electrical signal from the transducer out of the body. In light of this, the signals in minimally invasive ultrasound imaging systems tend to be very weak.

Noise can be introduced into the system from many sources, including radio transmitters, power electronics, transmission lines, switching transistors and others known in the art. Noise can be introduced via induction or directly via conduction and suboptimal isolation of components that are sensitive to electromagnetic interference. Some of the noise may be generated by components within the imaging system itself, such as scanning actuators, pulse width modulators for motor controllers, switched mode power supplies, clocking circuits and transistors in any of the electronic components of an imaging system. Furthermore, other systems coupled to a patient or in the procedural environment, such as impedance monitors, tracking systems (like those found in Carto® 3, Carto® XP or NavX™ systems), temperature sensors, infusion pumps, ablation systems, ECG and hemodynamic monitors can introduce noise. RFID inventory control systems used in some clinical areas can also introduce noise.

Several approaches are directed at reducing the amount of noise that enters into the ultrasound receive circuitry of ultrasound imaging systems, including selection of components within the system that generate minimal RF noise, electrical isolation, shielding, proper grounding, and physically separating noise-generating components from components that are susceptible to electromagnetic noise. These approaches are often difficult to implement, as the sources of the noise often have preferred characteristics for other reasons (i.e. pulse width modulated motor controllers are energy efficient and have good response times) or are difficult to physically isolate from one another (i.e. it may be desirable to have power electronics in close proximity to the imaging probe or its associated circuitry).

Other approaches for reducing the effect of noise on ultrasound signal quality (and hence ultrasound image quality) include filtering and image processing. Ultrasound signals typically have a known bandwidth and the detected ultrasound signal may be filtered using either analog or digital filtering techniques (often a combination of the two). Analog or digital filtering can be applied to limit the portions of the electrical signal output from the ultrasound receive circuitry to those portions whose frequencies lie within the operational bandwidth (or harmonics thereof) of the ultrasound transducer. Selecting filters with narrow bandwidths and sharp cutoffs can reduce the amount of noise that is allowed into the signals used to generate images or otherwise make use of the ultrasound signals (such as for Doppler measurements spectral analysis of the ultrasound signal, or assessment of flow of scatterers in the sonicated field). Notch or comb filters are helpful in removing narrowband noise within the imaging range of frequencies. Overly aggressive filtering can have the unwanted effect of reducing the amount of signal power that gets accepted for generating images or for other use of the ultrasound signals. It may also negatively impact other performance aspects of an ultrasound imaging system, such as resolution. However, if the passband of the filters is too large, then more noise is accepted into the system.

Image processing can further reduce the noise by filtering the image data generated, such as by averaging or removing outlier values. For example, such filtering can be applied within the image in the spatial domain by applying a Gaussian filter to a pixel and its neighboring pixels in order to blur or smoothen out any random noise in the image. Unfortunately, this tends to reduce the spatial resolution of the image. Similarly, spatial domain filtering can be applied in the structures being imaged that do not move rapidly with respect to the frame repetition frequency of the imaging modality. For example, a pixel in an image frame can be the average or Gaussian-filtered result of the pixels at similar positions in one or more preceding and/or trailing frames.

Similar problems apply to MRI imaging systems, where weak signals are detected in the presence of noise from undesired sources of radiofrequency energy.

What would be very helpful are methods, systems and devices to identify noise and actively remove the noise from one or more imaging signals.

Many forms of noise enter into the ultrasound receive signal chain and can become difficult to remove once they enter the system, especially if they are broadband in nature, wherein a portion of the noise lies within the passband of the ultrasound system. For example, in an imaging system that has a transducer with a center frequency of 10 MHz, and a passband of 7.5 to 12.5 MHz, the system may be designed to heavily filter out any portions of the noise that are less than 7.5 MHz and any portions of the noise that are more than 12.5 MHz. Unfortunately, the amplitude of the noise within the 7.5-12.5 MHz bandpass may frequently be appreciable relative to the amplitude of the ultrasound signal that is being detected.

Many sources of noise occur as a result of rapid transients, such as when a field effect transistor or switch turns on or off. An electrical signal with rapid transients in it has a very broad frequency domain representation that can easily span all or a portion of the passband of the ultrasound receive signal chain. This is particularly true of power supplies or pulse width modulation circuits where the noise can have a strong enough amplitude to compete with the signal being detected.

SUMMARY

One approach to reduce broadband noise exploits the fact that imaging energy predominantly lies within a selective imaging band but that broadband noise can be detected both within the imaging band and outside of the imaging band. In principle, by detecting or characterizing noise outside of the imaging band at any point in time, one can estimate the broadband noise that might lie within the imaging band and alter the detected signal to reduce the estimated in-band noise. By effectively creating an estimate of the in-band noise based on out-of-band noise, one can generate a signal that estimates the desired imaging energy in the absence of the estimated in-band noise.

Another approach to reduce noise within the imaging band is to use reference receive circuits (comprising resistors, capacitors, inductors, transmission lines, amplifiers, transformers, inactivated transducers or components that can emulate a transducer receive circuit) that are sensitive to noise in the imaging band, but are isolated from the imaging energy. By estimating the in-band imaging noise based on in-band noise received by the reference receive circuit, one can generate signals that estimate the desired imaging energy in the absence of the estimated in-band noise.

In one aspect, there is provided a method of denoising imaging signals detected in the presence of broadband noise, the method comprising:

in the absence of receiving imaging energy, detecting energy waves with an imaging transducer receive circuit, thereby obtaining a noise characterization waveform, and filtering the noise characterization waveform to generate an in-band noise characterization waveform residing within an imaging band and an out-of-band noise characterization waveform residing within a noise-detection band that lies, at least in part, beyond the imaging band;

segmenting the in-band noise characterization waveform and the out-of-band noise characterization waveform according to one or more time windows;

for at least one time window, processing the in-band noise characterization waveform and the out-of-band noise characterization waveform to determine a relationship between noise in the imaging band and noise in the noise-detection band;

detecting imaging signals with the imaging transducer receive circuit thereby obtaining one or more imaging waveforms;

for at least one imaging waveform:
a) filtering the imaging waveform to generate an in-band imaging waveform residing within the imaging band and an out-of-band noise-detection imaging waveform residing within the noise-detection band;
b) segmenting the in-band imaging waveform and the out-of-band noise-detection imaging waveform according to one or more time windows;
c) employing the relationship and the out-of-band noise-detection imaging waveform to estimate, within at least one time window, a measure associated with the amount of noise in the in-band imaging waveform; and
d) for at least one time window processed in c), applying a denoising correction to the portion of the in-band imaging waveform within the time window.

In another aspect, there is provided a method of denoising imaging signals detected in the presence of noise, the method comprising:

in the absence of receiving imaging energy:
detecting energy waves with an imaging transducer receive circuit, thereby obtaining a noise characterization waveform, and filtering the noise characterization waveform to generate an in-band noise characterization waveform residing within an imaging band; and
detecting noise with a reference receive circuit configured to avoid transduction of imaging energy while detecting noise received by the imaging transducer receive circuit, thereby obtaining a reference noise characterization waveform;

processing the in-band noise characterization waveform and the reference noise characterization waveform to determine a relationship between noise in the imaging band and noise detected by the reference receive circuit;

detecting imaging signals with the imaging transducer receive circuit, thereby obtaining one or more imaging waveforms;

for at least one imaging waveform:
a) filtering the imaging waveform to generate an in-band imaging waveform residing within the imaging band;
b) detecting, with the reference receive circuit, a reference noise-detection waveform;
c) segmenting the in-band imaging waveform and the reference noise-detection waveform according to one or more time windows;
d) employing the relationship and the reference noise-detection waveform to estimate, within at least one time window, a measure associated with the amount of noise in the in-band imaging waveform; and
e) for at least one time window processed in c), applying a denoising correction to the portion of the in-band imaging waveform within the time window.

In another aspect, there is provided a method of denoising imaging signals detected in the presence of broadband noise, the method comprising:

detecting energy waves with an imaging transducer receive circuit, thereby obtaining an imaging waveform, and filtering the imaging waveform to generate an in-band imaging waveform residing within an imaging band and an out-of-band noise-detection imaging waveform residing within a noise-detection band that lies, at least in part, beyond the imaging band;

detecting an in-band imaging envelope of the in-band imaging waveform;

detecting an out-of-band envelope of the out-of-band noise-detection imaging waveform;

applying a scaling factor to the out-of-band envelope, thereby obtaining a modified out-of-band envelope; and combining the modified out-of-band envelope and the in-band imaging envelope to obtain a noise-corrected in-band envelope;

wherein the scaling factor is selected to reduce a contribution of in-band noise in the noise-corrected in-band envelope.

In another aspect, there is provided a method of denoising imaging signals detected in the presence of noise, the method comprising:

detecting energy waves with an imaging transducer receive circuit, thereby obtaining an imaging waveform, and filtering the imaging waveform to generate an in-band imaging waveform residing within an imaging band and an out-of-band noise-detection imaging waveform residing within a noise-detection band that lies, at least in part, beyond the imaging band;

applying a frequency shift and an amplitude scaling factor to the out-of-band noise-detection imaging waveform, thereby obtaining a modified waveform, such that the modified waveform includes frequency components residing within the imaging band; and combining the modified waveform and the in-band imaging waveform to obtain a noise-corrected in-band imaging waveform;

wherein the amplitude scaling factor is selected to reduce a contribution of in-band noise in the noise-corrected in-band imaging waveform.

In another aspect, there is provided a method of denoising imaging signals detected in the presence of noise, the method comprising:

detecting energy waves with an imaging transducer receive circuit, thereby obtaining an imaging waveform, and filtering the imaging waveform to generate an in-band imaging waveform residing within an imaging band; and detecting noise with a reference receive circuit configured to avoid transduction of imaging energy while detecting noise received by the imaging transducer receive circuit, thereby obtaining a reference noise-detection waveform;

detecting an in-band imaging envelope of the in-band imaging waveform;

detecting a reference envelope of the reference noise-detection waveform;

applying a scaling factor to the reference envelope, thereby obtaining a modified reference envelope; and combining the modified reference envelope and the in-band imaging envelope to obtain a noise-corrected in-band envelope;

wherein the scaling factor is selected to reduce a contribution of in-band noise in the noise-corrected in-band envelope.

In another aspect, there is provided a method of denoising imaging signals detected in the presence of noise, the method comprising:

detecting energy waves with an imaging transducer receive circuit, thereby obtaining an imaging waveform, and filtering the imaging waveform to generate an in-band imaging waveform residing within an imaging band; and detecting noise with a reference receive circuit configured to avoid transduction of imaging energy while detecting noise received by the imaging transducer receive circuit, thereby obtaining a reference noise-detection waveform;

adaptively filtering the reference noise-detection waveform according to one or more adaptive filter parameters; and combining the filtered reference noise-detection waveform and the in-band imaging waveform to obtain a noise-corrected in-band imaging waveform;

wherein the adaptive filter parameters are actively determined by processing the noise-corrected in-band imaging waveform to minimize the power of the noise-corrected in-band imaging waveform.

In another aspect, there is provided a method of denoising imaging signals detected in the presence of broadband noise, the method comprising:

detecting energy waves with an imaging transducer receive circuit, thereby obtaining an imaging waveform, and filtering the imaging waveform to generate an in-band imaging waveform residing within an imaging band and an out-of-band noise-detection imaging waveform residing within a noise-detection band that lies, at least in part, beyond the imaging band;

detecting an in-band imaging envelope of the in-band imaging waveform;

detecting an out-of-band imaging envelope of the out-of-band noise-detection imaging waveform;

adaptively filtering the out-of-band imaging envelope according to one or more adaptive filter parameters; and combining the filtered out-of-band imaging envelope and the in-band imaging envelope to obtain a noise-corrected in-band imaging envelope;

wherein the adaptive filter parameters are actively determined by processing the noise-corrected in-band imaging envelope to minimize the power of the noise-corrected in-band imaging envelope.

In another aspect, there is provided a method of denoising imaging signals detected in the presence of broadband noise, the method comprising:

detecting energy waves with an imaging transducer receive circuit, thereby obtaining an imaging waveform, and filtering the imaging waveform to generate an in-band imaging waveform residing within an imaging band and an out-of-band noise-detection imaging waveform residing within a noise-detection band that lies, at least in part, beyond the imaging band;

applying a frequency shift to the out-of-band noise-detection imaging waveform, thereby obtaining a modified waveform, such that the modified waveform includes frequency components residing within the imaging band;

adaptively filtering the out-of-band noise-detection imaging waveform according to one or more adaptive filter parameters; and combining the filtered modified waveform and the in-band imaging waveform to obtain a noise-corrected in-band imaging waveform;

wherein the adaptive filter parameters are actively determined by processing the noise-corrected in-band imaging waveform to minimize the power of the noise-corrected in-band imaging waveform.

In another aspect, there is provided a method of denoising imaging signals detected in the presence of broadband noise, the method comprising:

detecting energy waves with an imaging transducer receive circuit, thereby obtaining an imaging waveform, and filtering the imaging waveform to generate an in-band imaging waveform residing within an imaging band and an out-of-band noise-detection imaging waveform residing within a noise-detection band that lies, at least in part, beyond the imaging band;

processing the out-of-band noise-detection imaging waveform to select suitable filter parameters of a dynamic digital filter for filtering the in-band imaging waveform to remove in-band noise; and filtering the in-band imaging waveform with the dynamic digital filter according to the filter parameters.

In another aspect, there is provided a method of performing noise reduction on signals obtained by a detection system characterized by one or more noise sources, comprising:

in the absence of receiving imaging energy, detecting energy waves with an imaging transducer receive circuit, thereby obtaining a noise characterization waveform, and filtering the noise characterization waveform to generate an in-band noise characterization waveform residing within an imaging band and an out-of-band noise characterization waveform residing within a noise-detection band that lies, at least in part, beyond the imaging band;

segmenting the in-band noise characterization waveform and the out-of-band noise characterization waveform according to one or more time windows;

for at least one time window, processing the in-band noise characterization waveform and the out-of-band noise characterization waveform according to a pattern recognition algorithm to identify a noise pattern within the noise-detection band that is correlated with noise in the imaging band;

detecting imaging signals with the imaging transducer receive circuit, thereby obtaining an imaging waveform and filtering the imaging waveform to obtain an in-band imaging waveform residing within the imaging band and an out-of-band noise-detection imaging waveform residing within the noise-detection band;

segmenting the in-band imaging waveform and the out-of-band imaging waveform according to one or more time windows;

for at least one time window, processing the out-of-band noise-detection imaging waveform according to the pattern recognition algorithm to detect of the noise pattern; and in the event of detection of the noise pattern, applying a denoising correction to the time window of the in-band imaging waveform that is specific to the noise pattern detected in the out-of-band noise-detection imaging waveform.

In another aspect, there is provided a method of performing noise reduction on signals obtained by a detection system characterized by one or more known noise sources, comprising:

in the absence of receiving imaging energy:
  detecting energy waves with an imaging transducer, thereby obtaining a noise characterization waveform, and filtering the noise characterization waveform to generate an in-band noise characterization waveform residing within an imaging band; and
  detecting noise with a reference receive circuit configured to avoid transduction of imaging energy while detecting noise received by the imaging transducer receive circuit, thereby obtaining a reference noise characterization waveform;
  segmenting the in-band noise characterization waveform and the reference noise characterization waveform according to one or more time windows;
  for at least one time window, processing the in-band noise characterization waveform and the reference noise characterization waveform to determine a relationship between noise in the imaging band and noise detected by the reference receive circuit;

processing the in-band noise characterization waveform and the reference noise characterization waveform according to a pattern recognition algorithm to identify the presence of a noise pattern within the reference noise characterization waveform that is correlated with noise in the in-band noise characterization waveform;

detecting imaging signals with the imaging transducer receive circuit to obtain an imaging waveform, while also detecting a reference noise-detection waveform with the reference receive circuit, and filtering the imaging waveform to obtain an in-band imaging waveform residing within the imaging band;

segmenting the in-band imaging waveform and the reference noise-detection waveform according to one or more time windows;

for at least one time window, processing the reference noise-detection waveform according to the pattern recognition algorithm to detect the presence of the noise pattern; and in the event of detection of the noise pattern, applying a denoising correction to the time window of the in-band imaging waveform that is specific to the noise pattern detected in the reference noise-detection waveform.

In another aspect, there is provided a method of denoising imaging signals detected in the presence of noise, the method comprising:

in the absence of receiving imaging energy, detecting energy waves with an imaging transducer receive circuit, thereby obtaining a noise characterization waveform, and filtering the noise characterization waveform to generate an in-band noise characterization waveform residing within an imaging band and an out-of-band noise characterization waveform residing within a noise-detection band that lies, at least in part, beyond the imaging band;

detecting imaging signals with the imaging transducer receive circuit, thereby obtaining an imaging waveform, and filtering the imaging waveform to generate an in-band imaging waveform residing within the imaging band and an out-of-band noise-detection imaging waveform residing within the noise-detection band;

performing a cross-correlation between the out-of-band imaging waveform and the out-of-band noise characterization waveform to determine a time delay associated with a maximum cross-correlation; and applying the time delay and an amplitude adjustment to the in-band noise characterization waveform, thereby obtaining a modified in-band noise characterization waveform, and subtracting the modified in-band noise characterization waveform from the in-band imaging waveform.

In another aspect, there is provided a method of denoising imaging signals detected in the presence of noise, the method comprising:

in the absence of receiving imaging energy:
  detecting energy waves with an imaging transducer receive circuit, thereby obtaining a noise characterization waveform, and filtering the noise characterization waveform to generate an in-band noise characterization waveform residing within an imaging band; and
  detecting noise with a reference receive circuit configured to avoid transduction of imaging energy while detecting noise received by the imaging transducer receive circuit, thereby obtaining a reference noise characterization waveform;

detecting imaging signals with the imaging transducer receive circuit to obtain an imaging waveform, while also detecting a reference noise-detection waveform with the reference receive circuit, and filtering the imaging waveform to obtain an in-band imaging waveform residing within the imaging band;

performing a cross-correlation between the reference noise-detection waveform and the reference noise characterization waveform to determine a time delay associated with a maximum cross-correlation; and applying the time delay and an amplitude adjustment to the in-band noise characterization waveform, thereby obtaining a modified in-band noise characterization waveform, and subtracting the modified in-band noise characterization waveform from the in-band imaging waveform.

In another aspect, there is provided a method of denoising imaging signals detected in the presence of noise, the method comprising:

detecting imaging signals with an imaging transducer receive circuit along a plurality of adjacent scan lines, thereby obtaining a plurality of imaging waveforms;

for at least two adjacent scan lines:
filtering the imaging waveform respectively associated therewith to generate an in-band imaging waveform residing within an imaging band and an out-of-band noise-detection imaging waveform residing within a noise-detection band that lies, at least in part, beyond the imaging band;
segmenting the in-band imaging waveform and the out-of-band noise-detection imaging waveform according to a series of time windows;
for at least one window:
processing the out-of-band noise-detection imaging waveform to determine whether or not a corresponding windowed portion of the in-band imaging waveform should be noise corrected; and
in the event that the in-band imaging waveform within the time window is deemed to be suitable for noise correction, applying a denoising correction to the in-band imaging waveform within the time window, wherein the denoising correction for each sample in the window is based on one or more statistical measures associated with samples in the in-band imaging waveforms from two or more adjacent windows, each adjacent window residing in a respective adjacent scan line; and
generating an image based on denoised in-band imaging waveforms respectively associated with the plurality of scan lines.

In another aspect, there is provided a method of denoising imaging signals detected in the presence of noise, the method comprising:
detecting energy waves with an imaging transducer receive circuit, thereby obtaining an imaging waveform, and filtering the imaging waveform to generate an in-band imaging waveform residing within an imaging band and an out-of-band noise-detection imaging waveform residing within a noise-detection band that lies, at least in part, beyond the imaging band;
detecting imaging signals with an imaging transducer receive circuit along a plurality of adjacent scan lines, thereby obtaining a plurality of imaging waveforms;
processing one or more out-of-band noise-detection imaging waveforms to determine the periodicity of a noise source,
adjusting the scan rate such that the noise is not temporally synchronized in in-band imaging waveforms associated with adjacent scan lines.
for at least two adjacent scan lines:
segmenting the in-band imaging waveform according to a series of time windows;
for at least one window:
applying a denoising correction to the in-band imaging waveform within the time window, wherein the denoising correction for each sample in the window is based on one or more statistical measures associated with samples in the in-band imaging waveforms from two or more adjacent windows, each adjacent window residing in a respective adjacent scan line; and
generating an image based on denoised in-band imaging waveforms respectively associated with the plurality of scan lines.

In another aspect, there is provided a method of denoising imaging signals detected in the presence of noise, the method comprising:
for at least two adjacent scan lines:
detecting imaging signals with an imaging transducer receive circuit to obtain an imaging waveform, while also detecting a reference noise-detection waveform with the reference receive circuit, and filtering the imaging waveform to obtain an in-band imaging waveform residing within the imaging band;
segmenting the in-band imaging waveform and the reference noise-detection waveform according to a series of time windows;
for at least one window:
processing the reference noise-detection waveform to determine whether or not a corresponding windowed portion of the in-band imaging waveform should be noise corrected; and
in the event that the in-band imaging waveform within the time window is deemed to be suitable for noise correction, applying a denoising correction to the in-band imaging waveform within the time window, wherein the denoising correction for each sample in the window is based on one or more statistical measures associated with samples in the in-band imaging waveforms from two or more adjacent windows, each adjacent window residing in a respective adjacent scan line; and
generating an image based on denoised in-band imaging waveforms respectively associated with the plurality of scan lines.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 2A illustrates an example system configuration for noise reduction on the envelope of an input waveform via the estimation and suppression of the estimated in-band noise, where the in-band noise is estimated by performing envelope detection of an out-of-band waveform, followed by delay, scale and shape adjustment prior to subtraction.

FIGS. 6E and 6F show charts pertaining to a method in which different time windows of an in-band waveform are initially identified as being predominantly signal or noise, after which noise windows surrounded by signal windows are identified as being likely erroneous and are reclassified, and conversely after which signal windows surrounded by noise windows are identified as being erroneous and are reclassified as noise.

FIGS. 10A-C show example images obtained using an intra-cardiac echo system showing (A) an image obtained in the absence of a noise source; (B) an image obtained in the presence of noise generated via an electroanatomic mapping system; and (C) an image obtained in the presence of noise generated from an ablation generator.

FIGS. 11A-B show images obtained in the presence of noise from an electroanatomic mapping system, without (A) and with (B) noise reduction.

FIGS. 11C-E show images obtained in the presence of noise from an electroanatomic mapping system after noise reduction by attenuation, where the relaxation parameter was set as 0.5 (C), 1 (D) and 1.5 (E).

FIGS. 12A-B show images obtained in the presence of noise from an ablation generator, without (A) and with (B) the application of a noise reduction method.

FIG. 14 shows the phrases used to refer to waveforms in the imaging band, noise detection band and waveforms from a reference receive circuit

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Ultrasound imaging relies on receiving echoes from a medium, optionally after sending a narrow acoustic pulse out in the medium in a particular direction. As used herein, the term "scan line" refers to a line representing a spatial direction in the medium from which imaging energy is to be received. A 2D image is obtained by receiving echoes from a plurality of scan lines within the medium. The present inventors have conceived, developed and tested various methods and systems that effectively reduce broadband noise from an ultrasound acquisition and/or processing system.

Figure 1A:
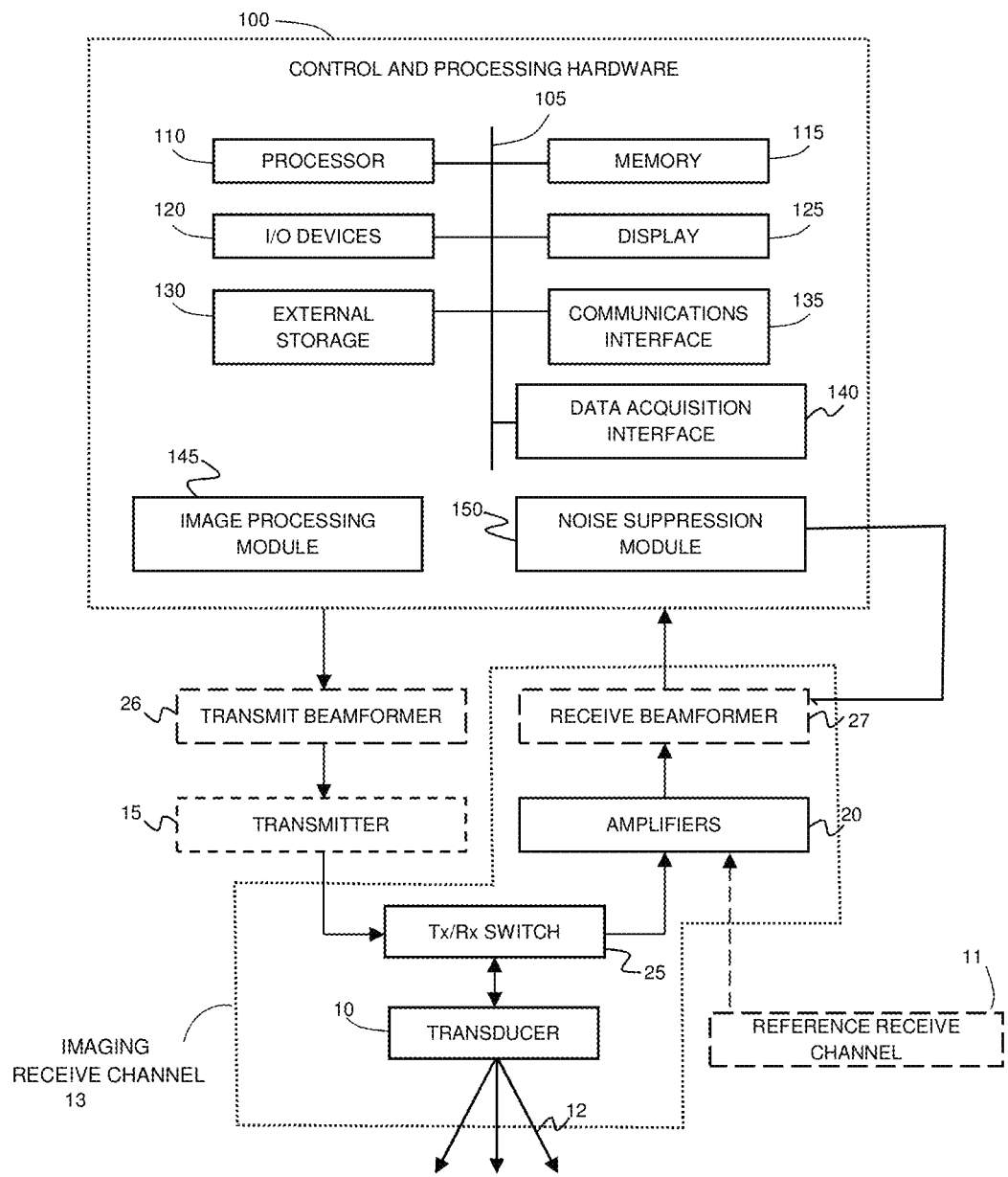
FIG. 1A shows an example of an ultrasound imaging system configured for noise suppression.

Referring now to FIG. 1A, an example ultrasound imaging system is shown, in which one or more ultrasound transducers 10 are controlled to perform ultrasound imaging across a plurality of scan lines 12. The transducer 10 interfaces with control and processing hardware 100, which optionally controls a transmitter 15 for the generation and emission of imaging energy by the transducer 10. The control and processing hardware 100 is configured to receive ultrasound energy signals detected by the transducer 10, which are routed, typically via a Tx/Rx (transmit-receive) switch 25, to one or more amplifiers 20.

The ultrasound transducer(s) 10 may optionally be configured to image a spatial region associated with a plurality of scan lines 12, for example, via mechanical scanning of the transducer 10, or, for example, via electronic scanning via the use of an array of imaging elements, such as, but not limited to, a phased array, ring array, linear array, matrix array or curvilinear array. In the latter case, a transmit beamformer 26 and receive beamformer 27 may be employed to generate a plurality of transmit signals and to beamform a plurality of received signals.

The term "receive circuit", as used herein, generally refers to components such as a transmission line (e.g. coax, PCB tracings, others), connectors, mux/demux, RX/TX switches 25, amplifiers 20, slip rings, transformers and other components known in the art.

The term "transducer receive circuit", as used herein, may include a receive circuit connected to one or more ultrasound transducer elements 10 configured to receive ultrasound signals at the time of use.

The phrase "ultrasound receive signal chain", as used herein, includes a receive circuit, but can include additional components such as analog-to-digital converters (ADCs) and further digital processing components and/or processing logic, including, but not limited to, noise removal processing module 150, before the signal enters the process of being converted into an image (such as via scan conversion) and subsequent image processing.

As used herein, the term "channel" may refer to conductive electrical circuits, wireless channels, optical channels, or other signal paths. For example, an imaging receive channel, which denotes the path traversed by detected imaging signals, is shown at 13 in FIG. 1A. The system may employ a single receive channel per transducer, or several receive channels per transducer (such as may be the case for an array transducer where there may a channel for each piezoelectric transducer element or groups of piezoelectric transducer elements in the array). ASICs and other devices may be used along the signal receive chain to multiplex signals along a channel from more than one piezoelectric transducer elements.

In an "imaging mode", the system may be configured to control the transducer 10 to optionally transmit energy to a medium, and to detect imaging energy within an imaging frequency band (henceforth referred to as an "imaging band"). The imaging band may constitute a single continuous frequency band, or two or more frequency intervals (such as in harmonic imaging), within which imaging energy is detected. Imaging energy or noise within the imaging band are henceforth referred to as being "in-band".

FIG. 14 is a representation of the grouping and terminology used to describe the various waveforms.

The system may also be configured to detect, via one or more channels connected to the transducer, energy in one or more additional frequency bands, where at least one frequency band lies, at least in part, beyond the imaging band. These one or more additional frequency bands are henceforth referred to as "detection bands". A waveform that lies, at least in part, beyond an imaging band is henceforth referred to as being "out-of-band". In some cases, a detection band may reside within the imaging band. A waveform that lies entirely within the imaging band, with frequency components lying either within the entire imaging band or in sub-bands within the imaging band is henceforth referred to as being "within-band". Noise-detection bands may be either out-of-band or within-band. At least one detection band may be selected such that the signal-to-noise ratio within the detection band is substantially less than the signal-to-noise ratio in the imaging band when the transducer is used in an imaging mode (i.e. when the transducer detects imaging energy). For example, the detection band may lie outside the full-width, half-maximum bandwidth of the imaging band or another bandwidth corresponding to a threshold below the maximum strength of the signal employed.

As used herein, "imaging waveform" refers to a waveform (analog or digitally sampled) that is obtained from an imaging transducer receive circuit when the imaging transducer is receiving or is expected to be receiving imaging energy.

As used herein, the phrase "in-band imaging waveform" refers to an imaging waveform (analog or digitally sampled) that lies in the imaging band. An in-band imaging waveform is expected to include imaging energy and may also include unwanted noise energy. In various example embodiments of the present disclosure, an in-band imaging waveform is processed to remove noise energy for the generation of a denoised image.

As used herein, the phrase "detection-band imaging waveform" refers to a waveform obtained from an imaging transducer receive channel and residing within one or more noise detection bands. A detection-band imaging waveform may be out-of-band or within-band. A within-band noise-detection imaging waveform may be employed, for example, in order to confirm the presence of noise within the imaging band. More specifically, a "within-band noise-detection imaging waveform" may be employed to confirm that a noise source having a noise component outside of the imaging band also has a noise component within the imaging band. A detection-band imaging waveform that lies, at least in part, outside the imaging band is referred to as an "out-of-band noise-detection waveform".

Referring to FIG. 1A, the system may be configured to be in a "noise-characterization mode", during which the transducer 10 does not transmit energy to a medium, and does not detect imaging energy from the medium.

As used herein, the phrase "noise-characterization waveform" refers to a waveform obtained when the imaging transducer is not receiving imaging energy.

As used herein, the phrase "in-band noise-characterization waveform" refers to a waveform that resides in the imaging band, obtained from an imaging transducer receive channel when the imaging transducer is not receiving imaging energy.

As used herein, the phrase "detection-band noise-characterization waveform" refers to a waveform that resides in a noise detection band, obtained from an imaging transducer receive channel when the imaging transducer is not receiving imaging energy. A detection-band noise characterization waveform that lies, at least in part, outside the imaging band is referred to as an "out-of-band noise characterization waveform". A detection-band noise characterization waveform that lies entirely within the imaging band is referred to as a "within-band noise characterization waveform".

As used herein, the phrase "baseline noise-characterization waveform" refers to a waveform obtained when the imaging transducer is not receiving imaging energy, and when a selected noise source is expected to be off (i.e. absent of producing noise), such that the baseline noise-characterization waveform provides a baseline for the selected noise source. A baseline noise-characterization waveform that lies in an imaging band is referred to as an "in-band baseline noise-characterization waveform". A baseline noise-characterization waveform that lies in a noise-detection band is referred to as a "detection-band baseline noise-characterization waveform".

Referring again to FIG. 1A, an optional reference receive circuit 11 may be provided that includes a receive circuit configured not to receive reflected ultrasound signals during imaging, while being capable of detecting noise energy similar to the noise that gets coupled into one or more transducer receive circuits during imaging. A reference receive circuit may employ one or more components of a transducer receive circuit (for example, a reference receive circuit and a transducer receive circuit may utilize different channels of an amplifier or an ADC).

In one example implementation, the system may be configured to detect noise within the imaging band via one or more reference receive channels, optionally connected to a reference ultrasound transducer (not shown) that is acoustically isolated or inactivated such that it does not transduce reflected ultrasound waves but is sensitive to the noise received by the imaging transducer receive circuit. The one or more imaging transducers 10 and the one or more reference transducers need not be oriented in a common spatial direction.

The signals received by the one or more reference transducer receive circuits or reference electrical receive circuits (on a reference receive channel) are henceforth referred to as reference waveforms. A reference waveform is predominantly noise and not imaging energy.

As used herein, the phrase "reference waveform" refers to a waveform obtained from one or more reference receive channels. A reference waveform may be filtered to reside within the imaging band and/or outside the imaging band.

As used herein, the phrase "reference noise-detection waveform" refers to a reference waveform obtained from a reference receive channel when the imaging transducer is receiving or is expected to be receiving imaging energy.

As used herein, the phrase "reference noise-characterization waveform" refers to a reference waveform obtained from a reference receive channel when the imaging transducer is not receiving imaging energy.

The system may optionally be configured to suppress noise using a combination of detection-band waveforms and reference waveforms. As used herein, the phrase "noise-detection waveform" refers to either a reference waveform or a detection-band waveform. When the system is in imaging mode and the imaging transducer receive circuit is receiving or expected to receive imaging energy, a noise-detection waveform is referred to as a "noise-detection imaging waveform". When the system is in a noise-characterization mode and the imaging transducer receive circuit is not receiving imaging energy, the noise-detection waveform is referred to as a "noise-detection characterization waveform".

Although FIG. 1A shows a single transducer element, it will be understood that the embodiment shown in FIG. 1A merely provides but one non-limiting example configuration, and that transducers with multiple piezoelectric elements may be employed. For example, in one example embodiment, a plurality of transducer elements may be controlled as a phased array or linear array or 2D array. Further, the transducer may not be limited to one that transmits imaging energy for the purpose of producing multi-dimensional 2D cross sectional images or 3D volumes (including 4D imaging datasets comprising 3D images over time), but may include transducers used for Doppler assessment of flow, transducers used as ultrasound beacons (e.g. as described in US Patent Publication No. 2016/0045184, titled "Active localization and visualization of minimally invasive devices using ultrasound", which is incorporated by reference in its entirety), or ultrasound transducers used to sense the position of moving elements (e.g. as described in US Patent Publication No. 2012/0197113, titled "Ultrasonic probe with ultrasonic transducers addressable on common electrical channel", which is incorporated by reference in its entirety).

The transducer may not be limited to one that both transmits and receives imaging energy as shown in FIG. 1A, but may include transducers that receive ultrasonic energy from a medium that has been excited by other means, such as an optical energy (photoacoustic imaging), or by a separate ultrasound transducer. Further, although FIG. 1A shows a configuration to image a spatial region associated with a plurality of scan lines at different directions, the scan lines may be unidirectional, such as in M-mode imaging or during certain Doppler modalities, such as pulse-wave or continuous wave Doppler to assess flow.

In one example embodiment, a single transducer receive channel is configured to receive imaging energy within the imaging band, and to coincidentally also receive additional energy within one or more noise-detection bands, of which at least one comprises out-of-band noise. In another example, one or more imaging transducer receive channels may be employed to receive imaging energy within the imaging band, and one or more transducer receive channels may be employed to receive additional energy within one or more noise-detection bands of which at least one comprises out-of-band noise. In yet another example, one or more reference receive channels may be employed to receive noise energy (i.e. reference noise-detection waveforms) while being isolated from the imaging energy in the imaging band. The reference receive channel may be filtered in a manner similar to the imaging transducer receive channel by using an imaging band pass filter. Alternatively, in several embodiments, the reference receive channel may not be filtered at all, or may have different filters other than an imaging band pass filter to better facilitate estimation of noise within the imaging band.

The control and processing hardware 100 may include, for example, one or more processors 110, memory 115, a system bus 105, one or more input/output devices 120, and a plurality of optional additional devices such as communications interface 135, data acquisition interface 140, display 125, and external storage 130.

It is to be understood that the example system shown in FIG. 1A is illustrative of a non-limiting example embodiment, and is not intended to be limited to the components shown. For example, the system may include one or more additional processors and memory devices. Furthermore, one or more components of control and processing hardware 100 may be provided as an external component that is interfaced to a processing device. For example, as shown in the figure, an optional transmit beamformer 26 and an optional receive beamformer 27 may be included as a component of control and processing hardware 100 (as shown within the dashed line), or may be provided as one or more external devices.

Some aspects of the present disclosure can be embodied, at least in part, in software, which, when executed on a computing system, configures the computing system as a specialty-purpose computing system that is capable of performing the signal processing and noise reduction methods disclosed herein, or variations thereof. That is, the techniques can be carried out in a computer system or other data processing system in response to its processor, such as a microprocessor, CPU or GPU, executing sequences of instructions contained in a memory, such as ROM, volatile RAM, non-volatile memory, cache, magnetic and optical disks, cloud processors, or other remote storage devices. Further, the instructions can be downloaded into a computing device over a data network, such as in a form of a compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine-readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), network attached storage, cloud storage, among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Many of the embodiments described herein employ the adjustment of a noise reduction filter based on noise sensed in the environment. In some example implementations, one or more of waveforms, data, filter parameters and other pertinent information described in the example embodiments below may be transmittable to a network and assessed remotely for further analysis and/or optimization of the noise reduction filter implementation. Once optimized, the noise reduction filter algorithms and/or parameters can then be transmitted to the system to enable improved noise reduction.

As shown in FIG. 1A, the example control and processing hardware 100 includes an imaging processing module 145 and a noise suppression module 150. The image processing engine 145 may be configured or programmed to execute known image processing methods, such as scan conversion.

While several of the present embodiments are illustrated and described in a manner that enables real-time noise reduction, it is to be understood that the noise reduction could occur in a post-processing fashion. For example, the data on a transducer receive channel or a reference receive channel could be digitized and stored before or after any filtering, envelope detection, shifting, shape/phase or delay adjustments, signal characterization, attenuation, subtraction or other steps in the described embodiments of the present invention.

Figure 1B:
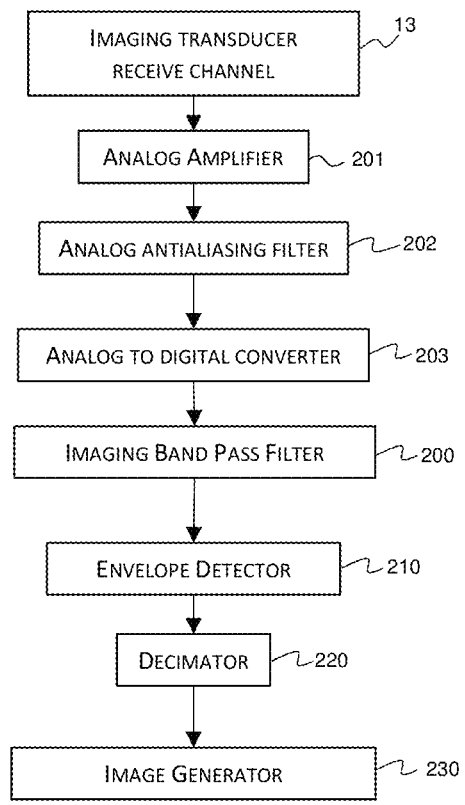
FIG. 1B shows an example of a conventional ultrasound receive signal chain for the processing of an ultrasound signal before conversion to an ultrasound image.

FIG. 1B illustrates an example of steps that may be employed by the control and processing hardware 100 and receive channel to process a detected an in-band imaging waveform from an imaging transducer receive channel prior to image generation. The detected waveform from an imaging transducer receive circuit may be amplified 201 and filtered 202 prior to analog-to-digital conversion 203. Once digitized, a band-pass filter 200 (which may employ multiple pass bands and stop bands) is employed to filter the detected waveform and retain the signal in the imaging band. The envelope of the filtered waveform is then generated through an envelope detector 210. The resulting envelope-detected waveform is then optionally decimated or expanded 220 and provided to the image processing module 230 for the generation of an image.

Referring again to FIG. 1A, the example control and processing hardware 100 includes one or more noise suppression modules 150, which includes instructions for processing detected data (e.g. raw RF data, envelope data, or image data) to reduce a contribution of noise, according to noise reduction algorithms described in detail below. As described below, the noise suppression algorithms disclosed herein (and represented in FIG. 1A by noise suppression module 150) may be employed to remove or reduce noise at several potential steps during the processing flow shown in FIG. 1B, based on processing one or more noise-detection waveforms. In the case of systems using array transducers, noise suppression may occur either before or after beam-forming (or both). In various example embodiments described in detail below, noise reduction of imaging data (including, but not limited to, raw waveforms, sampled waveforms, envelope waveforms, Fourier transformed signals, and processed image data) is performed based on measurements of signal energy (power, amplitude, intensity, or other measures of signal strength) or waveform patterns of the noise-detection waveform (such as an out-of-band noise-detection imaging waveform detected via an imaging receive channel or a reference noise-detection waveform detected on a reference receive channel). A noise-detection waveform, which in many embodiments is substantially absent of imaging energy, may contain noise that is correlated with or coincidental with the noise within the imaging band (or imaging bands). One or more relationships between the imaging band noise and the noise detected by the noise-detection waveform may be employed for the correction of imaging band signals for the removal or reduction (e.g. suppression) of imaging band noise.

Implementation of a Reference Receive Circuit for Intracorporeal Imaging

Figure 1C:
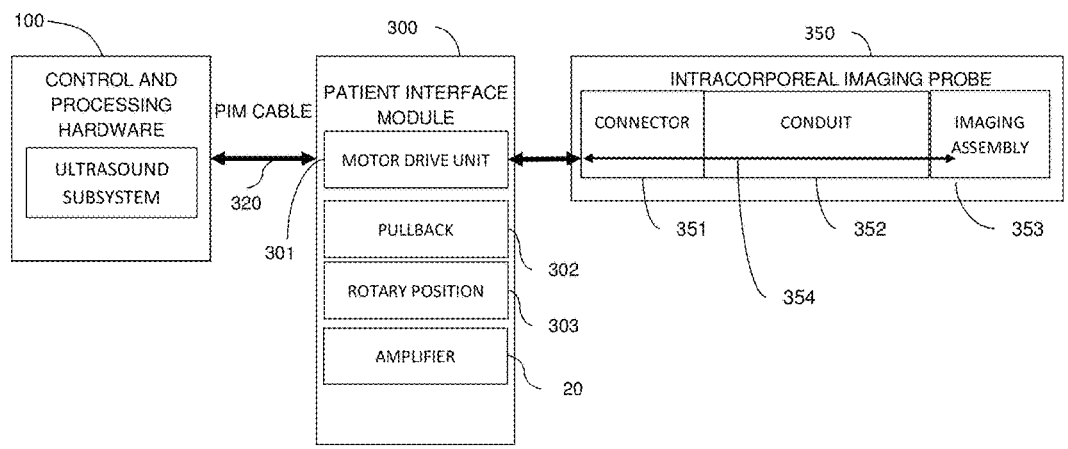
FIG. 1C shows an example of an ultrasound imaging system including an intracorporeal imaging probe.

Referring now to FIG. 1C, an example system is shown for ultrasound imaging of a region with an intracorporeal imaging probe 350 which connects via patient interface module (PIM) 300 to a control and processing hardware 100. The intracorporeal ultrasound imaging device may be configured to receive acoustic imaging energy from a one-dimensional, two-dimensional or three-dimensional region, optionally via mechanical or electronic scanning.

The imaging probe 350 comprises an imaging assembly 353 remote from its proximal end with an electrical and/or optical channel 354 that passes through an optional conduit 354 along at least a portion of its length, and a connector 351 at its proximal end. For the purposes of the present disclosure, an imaging assembly 353 generally refers to a component or collection of components of the imaging probe 350 with which imaging energy (e.g. acoustic or optical signals) is detected for the purposes of imaging a region that is adjacent to the imaging assembly. The imaging assembly may optionally include one or more emitters of imaging energy, and includes at least one receiver of imaging energy. For example, the imaging assembly may contain an ultrasonic imaging transducer 10 that is both an emitter and receiver of acoustic energy. The ultrasonic imaging transducer may be mounted on an imaging assembly that is optionally attached or otherwise connected to a rotatable conduit or shaft (e.g. a torque cable) 352 housed within a hollow sheath of an intracorporeal ultrasound imaging probe to facilitate mechanical scanning.

Optional PIM 300 facilitates transmission of signals within any wires or conduits to the appropriate image processing unit 100 via a PIM cable 320, such as when the imaging probe 350 does not connect directly to the control and processing hardware 100. The PIM may incorporate one or more amplifiers 20 to amplify the signals from one or more transducer receive channels. The PIM may optionally incorporate a motor drive unit 301 that imparts rotational motion to a rotatable conduit 354. Motor drive unit 301 may include slip rings, rotary transformers or other components that couple the signals of probe 350 to control and processing hardware 100, thus allowing the imaging conduit to rotate while the PIM cable 320 does not. The PIM 300 may also optionally incorporate a pullback mechanism 302 or a reciprocating push-pull mechanism to facilitate longitudinal translation of the imaging assembly 353. Such longitudinal translation of the imaging assembly may occur in conjunction with the longitudinal translation of an external shaft that surrounds the imaging conduit, or may occur within a relatively stationary external shaft.

Many electrical components within the imaging system may pick up unwanted energy from environmental noise sources. Examples of such components include the imaging assembly 353, the imaging conduit 352, the motor drive unit 301 and the PIM cable 320. One or more reference receive circuits that detect noise correlated with the noise detected by an imaging receive circuit may be useful in suppressing in-band noise. The following are example implementations of reference receive circuits for noise reduction of an imaging signal in an ultrasound imaging system.

Figure 1D:
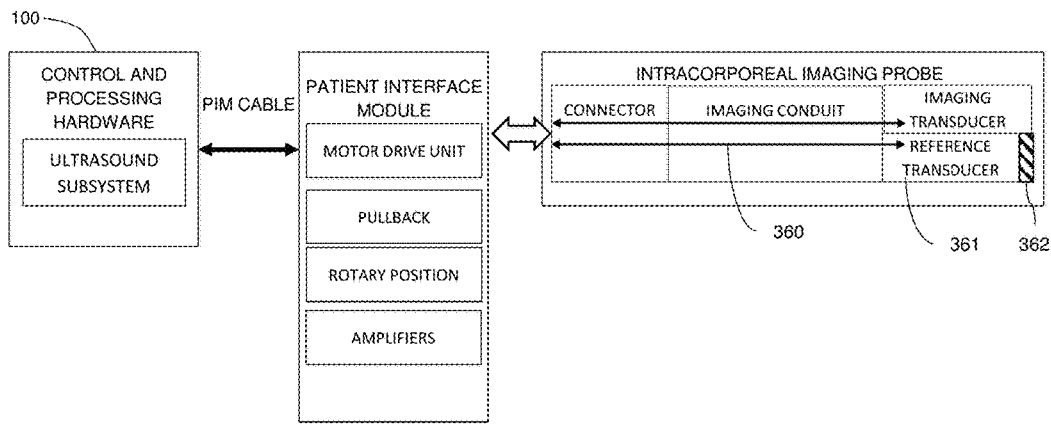
FIG. 1D shows an example of an ultrasound imaging system including a reference transducer for detecting in-band noise.

FIG. 1D illustrates an example embodiment in which the imaging transducer is replicated by one or more non-imaging reference transducers 361 that resides within the imaging probe 350. The reference transducer has its own electrical channel 360 that passes through the optional conduit 352 and connector 351. The reference transducer 361 may be coated with epoxy or with some other acoustic damping material 362 so that it is acoustically isolated from receiving imaging energy. Alternatively, the piezoelectric may be de-poled to render the piezoelectric inactive, or may otherwise be substituted with a substrate that is not acoustically sensitive. This implementation may be extended to array transducers, where there may be a plurality of ultrasound transducer elements that are configured to receive acoustic imaging energy. One or more elements of the array may be acoustically insensitive so that it does not transduce acoustic imaging energy and can function as a reference transducer receive circuit.

Figure 1E:
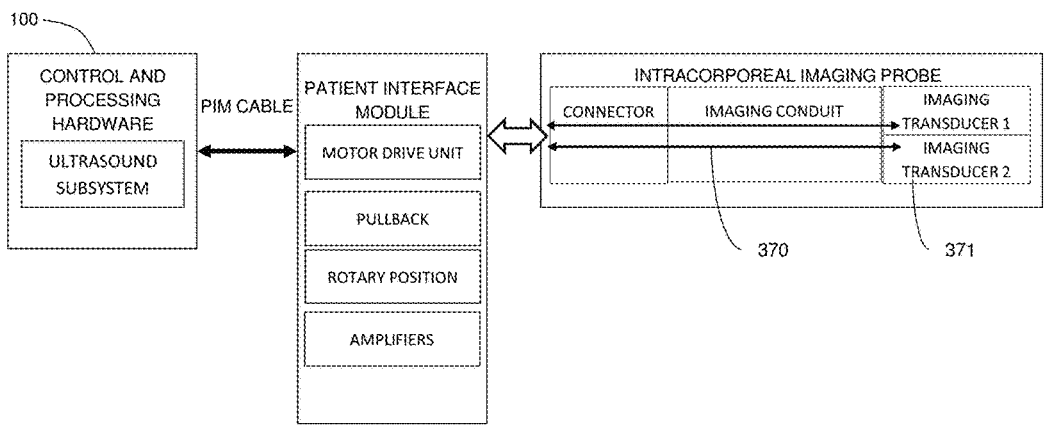
FIG. 1E shows an example of an ultrasound imaging system including a second imaging transducer having an imaging band that lies outside the imaging band of a first imaging transducer. The second imaging transducer may be part of a circuit suitable for detecting in-band noise that affects the signals received from first imaging transducer.

FIG. 1E illustrates an example embodiment in which the imaging probe contains two or more imaging transducers, each with a separate electrical channel, 370 and 354. The two or more imaging transducers may be sensitive to receive acoustic imaging energy at substantially non-overlapping spectral bandwidths. For example, the first transducer may be configured to receive acoustic energy for frequencies around 10 MHz, and a second imaging transducer may be configured to receive imaging energy for frequencies around 40 MHz. The 40 MHz band of the 10 MHz-transducer may act as a reference noise channel for the 40 MHz-transducer, and similarly, the 10 MHz band of the 40 MHz-transducer may act as a reference noise channel for the 10 MHz-transducer.

Figure 1F:
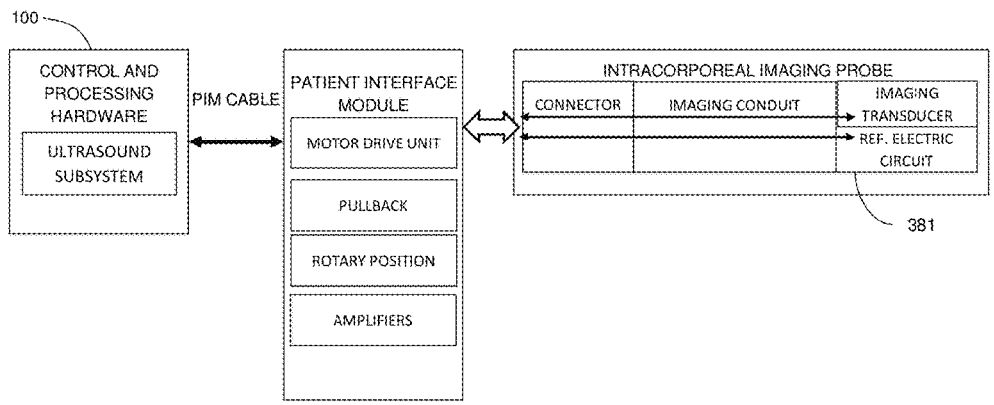
FIG. 1F shows an example of an ultrasound imaging system including a reference receive circuit for detecting in-band noise, where the reference receive circuit extends to a location within the imaging probe.

FIG. 1F illustrates an example embodiment in which the imaging transducer receive channel is replicated by a reference receive circuit that resides within the imaging probe. The reference receive circuit may optionally have some combination of resistors, inductors, capacitors and/or other components, configured such that electrical impedance of the reference electric circuit 381 is matched to the impedance of the imaging transducer receive circuit or such that the sensitivity of the reference electric circuit to noise is rendered more similar to the sensitivity of the transducer receive channel to noise. The advantage of such embodiments is that they may be less expensive, easier to manufacture and easier to miniaturize some of the components of reference electric circuit 381 by not requiring an actual ultrasound transducer. Furthermore, a portion of the reference receive circuit may serve additional purposes, such as transmitting energy to drive an actuator (such as, but not limited to, a magnetic actuator), or carrying a signal (including, but not limited to temperature, pressure or current generated from an electromagnetic field for position sensing). Such use of the reference receive circuit for additional purposes other than solely collecting a reference noise-detection waveform to reduce noise in the imaging signal may allow for easier miniaturization, lower costs and/or improved functionality.

Figure 1G:
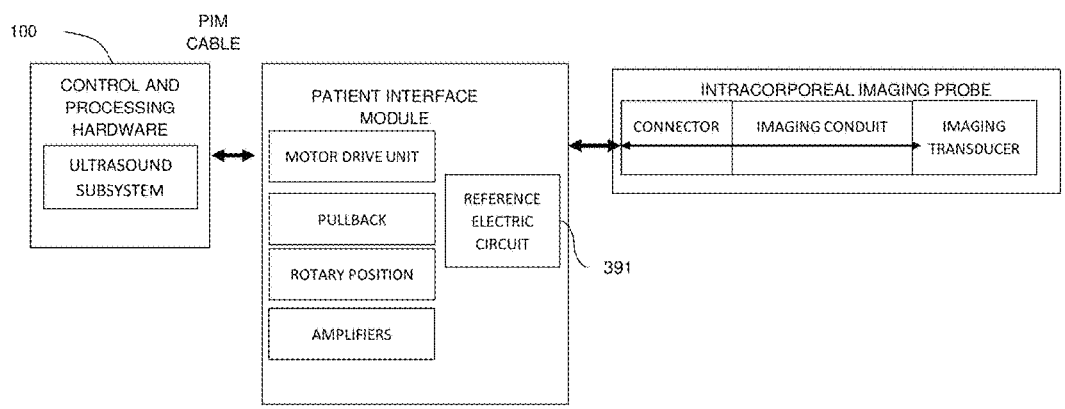
FIG. 1G shows an example of an ultrasound imaging system including a reference receive circuit for detecting in-band noise, where the reference receive circuit is located in one or more portions of the system that are external to the imaging probe.

FIG. 1G illustrates an example embodiment in which the reference receive circuit 391 terminates within the PIM where, similar to the imaging receive channel, it is subject to noise received by the motor drive unit and the PIM cable. Here only a portion of the transducer receive circuit is replicated. Reference noise detection may optionally be used in combination with detection-band (out-of-band or within-band) noise detection to further reduce noise of an in-band imaging waveform from an imaging transducer receive channel.

It is noted that the embodiments in which a detection-band waveform is employed as the noise-detection waveform may be less costly to produce than those that employ the use of a reference circuit or reference transducer to generate a reference waveform, as the former does not require the physical implementation of a reference channel, such as in cases where an imaging probe, or part thereof is not used repeatedly across different patients. It is also noted that a noise-detection waveform from a reference channel may be more effective in some imaging systems at reducing noise, as it can provide information about noise that resides within the imaging band, whereas an out-of-band noise-detection waveform does not provide a direct estimate of the in-band noise and instead relies on noise whose in-band properties can be predicted based, at least in part, on its out-of-band properties.

It is also noted that the noise estimates obtained using either a detection-band waveform or a reference noise-detection waveform may be used to reduce noise in more than one imaging channel. For example, in a phased array transducer, where there are a plurality of piezoelectric elements, it is possible to use a single reference receive channel or a single out-of-band noise-detection waveform to estimate noise that might be collected by all or a subset of the piezoelectric elements, and thus apply the same noise estimation scheme to the signals collected from all or a subset of the piezoelectric elements.

Noise Measurements

The following sections of the present disclosure describe several different example embodiments for performing noise reduction of in-band image data based on out-of-band noise detection, or reference channel noise detection, or a combination of both out-of-band noise detection (possibly supplemented further by in-band noise detection) and reference channel noise detection.

As will be described in relation to the following illustrative example embodiments, various noise measurements and/or noise characteristics may be determined from the measurements in the noise-detection waveform in order to increase the signal-to-noise ratio within the imaging band. Non-limiting examples of noise measurements include any one or more of:

measurements of energy (amplitude, root-mean-square amplitude, average power) in the noise-detection imaging waveform and the in-band imaging waveform;

measurements of energy in two or more different noise-detection bands;

temporal, spectral and/or time-frequency properties of the noise-detection waveform; or spatial or spatio-temporal patterns in images created using a noise-detection waveform, including features or parameters that describe or characterize such patterns;

temporal, spectral and/or time-frequency properties of in a noise-detection imaging waveform and co-incidental patterns in the in-band imaging waveform, including features that describe these patterns; spatial or spatio-temporal patterns in images created using a noise-detection waveform and co-incidental spatial patterns in images created from the in-band imaging waveform from an imaging transducer receive channel, including features or parameters that describe or characterize such patterns;

filter parameters that are determined or controlled using parameters obtained based on waveform characteristics, such as energy, and spectral spacing of harmonic peaks, detected in a noise-detection waveform.

In some example embodiments, the estimation of noise characteristics may be performed when an imaging transducer is not receiving imaging energy (e.g. after ultrasound energy from the most recent emission of an ultrasound pulse is expected to have been extinguished from the environment). Alternatively, the estimation of noise characteristics may be performed during imaging, when imaging energy is expected to be detected (e.g. when the transducer is in image acquisition mode). In some example embodiments, in which noise characteristics are measured in the absence of imaging energy, such noise characteristics may be updated intermittently in order to adapt to and compensate for time-dependent changes in the noise characteristics.

Noise Reduction Using Measurements without Imaging Energy Present

Although some noise reduction embodiments involve the measurement and use of energy from a noise-detection waveform while the imaging transducers are receiving imaging energy, alternative embodiments may employ measurement from a noise-detection waveform that are obtained during time periods in which there is an absence of imaging energy, or a combination of both.

Figure 5A:
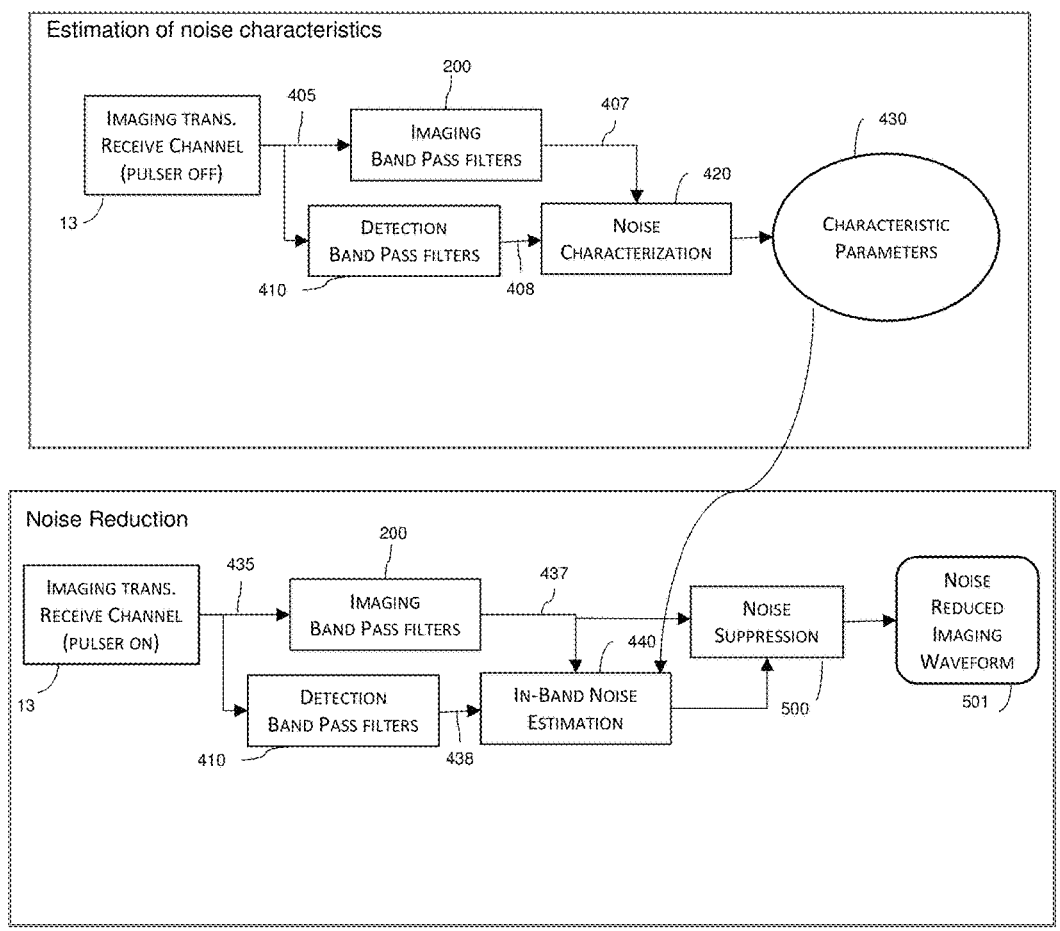
FIG. 5A schematically illustrates an example system configuration for noise reduction on an input waveform based on noise parameters obtained during a first measurement stage in the absence of an imaging signal, and by the application of one or more noise reduction algorithms that utilize the aforementioned noise parameters during a second measurement stage when imaging signals are collected.

FIG. 5A illustrates an example of such an embodiment, in which noise characterization is performed while the transducer receive channel is not receiving imaging energy, and where the resulting noise characterization can be employed to enable noise reduction of in-band imaging waveforms acquired while the transducer receive channel is receiving imaging energy. Typically, the noise characterization step would occur prior to the acquisition and processing of imaging data that is noise reduced, but with appropriate recording of the imaging data, the information gathered during noise characterization could be employed post-hoc on the recorded imaging data.

According to the present example method, energy is detected in a transducer receive circuit during a first time window when it is either anticipated or known that at least one transducer receive circuit is not receiving imaging energy, such that the waveform detected by an imaging transducer receive channel 13 is deemed to be noise 405. The detected waveform is filtered at 200 and 410 to generate an in-band noise characterization waveform 407 and an detection-band noise characterization waveform 408.

The in-band noise characterization waveform and the detection-band noise characterization waveform are processed to characterize their noise properties, as shown at 420. The noise characterization 420 may be employed, for example, to generate characteristic parameters 430 that characterize the noise. Examples of suitable noise characterization parameters are provided in the forthcoming example embodiments.

Optionally, energy may be detected in a transducer receive circuit during an additional baseline noise characterization stage when it is either anticipated or known that at least one transducer receive circuit is not receiving imaging energy, and a certain noise source is selectively known to be off, such that the waveform detected by an imaging transducer receive channel 13 is deemed to be baseline noise for a selected noise source. The detected baseline noise characterization waveform is filtered at 200 and 410 to generate an in-band baseline noise characterization waveform 407 and a detection-band baseline noise characterization waveform. It is to be understood that noise parameters 430 may include parameters obtained during a baseline noise characterization stage.

Characteristic noise parameters may be calculated before or during an imaging session, or may be retrieved from a pre-stored database located on a local or remote storage drive (network drive, cloud, etc.).

After having characterized the noise in the absence of imaging energy, the characteristic parameters 430 may be employed to perform noise reduction of the in-band imaging waveform 437 detected while the transducers are receiving imaging energy. The waveform detected from an imaging transducer receive channel during imaging 435, containing imaging energy and noise, is filtered at 200 and 410 to generate an in-band imaging waveform 437 and a detection-band imaging waveform 438. Therefore, the in-band imaging waveform 437 contains detected imaging energy and noise, and the detection-band imaging waveform 438 contains information associated with the likely presence of noise in the in-band imaging waveform 437. The characteristic parameters 430 obtained during the noise characterization stage may then be employed for the detection and/or estimation of noise 440 within the in-band imaging waveform, and to perform noise suppression 500 of the in-band imaging waveform. Examples of suitable noise characterization parameters are how they are used to reduce noise are provided in the forthcoming example embodiments.

Figure 5B:
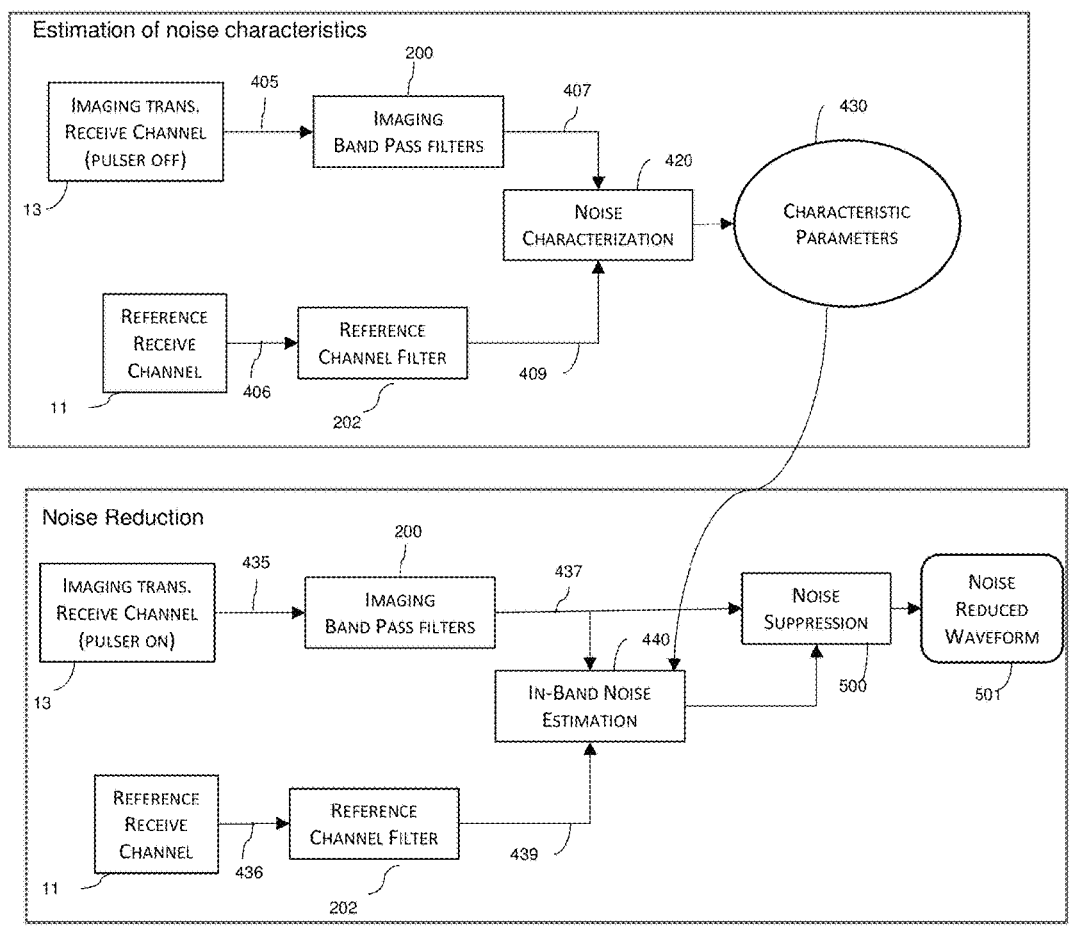
FIG. 5B schematically illustrates an alternative example system in which a reference receive channel is employed to detect in-band noise.

FIG. 5B illustrates an alternative embodiment in which a reference receive channel, such as the reference receive channel described with reference to FIG. 1A, is employed to detect noise and generate a reference noise characterization waveform 406. This reference noise characterization waveform is filtered at 202 to generate a filtered reference noise characterization waveform 409. In one example embodiment, the reference channel filter could be an imaging band pass filter. Alternatively, if the noise estimation benefits from input of out-of-band noise, then the reference channel filter may be different from an imaging band pass filter. The reference noise characterization waveform 409, and optionally the in-band noise characterization waveform 407, are processed at step 420 to provide noise characterization parameters 430.

During imaging, a reference waveform 436 is detected and optionally filtered to generate a filtered reference noise-detection waveform 439. The characteristic parameters 430 obtained during the noise characterization stage may then be employed for the detection and/or estimation of noise 440 within the in-band imaging waveform 437, and to perform noise suppression 500 of the in-band imaging waveform 437. In another example embodiment, both the detection-band imaging waveform 438 (shown in FIG. 5A) and the filtered reference noise-detection waveform 439 are processed to provide information about the likely presence of noise in the in-band imaging waveform 437.

In some example embodiments, noise suppression may be achieved by processing the in-band imaging waveform using one or more of the following methods: subtracting the estimated noise from the signal in the imaging band; attenuation of the estimated noise energy by multiplying the signal in the imaging band with an attenuation factor; and filtering the signal in the imaging band. For example, a subtrahend value may be proportional to the amount of power detected within the out-of-band noise-detection imaging waveform. In another example, an attenuation factor may be inversely proportional to a measure associated with the amount of noise in the in-band imaging waveform, thereby attenuating portions of the in-band imaging waveform associated with noise.

Noise characterization (as shown, for example, at 420 in FIGS. 5A-B) may be performed once, or may alternatively be performed multiple times, or continuously. For example, noise characterization may be performed intermittently over time (e.g. at periodic or aperiodic intervals) in order to adapt to, and to compensate for, time-dependent changes in the noise characteristics. When noise characterization is occurring, the noise characterization waveforms collected for noise characterization may digitized and collected in multiple discrete arrays, such as arrays that are each long enough to store imaging data along a single scan line in ultrasound imaging, or they may be collected in a more continuous fashion as one or more data streams that get stored into a large array, a circular buffer or other data structure.

In some example implementations, noise characterization may be user initiated (e.g. by pressing a button), for example, at the start of an imaging session or when the user observes or suspects a degradation in image quality.

In other example implementations, noise characterization may be triggered, such as either automatically or after prompting the user, when the absence of imaging energy is detected. For example, periods of absence of imaging energy may be detected when the relative energy between an in-band imaging waveform and a noise-detection imaging waveform is unchanged for a prescribed period of time and lies within a predefined range. Periods of absence of imaging energy may also be determined, for example, when the energy in the in-band imaging waveform after noise correction at 501 is below a predefined threshold, indicating the absence of imaging energy.

The noise characterization step 420 may also be useful in alerting the user or the system that the noise profile has changed in a manner that may cause the noise reduction algorithm to adversely affect the system (if a new isolated source of noise is detected, the noise suppression module 500 may erroneously cause suppression of the in-band signal or be less effective at suppressing in-band noise). For example, a noise-detection waveform (e.g. the out-of-band noise-detection waveform 438 of FIG. 5A or a reference noise-detection waveform 439 of FIG. 5B) may be processed to determine that the noise characteristics have changed. For example, while performing noise reduction, an optional noise monitoring module could be employed that monitors the characteristics (such as peak energy, power, frequency content slope, skew, kurtosis, histogram or some other metrics) of the noise-detection waveform. If the characteristics of a noise-detection waveform change (e.g. if the peak energy exceeds a threshold value), the noise monitoring module can communicate with other parts of the system (such as via a message, interrupt, alarm or other) to alert that the noise content has changed.

In another implementation, an error value may be evaluated in a noise characterization stage, where noise suppression is performed on the in-band imaging waveform in the absence of imaging energy and the error value is the energy of the in-band imaging waveform after noise correction. If the error value exceeds a pre-defined threshold, an alert is generated. An alert may prompt a re-characterization of the noise, or the system may choose to ignore one or more out-of-band noise-detection bands or one or more reference receive channels in its noise removal algorithm.

Noise characterization 420 may also be useful in determining the noise sources in the environment. Noise sources may be determined, for example, by a pattern recognizer, such as one described in step 570 of FIG. 7A (described in greater detail in Embodiment 4). Information on the noise sources can be used, for example, in order to access a database (local or networked) to select parameters for noise suppression or in order to determine the sequence of noise reduction methods to be used. For example, it may be preferably to remove periodic noise first (as described in detail in Embodiment 6 FIG. 8A-D), followed by less periodic noise.

As a further example, noise characterization may be useful at detecting the type of electroanatomic mapping system being used during an ablation procedure, or detecting the activation and deactivation of an ablation catheter, such as a catheter that uses radiofrequency energy to perform ablation to treat arrhythmias. This may be achieved, for example, by a pattern recognizer such as one described in step 570 of FIG. 7A. The one or more noise-detection waveforms may further be capable of detecting the duration or the relative intensity or frequency of the ablation energy being applied. Such information could be useful to an intracardiac imaging system, as it may facilitate annotation of an imaging dataset with information about when a noise source, such as an ablation catheter, was activated during a procedure.

Noise suppression (as shown, for example, at 500 in FIGS. 5A-B) may be performed once, multiple times, intermittently or continuously. For example, noise suppression may be user initiated. Alternatively, noise suppression may be performed intermittently over time (e.g. at periodic or aperiodic intervals) in order to compensate for time-dependent noise source. In another example, noise suppression may be controlled by the external device that emanates the noise. For example, noise suppression may be enabled or disabled by the controls of an RF ablation generator, such that noise suppression is performed when RF energy is being delivered.

The following embodiments are described for one imaging waveform and one noise-detection waveform. It is to be understood that these embodiments may be extended to a plurality or imaging waveforms and/or a plurality of noise-detection waveforms.

Embodiment 1: Noise Reduction Based on Suppressing Envelope Detected Out-of-Band Noise with Optional Amplitude, Shape and Delay Correction Referring now to FIG. 2A, an example method is illustrated in which the out-of-band noise-detection waveform 438 is employed to perform noise reduction of the in-band imaging waveform 437 via a suppression operator 525. In one example embodiment, a suppression operator may be a subtractor that subtracts the estimated noise from the in-band imaging waveform 437. In another example embodiment, the suppression operator may be an attenuator that attenuates the in-band imaging waveform with an attenuation factor that is derived from the estimated noise. One or more transducer receive channels are employed to detect imaging energy, where the energy detected includes both the imaging band and the noise-detection band. The waveforms can be digitally sampled, split (or copied) and filtered thereby obtaining a sampled in-band imaging waveform 437 and a sampled out-of-band noise-detection imaging waveform 438. The sampled waveforms may be detected as a set of samples that are received in a time window (listening window). For example, in the case of ultrasound imaging, the listening window may occur immediately or shortly after pulsing an ultrasound transducer such that it emits energy into the adjacent environment. Pulsing could correspond to sending out one or more pulses.

In the example embodiment shown in FIG. 2A, the imaging waveform 435 is filtered (digitally or analog) using an imaging band pass filter 200 and a noise-detection-band filter 410 that spans frequencies outside the imaging band. Envelope detection may then be performed on the in-band imaging waveform 437 and out-of-band noise-detection imaging waveform 438, as shown at 210 and 411, respectively.

In the example embodiment shown in FIG. 2A, the out-of-band noise-detection imaging waveform 438 is employed to reduce noise of the in-band imaging waveform 437. Prior to suppression, the amplitude of the envelope-detected out-of-band noise-detection imaging waveform 438 is optionally scaled via an amplitude adjustment factor, as shown at 510, in order to compensate for differences in the noise power within the imaging band and the noise-detection band. In one example implementation, the amplitude adjustment factor may be determined based on the power spectrum of the noise, as determined in the absence of imaging energy, i.e. in a noise characterization stage. In another example implementation, the amplitude adjustment factor may be selected, or modified, by an operator, in order to provide a desired level of noise reduction, or determined after cross correlation at 580 (described below).

Prior to suppression, the envelope-detected out-of-band imaging waveform may be temporally dilated, compressed or shape-adjusted using some other linear or non-linear temporal scaling function, as shown at 510, in order to compensate for differences in the shape of the noise waveforms between the imaging band and the noise-detection band.

As shown at 510, it may also be beneficial to apply a delay correction to the envelope-detected out-of-band noise-detection imaging waveform prior to suppression. For example, the two bandpass filters 200 and 410 may not transform the input waveforms similarly. Either the band pass filters or the properties of the noise itself may result in an offset of the noise as it propagates through the band pass filters. In the absence of a delay correction, the noise may be erroneously shifted prior to suppression, which can negatively impact the noise reduced signal.

In one example implementation, delay adjustment may be achieved by calculating a cross-correlation between the in-band imaging waveform and the out-of-band imaging waveform, and aligning the waveforms at the point where the cross-correlation is maximum. In other words, cross-correlation can be employed to determine a time delay correction value for correcting the relative temporal misalignment of the envelopes of the in-band imaging waveform and the out-of-band imaging waveform.

The time delay correction value and the amplitude correction value may be calculated using a plurality of sampled in-band imaging waveforms and (co-incidental) sampled out-of-band noise-detection imaging waveforms (which may be referred to as "arrays"), or in one or more time windows in a sampled in-band imaging waveform and (co-incidental) a sampled out-of-band noise-detection imaging waveform.

In one example implementation, out-of-band noise may be interrogated as a plurality of noise-detection bands, and the dependence of the power on frequency among the plurality of noise-detection bands may be employed to select a suitable amplitude adjustment for estimating the noise power that is present in the imaging band for suppression at step 525. For example, the average noise power within multiple noise-detection bands may be fitted to a functional dependence on frequency, such as a linear fit, in order to estimate the noise power within the imaging band. This functional dependence on frequency may be determined in the absence of imaging energy i.e. in a noise characterization stage 420.

Figure 2B:
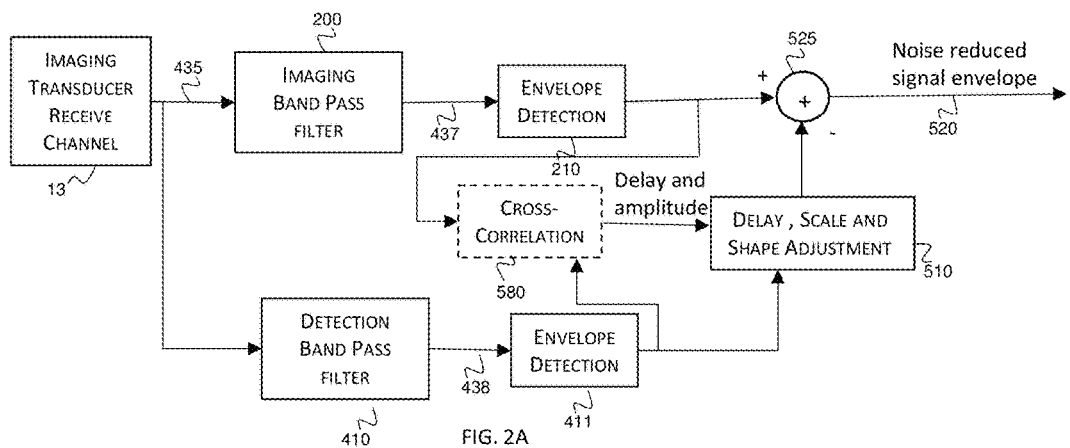
FIG. 2B illustrates an example system configuration for noise reduction on an input waveform via the estimation and subtraction of in-band noise, where the in-band noise is estimated by frequency shifting an out-of-band waveform, filtering the frequency-shifted out-of-band waveform, followed by delay, scale and shape adjustment prior to subtraction.
Figure 2B:
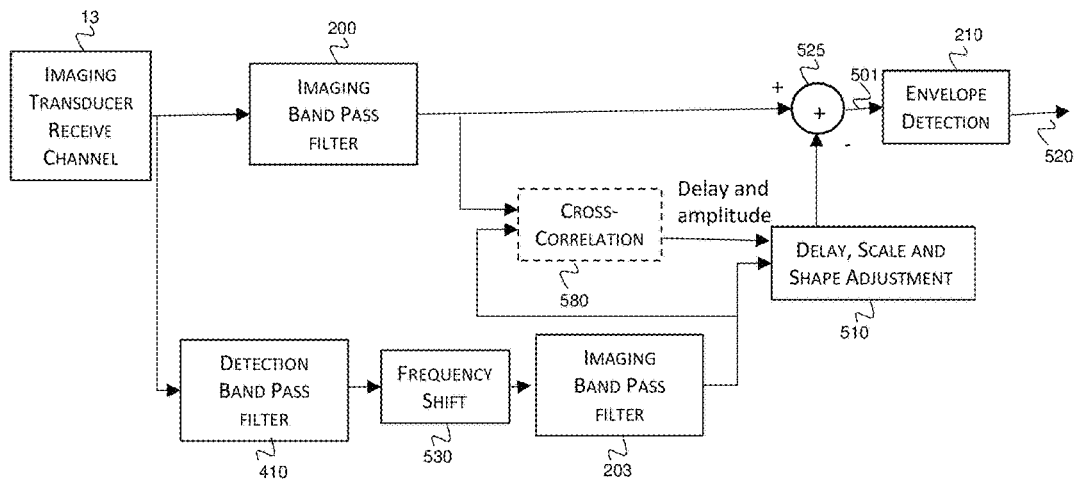

Alternate Embodiments: Noise Reduction Based on Using Frequency Shifted Out-of-Band Noise-Detection Waveforms with Optional Amplitude, Shape and Delay Correction FIG. 2B illustrates an alternative example embodiment of a subtractive or signal-attenuating noise correction method in which the out-of-band noise-detection imaging waveform is frequency-shifted prior to delay and amplitude adjustment. As shown at 530, a frequency shift operation (for example, by multiplying by a complex exponential) is performed on an out-of-band noise-detection imaging waveform, shifting the spectrum of the out-of-band noise-detection imaging waveform so that it lies within, or overlaps with the imaging band.

The frequency shift operation 530 may be performed such that the center frequency of the frequency-shifted noise-detection waveform coincides, or is approximately equal to, the center frequency of the imaging band. For example, if the imaging band ranges from 7-13 MHz, the center frequency is $f_{c1}=10$ MHz. If the noise-detection band ranges from 15-25 MHz, the center frequency of the noise-detection band is $f_{c2}=20$ MHz. Accordingly, the frequency shift operation may be performed such that the out-of-band noise-detection imaging waveform is shifted by $f_{c2}-f_{c1}=-10$ MHz. Alternatively, the frequency shift operation may be performed such that the center frequency of the frequency-shifted out-of-band noise-detection imaging waveform coincides, or is approximately equal to a frequency within the imaging band where it is anticipated or known that a portion of the in-band noise resides.

After frequency shifting, another stage of band pass filtering 203 is performed to filter out the sum-frequency artifact (in the aforementioned example, the sum frequency is $f_{c2}+10$ MHz=30 MHz). Frequency shifting may be advantageous over the envelope detection embodiment illustrated in FIG. 2A, because frequency shifting may result in better correlation between the noise in the imaging band and the noise-detection band, which may result in better noise suppression. It is noted that in the example embodiment shown in FIG. 2B, envelope detection 210 may be applied to the output signal 501 after it has undergone noise reduction to obtain a noise-reduced signal envelope 520.

Alternative Embodiments Based on Use of a Reference Noise Signal

Figure 2C:
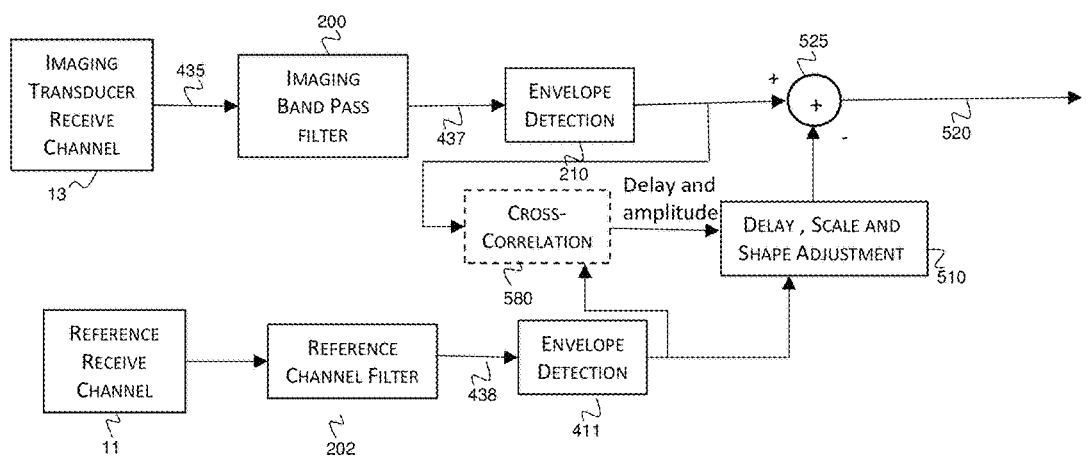
FIG. 2C illustrates an example of a system configuration for noise reduction with a reference receive circuit that is sensitive to some or all of the in-band noise that the imaging transducer receive circuit is sensitive to, but is at least partially isolated from the imaging signals detected by the imaging transducer receive circuit. The subtraction of the noise signals detected by the reference receive circuit from the signals received by the imaging transducer receive circuit reduce the noise in the output signal.

Referring now to FIG. 2C, an example method is illustrated in which in-band noise, detected via a reference receive channel (using a reference receive circuit) is employed to reduce noise in the in-band imaging waveform via a suppression operator (i.e. subtractor or attenuator). One or more imaging transducer receive channels are employed to receive imaging energy, and one or more reference receive channels are employed to receive noise energy (i.e. reference waveforms) that is anticipated to correlate with the noise energy received by the imaging transducer receive channel.

The waveforms may be digitally sampled, thereby obtaining sampled in-band imaging waveforms and sampled filtered reference noise-detection waveforms. Alternatively, the noise suppression could be performed with analog electronics, such as by using an analog signal adder with the input into the adder from the reference receive circuit being inverted in the delay, scale and shape adjustment block 510, thus resulting in subtraction of the estimated noise. As yet a further alternate embodiment for analog signal suppression, the suppression can be embodied as an amplifier with a time-varying gain, wherein the gain is modulated by the noise detected in the reference receive channel.

In the example embodiment shown in FIG. 2C, the input waveforms from an imaging transducer receive channel and the reference receive channel are filtered (digitally or analog) using an imaging band pass filter 200, and optional reference channel filter 202 thereby providing the in-band imaging waveform and a filtered reference noise-detection waveform, respectively. As mentioned previously, reference channel filter 202 may be similar to the imaging band pass filter 200. Envelope detection is then optionally performed on the filtered signals, as shown at 210 and 411. In the example embodiment shown in FIG. 2C, the reference noise-detection waveform, measured by the reference receive channel, is employed to reduce noise in the in-band imaging waveform. Prior to subtraction from the in-band imaging waveform (or its envelope) or attenuation of the in-band imaging waveform (or its envelope), the amplitude of the filtered reference noise-detection waveform (or its envelope) is optionally scaled via an amplitude adjustment factor, as shown at 510, in order to compensate for differences in the noise power within the filtered reference noise-detection waveform and the in-band imaging waveform. In one example implementation, the amplitude adjustment factor may be determined based on the power spectrum of the noise, as determined in the absence of imaging energy i.e. in a noise characterization stage. In another example implementation, the amplitude adjustment factor may be selected by an operator in order to provide a desired level of noise reduction or determined after cross correlation at 580.

As shown at 510, it may also be beneficial to apply a delay correction to the envelope-detected filtered reference noise-detection waveform prior to subtraction. In one example implementation, delay adjustment may be achieved by calculating a cross-correlation between the in-band imaging waveform and the filtered reference noise-detection waveform, and aligning the waveforms at the point where the cross-correlation is maximum. Similar to the previous embodiment, the time delay correction value and the amplitude correction value may be calculated using a plurality of in-band imaging waveforms and (co-incidental) reference noise-detection waveforms or one or more windows of an in-band imaging waveform and a (co-incidental) reference noise-detection waveform.

Figure 3A:
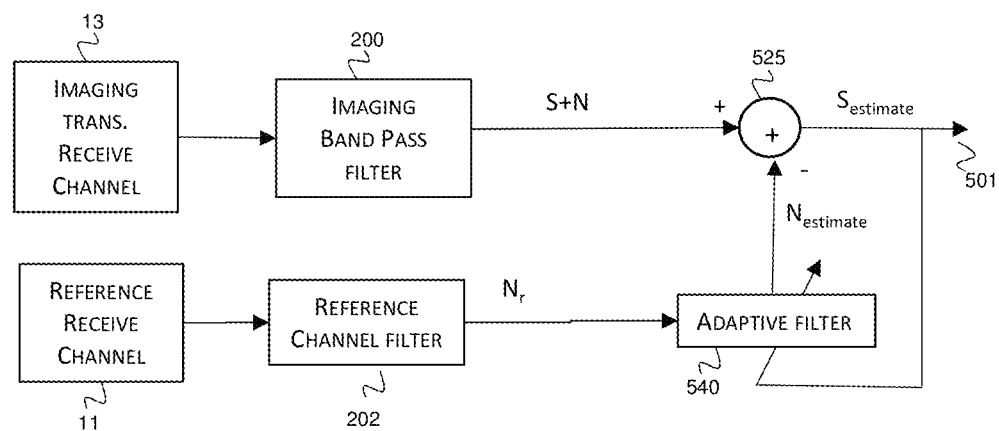
FIG. 3A illustrates an example of a system configuration for noise reduction via active noise cancellation, where a cancellation waveform for active noise cancellation is obtained from a reference receive circuit.

Embodiment 2: Noise Reduction Using Reference Noise-Detection Waveform from a Reference Receive Channel as Input to Adaptive Filter FIG. 3A illustrates an example embodiment of a noise correction method in which an adaptive filter is employed, in an active noise control (ANC) scheme, by applying a noise reducing correction to the in-band imaging waveform based on a reference noise-detection waveform, where the reference noise-detection waveform is correlated with the noise detected by an imaging transducer receive circuit. The reference noise-detection waveform is filtered at 202 and the waveform from the imaging transducer receive channel is filtered at 200. In a preferred embodiment, the in-band imaging waveform and the reference noise-detection waveform are filtered within the same band (e.g. 7-13 MHz for an exemplary intracardiac echocardiography imaging system).

An adaptive filter is a linear filter that has a transfer function controlled by variable parameters and a means to adjust those parameters according to an optimization algorithm. Adaptive filters are typically digital finite-impulse-response (FIR) or infinite-impulse-response (IIR) filters. An active noise control (ANC) scheme is provided for the primary input which receives a signal (S) from the signal source that is corrupted by the presence of a noise (N) that is uncorrelated with the signal. The reference input receives noise ($N_r$) that is uncorrelated with the signal but is correlated in some way with the primary input noise (N). The reference noise passes through an adaptive filter to produce an output noise ($N_{estimate}$) that is an estimate of the primary input noise (N). The noise estimate is subtracted from the corrupted signal to produce an estimate of the noise reduced signal ($S_{estimate}$). The adaptive filter actively adjusts its coefficients to minimize the output power $E[s_{estimate}^2]$. Since the signal S is uncorrelated with N and $N_r$, while noise N is correlated with noise $N_r$, minimizing the total output power maximizes the signal-to noise ratio. Minimization algorithms, such as a stochastic Least Mean Squares (LMS) algorithm or the deterministic Recursive Least Squares (RLS) algorithm may be used to find filter coefficients that minimize the output noise power.

In the example ANC scheme shown in FIG. 3A, the reference noise is measured via a reference receive channel using a reference receive circuit that is isolated from the imaging energy. The primary input is obtained by applying an imaging band pass filter 200 to an input waveform from an imaging transducer receive channel 13. A reference input $N_r$ is obtained by applying a reference channel filter 202 to the reference noise-detection waveform obtained via a reference receive channel.

Alternative Embodiments: Active Noise Cancelling Using Out-of-Band Noise

Figure 3B:
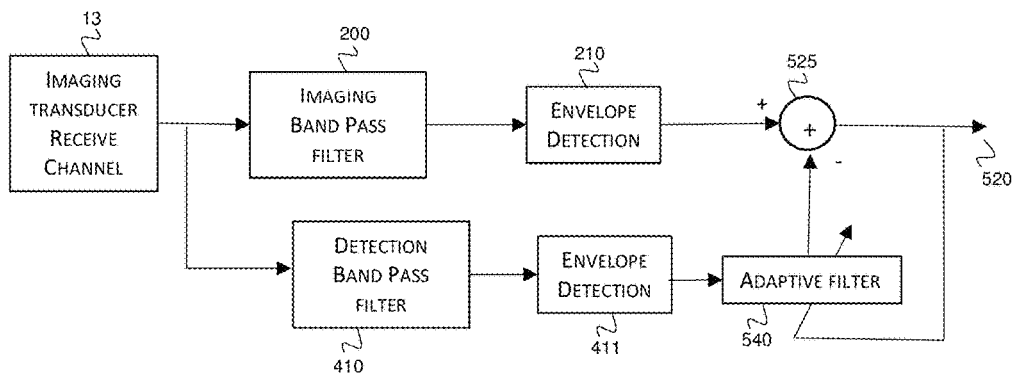
FIG. 3B illustrates an example of a system configuration for noise reduction on an input waveform via active noise cancellation, where a cancellation waveform for active noise cancellation is obtained by envelope detection of an out-of-band waveform.
Figure 3C:
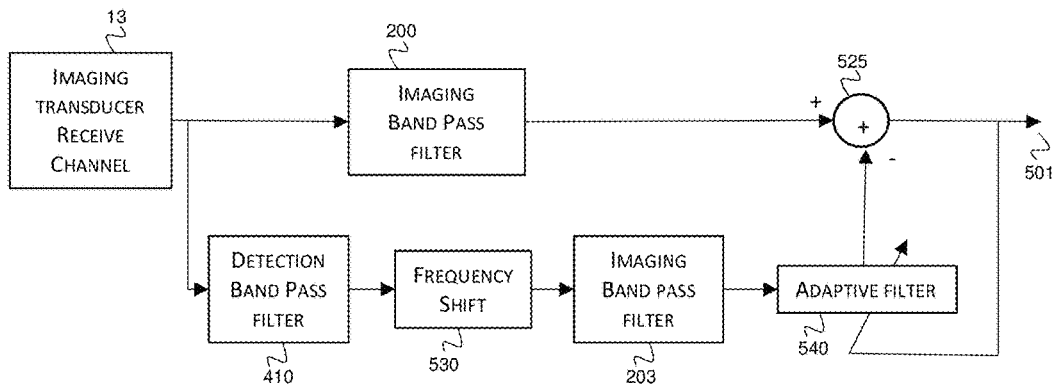
FIG. 3C illustrates an example of a system configuration for noise reduction on an input waveform via active noise cancellation, where a cancellation waveform for active noise cancellation is obtained by frequency shifting an out-of-band waveform and filtering the frequency-shifted out-of-band waveform.

Unlike the form of active noise control described above where the reference noise-detection waveform and the in-band imaging waveform may be detected and processed within overlapping frequency bands (and potentially a common frequency band), FIGS. 3B, and 3C illustrate example embodiments of noise correction methods in which an adaptive filter 540 is employed to apply a noise reducing correction to the in-band imaging waveform using an out-of-band noise-detection imaging waveform.

The primary input is obtained by applying an imaging band pass filter 200 to an input waveform from an imaging transducer receive channel, and obtaining its envelope 210. In example embodiments illustrated in FIGS. 3B and 3C, an out-of-band noise-detection imaging waveform is obtained by applying a detection band filter 410 to an input waveform from an imaging transducer receive channel.

In FIG. 3B, the out-of-band noise-detection imaging waveform is demodulated via envelope detection 411 (in a manner similar to the embodiment shown in FIG. 2A) to obtain a reference input for ANC.

In FIG. 3C, the out-of-band imaging waveform is frequency-shifted (at 530) to the imaging band (e.g. 7-13 MHz) in a manner similar to the embodiment shown in FIG. 2B and filtered using an imaging band pass filter 203 to obtain a reference input for ANC.

Figure 4:
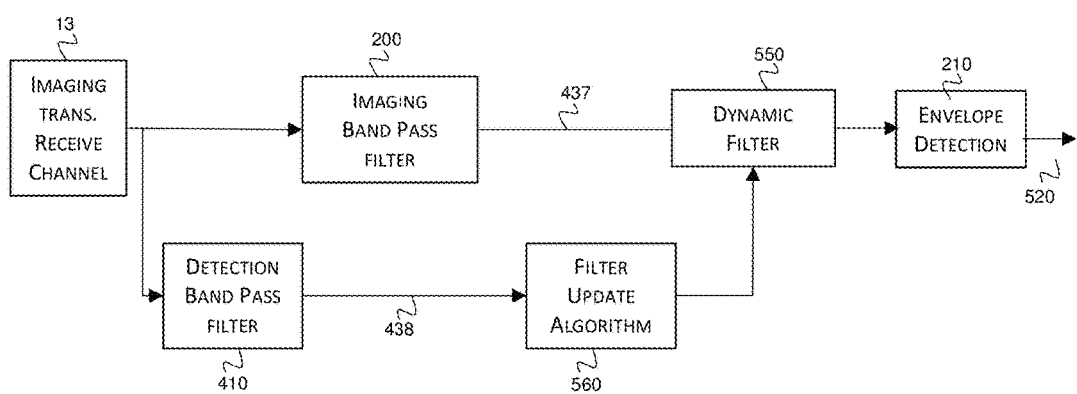
FIG. 4 illustrates an example of a system configuration for noise reduction on an input waveform via filtering of an in-band waveform, where the filtering is controlled based on a feedback parameter obtained by a filter update algorithm that determines one or more parameters of the filter based on one or more characteristics of a noise-detection waveform.

Embodiment 3: Noise Reduction Based on Frequency Shift, Using Detection-Band Waveform as Input to Variable Filter of in-Band Waveform FIG. 4 illustrates an example embodiment of a noise correction method in which a dynamic filter 550 is employed to filter the in-band imaging waveform, where the dynamic filter is controlled by a filter update algorithm 560 that updates filter coefficients after processing an out-of-band noise-detection imaging waveform that includes out-of-band noise, and optionally, a within-band noise detection imaging waveform that includes noise within the all or part of the imaging band. As in previous embodiments (FIG. 2B and FIG. 3B), as shown in FIG. 4, the input waveform is separately filtered with an imaging band pass filter 200 and a noise-detection band-pass filter 410, thereby generating an in-band imaging waveform 437 and at least one out-of-band noise-detection imaging waveform that includes out-of-band noise 438. The one or more out-of-band noise-detection imaging waveforms are processed by a filter-update algorithm at 560.

The filter-update algorithm analyzes the out-of-band noise and may evaluate signal characteristics, such as by performing a Fourier transform on a waveform array and identifying spectral maxima and the frequencies at which they occur. The filter update algorithm may use this information to control the coefficients of a dynamic digital filter that filters the imaging waveform at 550.

In one example implementation, the present method may be employed to reduce noise in a signal containing harmonic noise. For example, harmonic noise may be generated from a switching rectangular pulse source where, in frequency domain, the spacing of spectral lines is dependent on the pulse repetition frequency. If the pulse-width-modulation source generates noise that spans the 3-40 MHz band, where the imaging band lies within 7-13 MHz, and the dynamic filter 550 is a comb or multiple-notch filter, the filter update algorithm 560 may process signals from the noise-detection band (e.g. evaluate spectral line spacing and locations as seen in the 15-25 MHz range) and may use this information to control the stop bands in the dynamic in-band filter 550 to remove or reduce the harmonic noise.

In addition to out-of-band noise being used to update the dynamic filter, filter update algorithm 560 and/or dynamic filter 550 may optionally also probe the a within-band noise-detection imaging waveform to confirm the presence of in-band noise at one or more selected sub-bands within the imaging band prior to removing or reducing noise. For example, if the imaging band lies within 7-13 MHz and the filter update algorithm recognizes that there is harmonic noise at 15 MHz, 18 MHz, 21 MHz, 24 MHz and 24 MHz (integer multiples in the 15-25 MHz range), then the filter update algorithm may set the dynamic filter to filter out signals at 9 MHz and 12 MHz (integer multiples of 3 MHz within the imaging band). In one example implementation, such a filter may optionally only be applied if the presence of signal at 9 and 12 MHz is greater than expected relative to other signals within the imaging band are confirmed. In another example implementation, a noise characterization step may be performed, in the absence of imaging energy, to determine whether or not harmonic noise is present within the imaging band.

Embodiment 4: Noise Reduction Based on Pattern Recognition

Figure 7A:
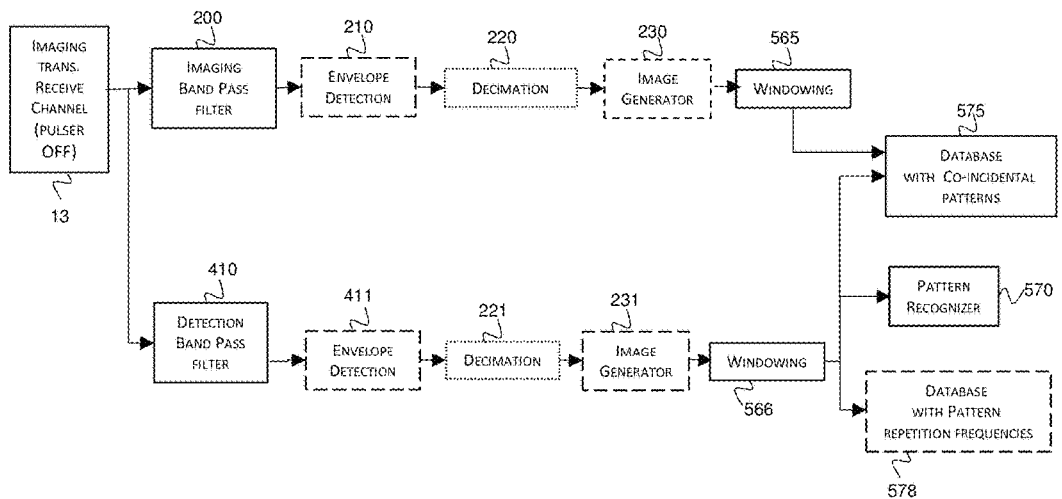
FIGS. 7A and 7B illustrate an example system configuration for noise reduction on an input waveform based on noise detected in one or more noise-detection waveforms, of which at least one noise-detection waveform comprises signal that is out-of-band from the imaging band. Different time windows of an in-band waveform undergo noise reduction according to one or more patterns identified by processing one or more noise-detection waveforms.
Figure 7B:
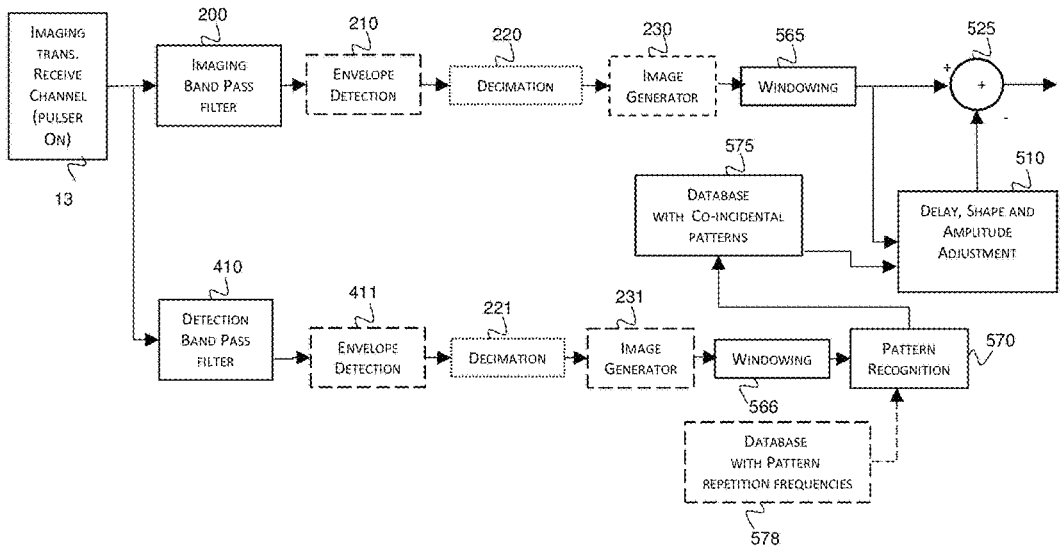

FIG. 7A and FIG. 7B illustrate an example embodiment of a noise correction method in which pattern recognition is employed to detect noise and to perform noise reduction on in-band imaging waveforms. In this example embodiment, matched sets of patterns in detection-band noise-characterization waveforms (at least one of which is lies, at least in part, outside the imaging band) and related in-band noise-characterization waveforms are initially identified during a noise characterization period in the absence of receiving imaging energy, as shown in FIG. 7A. Having correlated noise-detection patterns with in-band noise patterns via the noise characterization stage, these correlations may be employed during imaging to perform noise reduction of in-band imaging waveforms, based on the identification of patterns in the one or more detection-band imaging waveforms.

According to a first stage of the present example method, in a noise characterization stage, energy is detected within both an imaging band (in-band) and a noise-detection band in the absence of imaging energy (such as during a non-imaging noise characterization stage), thereby obtaining correlated measurements of in-band and detection-band noise-characterization waveforms. Samples from the in-band noise-characterization waveform and detection-band noise-characterization waveform are recorded as pairs of arrays, where an array pair refers to a sampled in-band waveform and a second corresponding sampled detection-band noise-detection waveform recorded at the same time.

The detection-band noise-characterization array and the in-band noise characterization array may be windowed at 566 and 565. The windows may be sliding windows, with optional overlap. Optionally, the windows may be centered around a peak noise amplitude, or be time-locked to a noise amplitude threshold. The windows may also be conditioned to reduce artifacts induced by windowing, such as by applying a window function, such as a Hamming window, Blackman window or other window functions well known in the art of signal processing. The array data (or windows thereof) may be processed to identify the presence of one or more noise patterns at 570.

Referring now to FIG. 7A, one or more detection-band noise-characterization arrays are processed to identify waveform patterns associated with patterns in the in-band noise-characterization waveforms. The pattern recognizer in step 570 extracts features from the detection-band characterization arrays and uses a predictive model to classify the features into noise 'classes'. The extracted features could be statistical features (including, but not limited to, variance, standard deviation, power, skewness, and kurtosis) in time domain, frequency domain (e.g. peak frequency), time-frequency domain (e.g. wavelet coefficients). The choice of features to be extracted may be made beforehand using feature selection algorithms such as forward selection or backward elimination methods.

Extracted features are fed to the predictive model in step 570, which may be trained to identify a pattern in a detection-band waveform and assign the pattern to a noise class. For example, machine learning methods may be used to train the predictive model to recognize patterns in the detection-band noise-characterization array using the extracted features. The predictive model may include an unsupervised learning model (such as k-means clustering), or a supervised learning model (such as a linear classifier, an artificial neural network or a nearest-neighbor classifier). Supervised learning may be used if prior information about noise sources are known, for example, the sources and sequence of the noise patterns may be known beforehand and noise class labels may be assigned to a waveform pattern in the detection-band noise-characterization waveform. The predictive model in step 570 may also accept as input class weights or a priori probabilities. The higher the a priori probability or weight of a class, the more likely it is to be recognized.

A database, shown in step 575 may store in-band noise-characterization waveform patterns that are known to be co-incidental with detection-band noise-characterization waveform patterns. For example, the database may store exemplary or average temporal in-band noise-characterization waveform patterns, paired with features of the co-incidental detection-band noise characterization patterns and noise class labels. The detection-band noise-characterization waveform patterns and their coincidental in-band noise-characterization waveform patterns may be determined on a per-window basis or otherwise. Further noise characterization may be performed in the temporal domain, or in the spatial domain after image generation at steps 230 and 231, in which case spatial features may also be extracted in step 570. The database may be of any suitable format used in computing, such a lookup tables.

Having correlated detection-band noise patterns with in-band waveform noise patterns via the noise characterization stage described above, these correlations may be employed during imaging to perform noise reduction of in-band imaging waveforms, based on the identification of patterns in the one or more detection-band imaging waveforms.

Referring to FIG. 7B, an in-band imaging waveform, is obtained by applying an imaging-band bandpass filter 200 to a waveform detected by an imaging transducer receive channel while the transducer is receiving imaging energy, and optionally performing envelope detection 210. A detection-band imaging waveform, is obtained by applying a noise-detection bandpass filter 410 to a waveform detected by an imaging transducer receive channel, and optionally performing envelope detection 411. The detection-band imaging waveforms and the in-band imaging waveforms may be windowed at 566 and 565, similar to the windowing step in the noise characterization stage. The waveforms may be sampled and represented as arrays.

Features may be extracted from the detection-band imaging array (or windows thereof), similar to the feature extraction step in the noise-characterization stage. Extracted features, and optionally class weights, are employed by the pattern recognizer 570, trained in the noise-characterization stage (described above), to identify the presence of one or more patterns in the detection-band imaging waveform.

The period (i.e. repetition frequency) of a noise pattern may be used to adjust the a priori probability of that pattern class (e.g. for a Bayes classifier) or to adjust the weight of that class (e.g. for a Support Vector Machine) while applying a pattern classification algorithm in 570. The higher the a priori probability or weight of a class, the more likely it is to be recognized. If the repetition interval of a pattern is known, the pattern is expected to be present at given times with a higher probability. The a priori probability or weight of that class could be adjusted to be higher at those times, increasing the likelihood that the pattern classifier will recognize that noise pattern. This repetition interval may be determined in the noise characterization stage and stored in a database 578, or may be loaded from a pre-stored database (local, networked, cloud storage).

Patterns in the detection-band imaging waveform that are identified in step 570 as being associated with one or more noise classes are then employed to generate noise corrections to the in-band imaging waveform (e.g. the in-band imaging array). These corrections may be generated based on finding a correlated in-band pattern in step 575, where matched sets of features of detection-band noise-characterization waveform patterns, in-band noise-characterization waveform patterns and noise class labels are stored in a searchable database or other classification scheme.

In the example method illustrated in FIG. 7B, an in-band noise correction is generated on a per-window basis, and subtracted from the in-band imaging waveform at 525, on a per-window basis, optionally after a delay and/or amplitude adjustment and/or shape adjustment 510 that temporally aligns the in-band noise pattern retrieved from the database 575 or other classification scheme with the in-band waveform.

In one example implementation, during a noise characterization stage (in the absence of receiving imaging energy), the detection-band noise-characterization array is first processed to extract one or more features which are then stored. The temporal intervals at which a given noise pattern is detected may also be determined at this stage and stored in 578. The corresponding correlated temporal pattern in the in-band noise-characterization array is also stored in 575 (for example, in a look-up-table).

According to the present example, during the imaging stage when noise removal is to be implemented, the detection-band imaging arrays for one or more detection-band imaging waveforms predominantly contain noise, and are processed via the same feature extraction process. A weight vector, which assigns weights (or a priori probabilities) for each class of noise patterns, may optionally be obtained. The repetition frequency of each pattern may be loaded from the database 578 created in a noise characterization stage or from a pre-stored database. The weight for each class may be adjusted dynamically so that it is dependent on that pattern's repetition frequency, the time instance when that pattern was previously detected, and the certainty with which that pattern was previously detected. Features extracted from the detection-band imaging waveform, and optionally class weights, are again fed to the trained predictive model (trained in the noise-characterization stage), which may identify a noise pattern in the detection-band imaging waveform and assign it a class. A corresponding and correlated in-band noise pattern for the noise class is then obtained from the database in 575, where, for example, in-band noise waveform patterns and features of detection-band waveform patterns for each noise class may be stored in during the noise characterization stage (e.g. in-band temporal waveforms stored in the look up table). The in-band noise waveform pattern extracted from the class comparison could be, for example, an average of all co-incidental in-band noise patterns for the current noise class, or the in-band noise pattern whose co-incidental detection-band pattern features are closest to the features of the current detection-band imaging array, for example, determined through a nearest-neighbour calculation. This co-incidental pattern is then subtracted from the input after amplitude and delay adjustment to obtain a noise reduced in-band imaging waveform.

FIG. 7A and FIG. 7B show an example implementation in which a single detection-band waveform (including energy residing, at least in part, beyond the imaging band) is generated by a single detection band pass filter 410 from which input to pattern recognizer 570 is derived. Alternatively, multiple detection-band waveforms may be generated by multiple detection band pass filters, of which at least one detection-band waveform is out-of-band.

In addition to the at least one detection-band waveform that carries out-of-band noise, one or more detection-band waveforms may carry noise within all or a portion of the imaging band (i.e. within-band noise-detection waveforms). Such within-band data may be useful for the pattern recognizer 570 to confirm that the noise predicted by the out-of-band noise-detection waveforms in fact exists in the imaging band (either during the noise characterization stage, or during imaging).

For example, within-band noise-detection imaging waveforms may also be employed by the pattern recognizer to identify a noise source. For example, if the energy in some sub-bands of the imaging band is substantially different relative to one or more other sub-bands of the imaging band, or relative to the net energy within the imaging band, then a noise source associated with the imaging sub-band may be identified. For example, a peak filter centered at 8 MHz may be used to obtain a within-band noise detection waveform within an imaging band ranging from 7 to 13 MHz, and a detection band-pass filter with a pass band of 15 to 25 MHz may be used to obtain an out-of-band noise-detection waveform. If the 8 MHz within-band noise-detection waveform detects an increase in energy relative to the energy in the out-of-band noise-detection waveform in the 15-25 MHz range, the pattern recognizer may be able to adjust its weights to preferentially detect a specific noise source (i.e. noise class). The system may better select a correlated in-band noise pattern from the database at 573 to remove that 8 MHz peak than if it solely relied on information that was out-of-band to the imaging band.

It will be understood that although the preceding example embodiments were disclosed within the context of detecting temporal patterns in raw or envelope-processed signals, the preceding algorithm may alternatively be adapted for implementation using image data. For example, image data (e.g. B-mode image data) may be processed to determine spatial noise patterns instead of processing time domain (e.g. RF or envelope-detected) signals. These alternative embodiments are shown with a dotted path in FIG. 7B, where decimation (220 and 221) and B-mode image line generation (230 and 231) is performed prior to 570 and 575.

Alternatively, when processing images in spatial domain, 2D imaging windows may be used to detect spatial patterns, such as for B-mode image data. For B-mode data, texture features may be extracted in the spatial domain (e.g. gray level co-occurrence matrices), frequency domain (e.g. Fourier spectrum measurements), or spatial frequency domain (e.g. energy of 2D wavelet coefficients).

Figure 7C:
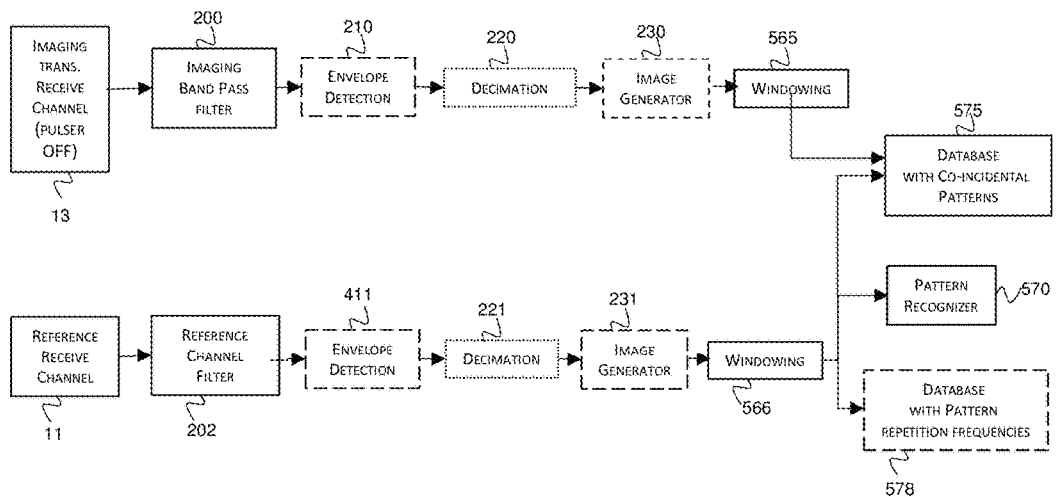
FIGS. 7C and 7D illustrate an example system configuration for reduction on an input waveform based on noise detected in a reference waveform, in which different time windows of an in-band imaging waveform undergo noise reduction according to one or more patterns identified by processing one or more reference waveforms.
Figure 7D:
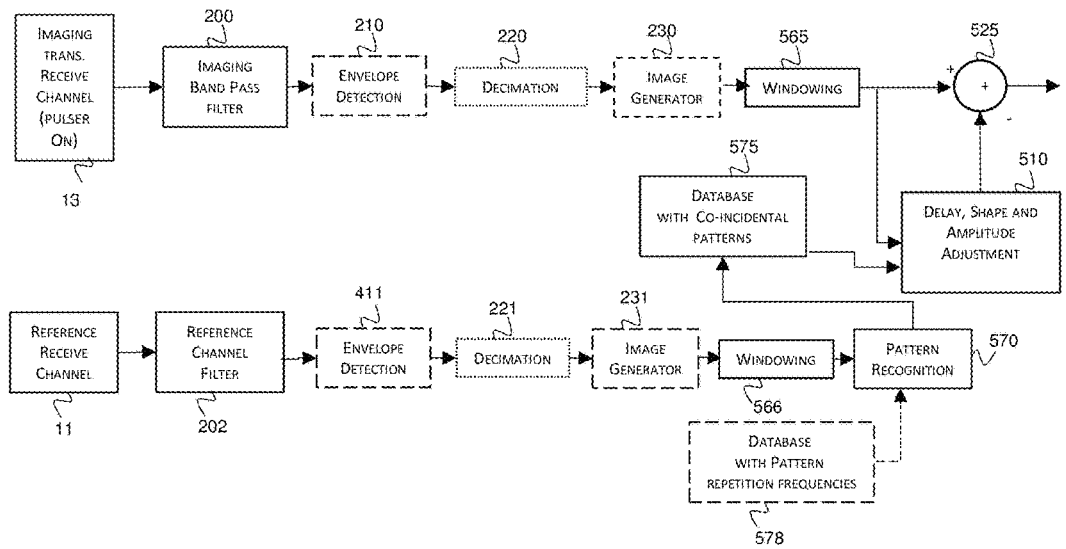

Referring now to FIG. 7D, an alternative example embodiment is shown in which a reference noise-detection waveform is employed, instead of the detection-band imaging waveform of FIG. 7B, when performing pattern recognition during imaging. Similarly, referring now to FIG. 7C, a reference noise-characterization waveform may be employed during the initial pattern recognition stage that is performed in the absence of imaging signal. The algorithms or schema described above, with reference to FIG. 7A and FIG. 7B, may thus be adapted to the present example embodiment by replacing the detection-band noise-characterization waveform (and associated array measures) with the reference noise-characterization waveform (shown in FIG. 7C), and replacing the detection-band imaging waveform (and associated array measures) with the reference noise-detection waveform (shown in FIG. 7D).

Embodiment 5: Noise Reduction Based on Relative Energy Measures

In the present example embodiment, noise reduction is performed by selectively attenuating a windowed portion of an in-band imaging waveform, based on criteria that are assessed according to measurements from one or more detection-band imaging waveforms, at least one of which is an out-of-band imaging waveform. Attenuating may refer, for example, to subtracting a derived subtrahend value from the envelope of the windowed in-band imaging waveform, and/or multiplying the windowed in-band imaging waveform or its envelope with an attenuation factor, where the subtrahend value and/or the attenuating factor are determined from measurements on the noise-detection imaging waveforms or reference noise-detection waveforms.

According to a first stage of the present example method, in a noise characterization stage, energy is detected within both an imaging band (in-band) and a noise-detection band in the absence of imaging energy (such as during a non-imaging noise characterization stage), thereby obtaining correlated measurements of in-band noise and detection-band noise. At least one noise-detection band is out-of-band. Samples from the in-band noise-characterization waveform and the detection-band noise-characterization waveform are recorded as pairs of arrays, where an array pair refers to a sampled in-band waveform and a second corresponding sampled detection-band waveform recorded at the same time.

Figure 6A:
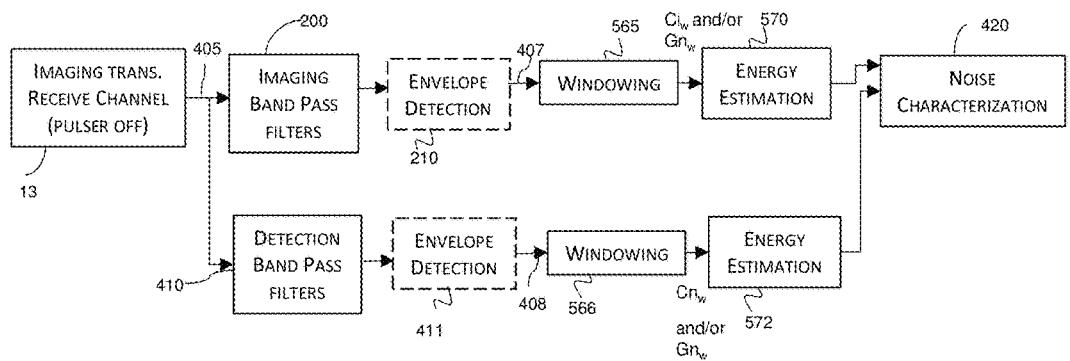
FIGS. 6A and 6C illustrate example system configurations for noise reduction on an input waveform based on detection of noise in an out-of-band waveform, in which different time windows of an in-band waveform are suppressed, based on the processing of a respective window of an out-of-band waveform, and where noise windows of the in-band waveform are corrected by subtracting with a subtrahend value dependent on the amount of power within the window of the out-of-band waveform.

Optionally, the noise characterization stage may include an additional stage, referred to as a baseline noise characterization stage, when it is either known or anticipated that the imaging transducer receive circuit is not receiving imaging energy and not receiving noise energy. As shown in FIG. 6A, an in-band baseline noise characterization array may be obtained by applying an imaging band pass filter 200 to an input waveform detected from an imaging transducer receive channel 13 in the absence of receiving imaging energy and in the absence of receiving noise energy, and optionally detecting an envelope of the filtered waveform at 210. A detection-band baseline noise-characterization array may be obtained by applying a detection-band filter 410 to an input waveform from an imaging transducer receive channel 13, and optionally detecting an envelope of the filtered waveform at 411. The in-band baseline noise characterization array and the detection-band baseline noise-characterization array, measured in the absence of imaging energy and absence of noise energy, are denoted as Gi and Gn, respectively. A given array pair may optionally be segmented according to a plurality of time windows, as illustrated in FIG. 6A at 565 and 566, to obtain windowed array pairs, denoted as $Gi_w$ and $Gn_w$. The windows may be sliding windows, with optional overlap between adjacent windows. One or more noise measurements may be calculated from the per-window energy measurements in a baseline noise characterization stage. For example, the maximum power within a windowed in-band baseline noise-characterization array may be denoted as Ti. Similarly, the maximum power within a windowed out-of-band baseline noise characterization array may be denoted as Tn.

The noise characterization stage includes a stage when the imaging transducer receive circuit is not receiving imaging energy but is anticipated to receive noise energy. Referring again to FIG. 6A, an in-band noise characterization array 407 may be obtained by applying an imaging band pass filter 200 to an input waveform detected from an imaging transducer receive channel 13 in the absence of receiving imaging energy, and optionally detecting an envelope of the filtered waveform at 210. A detection-band noise-characterization array may be obtained by applying a noise-detection band filter 410 to an input waveform from an imaging transducer receive channel 13, and optionally detecting an envelope of the filtered waveform at 411. The in-band noise characterization array 407, and the -detection-band noise characterization array 408, measured in the absence of imaging energy, are denoted as Ci and Cn, respectively (as shown in FIG. 6A).

A given array pair may optionally be segmented according to a plurality of time windows, as illustrated in FIG. 6A at 565 and 566, to obtain windowed array pairs, denoted as $Ci_w$ and $Cn_w$. The windows may be sliding windows, with optional overlap between adjacent windows. In another example, the windows may be centered around a peak amplitude of the noise waveforms in one or more detection bands and/or in the imaging band. In yet another example, the time windows may be time-locked to noise onsets determined when the amplitude of noise in one or more detection bands and/or the imaging band exceeds predefined thresholds. For example, the threshold may be proportional to parameters Tn and/or Ti obtained during a baseline noise characterization stage.

The in-band and detection-band noise-characterization array pairs $Ci_w$ and $Cn_w$ are processed to obtain one or more measures associated with the energy in the imaging band and a noise-detection band for each time window, in order to characterize the relative intensity of the noise within the two bands. For example, as shown in FIG. 6A, for each pair of windows $Ci_w$ and $Cn_w$ the power in the imaging band and the power in the noise-detection-band may be calculated at 570 and 572.

Figure 6B:
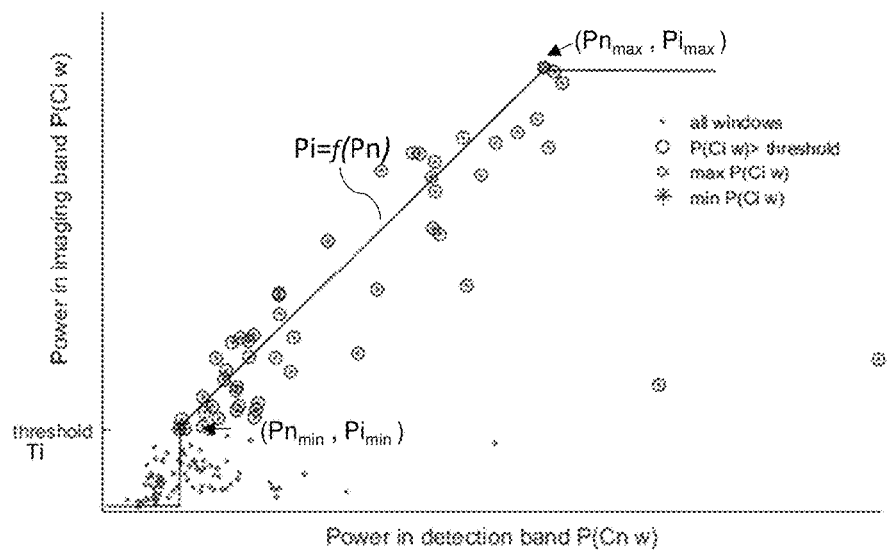
FIG. 6B illustrates an example scatter plot showing signal power of windows of an in-band waveform versus signal power of respective windows of an out-of-band waveform in a noise characterization stage.

Noise-characterizing measurements may optionally be calculated only from select windows, where selection criteria may be assessed according to in-band energy measurements, and optionally detection-band energy measurements. For example, only windows for which the in-band power exceeds a predefined threshold may be selected for obtaining noise-characterizing measurements, as shown in FIG. 6B. The threshold may be proportional to Ti obtained during a baseline noise characterization stage. In another example, only windows for which the out-of-band power exceeds a predefined threshold may be selected for obtaining noise-characterizing measurements. The threshold may be derived from Tn obtained during a baseline noise characterization stage.

It is to be understood that, in the proceeding examples, maximum and minimum values may refer to either upper and lower percentiles, or true maximum and minimum values. For example, $98^{th}$ and $2^{nd}$ percentiles values may be used instead of the maximum and minimum values. Other statistical thresholds, such as the $95^{th}$ and $5^{th}$ percentiles, $90^{th}$ and $10^{th}$ percentiles and $80^{th}$ and $20^{th}$ percentiles or others may be used to represent the maximum and minimum values for characterization purposes.

One or more noise measurements may be calculated from the per-window energy measurements in a noise characterization stage, and may be used to define a relationship between power in the imaging band and power in the detection band in the presence of a noise source. For example, one or more pairs of in-band and detection-band power values may be selected as inflection points for generating a piece-wise linear function to define the relationship between power in the imaging band and power in the detection band in the presence of a noise source, as shown in FIG. 6B.

In one example, a piece-wise linear function defining the relationship between the in-band power and the detection-band power in the presence of a noise source may be generated based on maximum and minimum power values obtained in a noise characterization stage, as shown in FIG. 6B. Minimum and maximum in-band power values from a noise characterization stage may be evaluated (e.g. as absolute maximum/minimum values or using statistical measures) and denoted as $Pi_{min}$ and $Pi_{max}$, respectively. In one example implementation, a set of windows whose in-band power falls within a preselected range relative to $Pi_{min}$ (e.g. within a percentile range) may be identified, and, from among the identified set of windows, the minimum detection-band power may be selected as $Pn_{min}$. Similarly, a set of windows whose in-band power falls within a preselected range relative to $Pi_{max}$ may be identified, and, from among the identified set of windows, the minimum detection-band power may be selected as $Pn_{max}$. Power pairs ($Pn_{min}$, $Pi_{min}$) and ($Pn_{max}$, $Pi_{max}$) may be used for the fitting of a function defining an estimated relationship between in-band and detection-band power. It is to be understood that the example implementation is just one non-limiting example of selecting values of in-band and detection-band powers to provide suitable fitting points and/or a functional relationship between in-band and detection-band power, and other methods may be alternatively employed.

Optionally, the ratio of the power in the in-band noise-characterization waveform to the power in the detection-band noise-characterization waveform may be calculated on a per-window basis, and the maximum ratio $R^{off}$ across a plurality of windows (an example use of this quantity is described below when determining whether or not to apply a noise correction during imaging) may be obtained.

One or more relationships f(Pn) between the power in the in-band noise-characterization waveform (Pi) and power in the detection-band noise-characterization waveform (Pn) may be obtained. For example, as shown in FIG. 6B, f(Pn) may be a piece-wise linear function whose slope, intercept and/or inflection points are defined by the points ($Pn_{min}$, $Pi_{min}$) and ($Pn_{max}$, $Pi_{max}$) calculated in a noise characterization stage. In another example f(Pn) may be a non-linear polynomial, or a combination of one or more linear or non-linear polynomials. In yet another example, f( ) may be a set of values defined for one or more ranges of Pn values. For example, f(Pn) may be assigned a value $Pi_a$ for $a_1 \leq Pn < a_2$, f(Pn) may be assigned a value $Pi_b$ for $b_1 \leq Pn < b_2$ and so forth, where $[a_1, a_2]$ and $[b_1, b_2]$, and so forth, are non-overlapping intervals of Pn. A set of windows of the detection-band noise characterization array whose power lies between $a_1$ and $a_2$ may be identified, and the associated windows of the in-band noise characterization array may be employed to determine a value for $Pi_a$ for the interval $[a_1, a_2]$. For example, $Pi_a$ may be a representative power value (such as maximum, mean, median or some other measure) calculated from in-band power measurements of all windows whose detection-band power, Pn, lies within the range $[a_1, a_2]$.

Figure 6C:
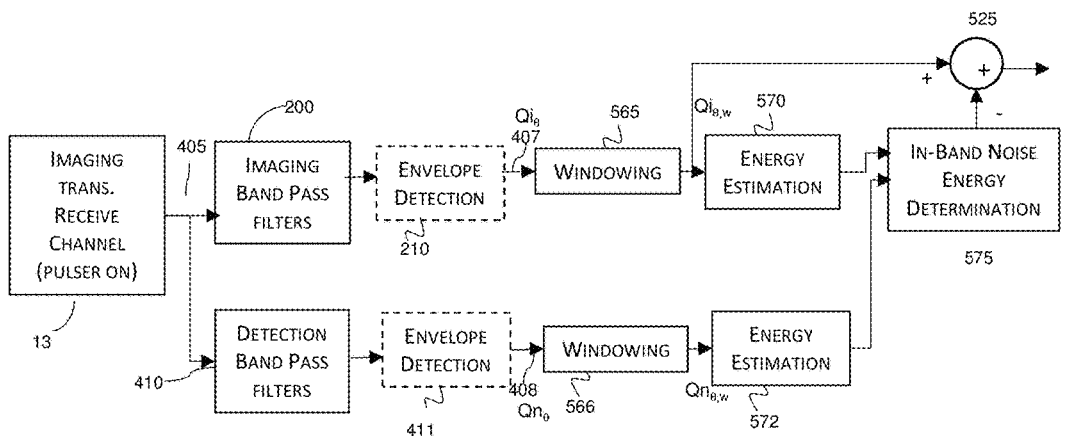
Figure 6D:
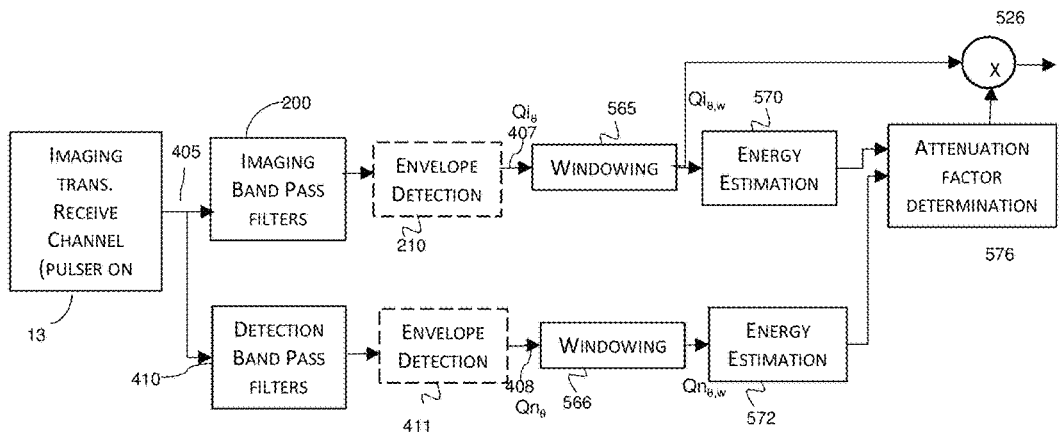
FIG. 6D illustrates an example system configuration for noise reduction on an input waveform based on detection of noise in an out-of-band waveform, in which different time windows of an in-band waveform are suppressed, based on the processing of a respective window of an out-of-band waveform, and where noise windows of the in-band waveform are corrected by multiplication with an attenuation factor dependent on the amount of power within the window of the out-of-band waveform.

Noise measurements obtained in a noise characterization stage may be employed to perform noise reduction of the in-band imaging waveform obtained during imaging, as shown in FIG. 6C and FIG. 6D. The input waveforms, filtered as shown at 200 and 410 to provide the in-band imaging waveform 407 and the detection-band imaging waveform 408, optionally after envelope detection at 210 and 411. The waveforms may be sampled to obtain in-band imaging arrays and detection-band imaging arrays.

In the present example embodiments, the term "in-band imaging array" is employed to refer to a sampled in-band imaging waveform. The term "detection-band imaging array" is employed to refer to a sampled detection-band imaging waveform. A set of arrays may be recorded, where each array may be respectively associated with a given scan line. For example, a first in-band imaging array may be associated with a first scan line, a second in-band imaging array may be associated with a second scan line, and so forth. The in-band and detection-band imaging arrays are denoted as $Qi_\theta$, and $Qn_\theta$, respectively, where $\theta$ is an index identifying a given period of acquisition, such as one corresponding to a scan line.

The arrays may be windowed, as shown at 565 and 566 in FIG. 6C, such as using the same window properties as those employed to window the noise characterization arrays in the characterization stage. The in-band imaging arrays and detection-band imaging arrays, temporally segmented according to the windows, are denoted as $Qi_{\theta,w}$ and $Qn_{\theta,w}$, respectively, where the subscript w is an integer denoting the window number. For example, $Qi_{1,10}$ refers to the $10^{th}$ window portion of the in-band imaging array corresponding to the $1^{st}$ scan line. For each windowed portion of the in-band imaging array and the detection-band imaging array, power or another suitable energy measurement may be calculated, as shown at 570 and 572. In-band and detection-band power values, on a per-window basis, are calculated as $P(Qi_{\theta,w})$ and $P(Qn_{\theta,w})$, respectively. These energy measurements may then be used for suppressing noise based on measurements obtained in a noise characterization stage.

In one example implementation, shown in FIG. 6C, noise may be suppressed by subtracting a power value from the envelope of the in-band imaging array $Qi_{\theta,w}$ at 525. Noise-detection band power $P(Qn_{\theta,w})$, may be used to estimate a noise energy, $\hat{P}i_{N\theta,w}$, within the in-band imaging array window $Qi_{\theta,w}$ based on the function ( ) obtained in a noise characterization stage. For example, the noise energy $\hat{P}i_{N\theta,w}$ within $Qi_{\theta,w}$ may be estimated at 575 as $\hat{P}i_{N\theta,w}=f(P(Qn_{\theta,w}))$. The estimated in-band noise $\hat{P}i_{N\theta,w}$ may optionally be scaled by multiplication with a scaling factor $\beta$, where $0 \leq \beta \leq 1$. The scaled estimated noise $\beta\hat{P}i_{N,w}$ may optionally be clamped below an upper limit, such as, but not limited to $0.8 \times P(Qi_{\theta,w})$, $0.9 \times P(Qi_{\theta,w})$ or $1 \times P(Qi_{\theta,w})$ to obtain a subtrahend value. The subtrahend value may be subtracted from the envelope of $Qi_{\theta,w}$ at 525 to obtain a noise reduced waveform envelope.

In another example implementation shown in FIG. 6D, noise may be suppressed by multiplying the elements of the in-band imaging array $Qi_{\theta,w}$ by an attenuating factor at 526. During imaging, the in-band power in an imaging window $Qi_{\theta,w}$ may be calculated as $P(Qi_{\theta,w})$. Noise-detection band power $P(Qn_{\theta,w})$, may be used to estimate a noise energy, $\hat{P}i_{N\theta,w}$, within the in-band imaging window $Qi_{\theta,w}$ based on the function f( ) obtained in a noise characterization stage. For example, the noise energy $\hat{P}i_{N\theta,w}$ within $Qi_{\theta,w}$ may be estimated at 575 as $\hat{P}i_{N\theta,w}=f(P(Qn_{\theta,w}))$. The estimated in-band noise $\hat{P}i_{N\theta,w}$ may optionally be scaled by multiplication with a scaling factor $\beta$, where $0 \leq \beta \leq 1$. An attenuating factor may be selected to be proportional to $[P(Qi_{\theta,w})-\beta\hat{P}i_{N\theta,w}]/P(Qi_{\theta,w})$.

In some example implementations, scaling factor $\beta$ may be selected to lie between zero and unity. In ultrasound, where attenuation of ultrasound energy causes the imaging energy to be reduced over time, the determination of $\beta$ may be dependent on the depth of the window within the waveform (thus corresponding to a depth within the imaged tissue). The parameter $\beta$ may optionally be user-controlled. The attenuating factor may optionally be clamped below an upper limit, such as, but not limited to, unity, 0.95, 0.9, or 0.8. The attenuating factor may additionally or alternatively be clamped above a lower limit, such as, but not limited to, 0, 0.01, 0.05, or 0.1. The attenuating factor may be multiplied with the array $Qi_{\theta,w}$ at 526 or its envelope to obtain a noise reduced array.

Pattern Recognition for Class-Specific Noise Reduction

During a noise characterization stage (see, for example, FIG. 6A), the system may optionally be configured to group array pairs $Cn_w$ and $Ci_w$ into one or more categories, referred to as classes. Referring back to the pattern recognizer described in step 570 of FIG. 7A, one or more detection-band noise-characterization waveforms may be processed by a pattern recognizer in order to identify one or more classes of noise patterns and to assign a class to temporal windows associated with an identified noise pattern. A set of windows of the detection-band noise-characterization waveform belonging to a class k may be selected and denoted as $\{w\_k\}$. In-band and out-of-band power measures for windows within set $\{w\_k\}$ may be used to derive a functional relationship $f_k(\ )$ specific to the class k, using methods similar to those described in the preceding paragraphs.

The system may be configured to employ a pattern recognizer to identify noise patterns when the imaging transducer circuit is receiving imaging energy. Using methods similar to those described for step 570 of FIG. 7B, one or more detection-band imaging waveforms may be processed by a pattern recognizer in order to identify one or more classes of noise patterns and to assign a class to temporal windows associated with an identified noise pattern. The estimated in-band noise power may be derived from a functional relationship f( ) specific to the identified class. For example, for windows belonging to class 1, function $f_1(\ )$ may be used to derive an estimated in-band noise (i.e. $\hat{P}i_{N\theta,w}=f_1(P(Qn_{\theta,w}))$). Similarly, for windows belonging to class 2 function $f_2(\ )$ may be used to derive an estimated in-band noise, and so forth, where $f_1(\ )$, $f_2(\ )$, $f_3(\ )$, etc. are obtained in a noise characterization stage. As described previously, noise in a given window $Qi_{\theta,w}$ of the in-band imaging waveform may be reduced by subtracting a subtrahend value from the envelope of $Qi_{\theta,w}$, or by multiplying $Qi_{\theta,w}$ with an attenuation factor, where the subtrahend value or the attenuation factor are derived from $\hat{P}i_{N\theta,w}$. As a further specific example, noise classified by the pattern recognizer as class 1 may originate from an electroanatomic mapping system and noise classified as class 2 may originate from an ablation energy generator. Therefore, $f_1(\ )$ could be used to estimate the in-band noise generated by the electroanatomic mapping system based on the power in the noise-detection band when the noise is recognized by the system to come from the mapping system, and $f_2(\ )$ could be used to estimate the in-band noise generated by the ablation generator based on the power in the noise-detection band when the noise is recognized by the system to come from the ablation generator.

In another example, systems that emanate noise may be monitored to determine which functional relationship to use for noise estimation and suppression. For example, the controls of an ablation generator may be monitored so that a binary gating signal is enabled when the ablation generator is actively generating energy (and associated noise). This gating signal may be used to determine the time periods when function $f_2(\ )$ is to be used for in-band noise estimation.

Selectively Performing Noise Reduction

Energy measurements may optionally be employed to estimate whether or not the in-band imaging array is likely to exhibit a low signal-to-noise ratio. In other words, energy measurements may be employed to classify windows as to whether or not to apply a noise reduction correction (via subtraction or multiplication with an attenuating factor).

In one example implementation, the decision about whether or not to apply a noise reduction correction for a given window, w, can be made based on the power detected in the noise-detection band. Noise correction is applied for $Qi_{\theta,w}$ if $P(Qn_{\theta,w})$ exceeds a predefined threshold. The threshold may be obtained in a noise characterization stage.

In other instances the decision about whether or not to apply a noise reduction correction for a given window can be made based on ratio of the power in the imaging band relative to the power in the noise-detection band. For example, in a noise-characterization stage, for each window of the pairs of in-band noise-characterization arrays and detection-band noise-characterization arrays, the ratio of the power in the imaging band to the power in the detection band may be obtained. The representative maximum ratio across all windows, denoted $R^{Off}$, may be used as a threshold to decide whether or not to apply noise reduction correction when the imaging transducer receive circuit is receiving imaging energy, as described below.

The decision about whether or not to apply a noise reduction correction for a given window, w, of an in-band imaging waveform can be made based on ratio of the power in the imaging band relative to the power in the noise-detection band, denoted as $R^{ON}_w$. In one example implementation, $R^{On}_w$ is compared to $\gamma R^{Off}$, where $\gamma$ is a relaxation parameter and $R^{Off}$ is the representative maximum ratio calculated in a noise characterization stage. If $R^{On}_w$ is determined to be greater than $\gamma R^{Off}$, then it is estimated that the signal-to-noise ratio of the in-band signal is sufficiently high and a noise reducing correction is not applied. Conversely, if $R^{On}_w$ is determined to be less than or equal to $\gamma R^{Off}$, then it is estimated that the signal-to-noise is sufficiently low to warrant the application of a noise reduction correction.

The value of $\gamma$ may be employed to adjust the sensitivity to signal-to-noise, and may be used, in some cases, as an adjustment factor for cases in which weak portions of the signal would otherwise be suppressed. Lowering the value of $\gamma$ will lower the threshold for applying noise reduction, thereby reducing the number of windows that undergo noise reduction and allowing more imaging energy (and noise) to persist in the final output.

In some example implementations, $\gamma$ may be selected to lie between zero and unity. In ultrasound, where attenuation of ultrasound energy causes the imaging energy to be reduced over time, the determination of $\gamma$ may be dependent on the depth of the window within the waveform (thus corresponding to a depth within the imaged tissue). The parameter $\gamma$ may optionally be user-controlled. For example, in cases in which tissue or other structural aspects of the image are perceived to be unnecessarily or overly attenuated, the user can reduce the value of this parameter in order to lessen the effect of noise reduction.

For windows that are identified for noise reduction, any suitable noise reduction or suppression method may be employed to reduce noise of the in-band imaging array within the window. It will be understood that a wide variety of noise reduction corrections may be applied, such as, but not limited to, corrections involving subtraction as shown in FIG. 6C and/or multiplication with an attenuation factor as shown in FIG. 6D.

In some cases, the noise suppression can cause erroneous noise reduction on a per-window basis. For example, some windows that contain a small amount of imaging energy may inadvertently undergo noise reduction based on an erroneous determination of a low signal-to-noise ratio in a window (i.e. false window classification). This can result in some small image "holes" in a surrounding homogenous signal region of an image, or residual noise pixels in a surrounding low-noise region of an image. In one example embodiment, the status of adjacent windows (i.e. windows in the spatial neighborhood) may be employed to determine whether or not a window that is identified as being suitable for noise reduction should in fact undergo such a process. If a given window is identified as being suitable for noise reduction as per the aforementioned methods, then adjacent windows in one or more adjacent arrays (i.e. arrays corresponding to adjacent scan lines) may be employed to assess whether or not noise reduction by amplitude attenuation of the given window should be performed.

For example, if, for a given scan line, a given window is identified as not being suitable for noise reduction, yet one or more adjacent windows are identified as being suitable for noise reduction, the window may be flagged as being likely misclassified. The status of the given window may be overridden and the given window may instead by identified as being suitable for noise reduction, such that noise reduction is applied to the given window. Conversely, if a given window is identified as being suitable for noise reduction, yet adjacent windows within adjacent arrays are identified as not being suitable for noise reduction, then the initial determination of the status of the given window may be overridden such that the given window is instead identified as not being suitable for noise reduction and is flagged as a window that is likely misclassified. Samples of misclassified windows may be replaced by samples of one or more non-noisy neighboring windows (i.e. replaced by or interpolated from samples of adjacent windows identified as not being suitable for noise reduction as per the aforementioned methods) optionally after performing delay and amplitude adjustments.

An example implementation of this method is illustrated in FIG. 6E, where adjacent windows in adjacent arrays are interrogated to determine whether or not the classification of the current window is consistent with its surrounding windows in adjacent arrays. Since two windows (array 2, windows 4 and 5) classified as containing primarily noise (marked "N") are surrounded by windows (marked "S") classified as having a sufficiently high signal power to avoid the need for noise reduction, the two "N" windows may be replaced with samples from neighboring "S" windows (for example, by copying or by interpolating with amplitude adjustment and/or shape adjustment), and noise reduction by noise estimation will not be performed on these windows, as shown in FIG. 6F. Although the present example implementation employs two adjacent windows on either side of the array when confirming the status of a given window, other embodiments may employ any number of adjacent windows.

One or more temporally adjacent windows before and after a given window may also be employed when assessing whether the classification of a given window should be altered. For example, in FIG. 6E, window 4 of array 5, initially marked "S", may be reclassified as "N", shown in FIG. 6F, since preceding and proceeding windows of the array are marked "N".

Although the present example embodiment involves the processing of signals prior to image processing, the present example embodiment may be adapted to process image data as opposed to the processing of time-domain signals. For example, a plurality of in-band and detection-band imaging arrays, representing a plurality of adjacent scan lines, may be acquired and post-processed to obtain in-band image and detection-band image frames. The in-band and detection-band image pixels are denoted as $Bi_{\theta,d}$ and $Bn_{\theta,d}$, respectively, where $\theta$ is denotes a scan line and d is the depth. The detection-band image may be used to evaluate attenuation (i.e. via subtraction or multiplication) values for each pixel in the in-band image. These attenuation values may be obtained from a corresponding pixel in a detection-band image on a per-pixel basis (i.e. the value at $Bn_{\theta,d}$ may be used to attenuate the pixel intensity at $Bi_{\theta,d}$) or by processing a region-of-interest in the detection-band image that would correspond to a local spatial neighborhood of an in-band image pixel (e.g. the values of a 3×3 neighborhood (e.g. in polar or Cartesian co-ordinates) around $Bn_{\theta,d}$ may be used to attenuate the pixel intensity at $Bi_{\theta,d}$).

Figure 6G:
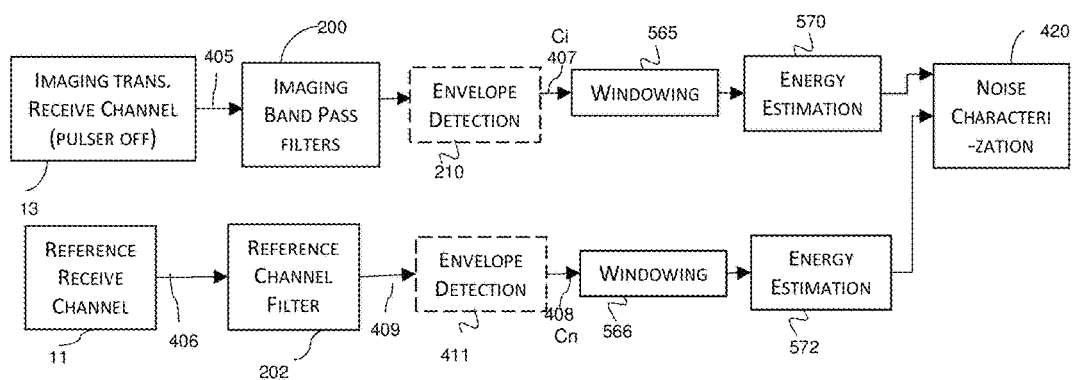
FIGS. 6G and 6H illustrate an example system configuration for noise reduction on an input waveform based on detection of noise in a filtered reference waveform measured with a reference receive channel, in which different time windows of an in-band waveform are suppressed, based on the processing of a respective window of a reference waveform, and where noise windows of the in-band waveform are corrected by subtracting with a subtrahend value dependent on the amount of power within the window of the filtered reference waveform.
Figure 6H:
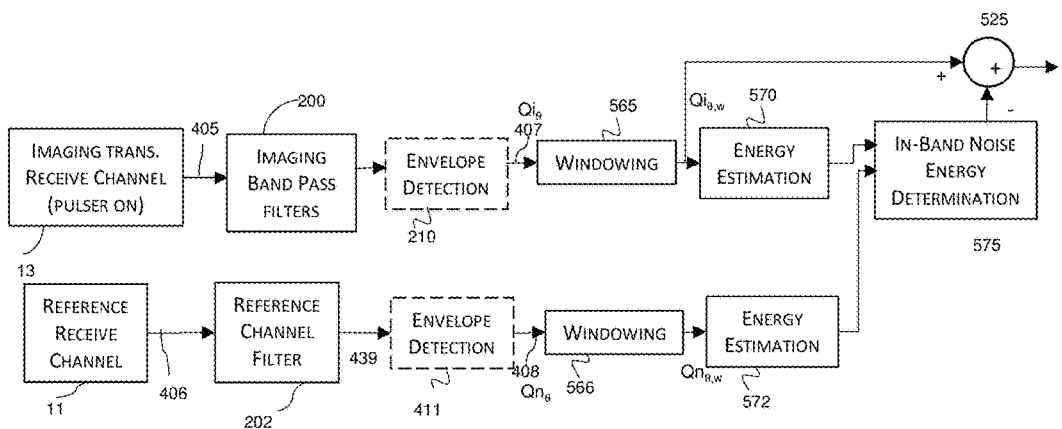
Figure 6I:
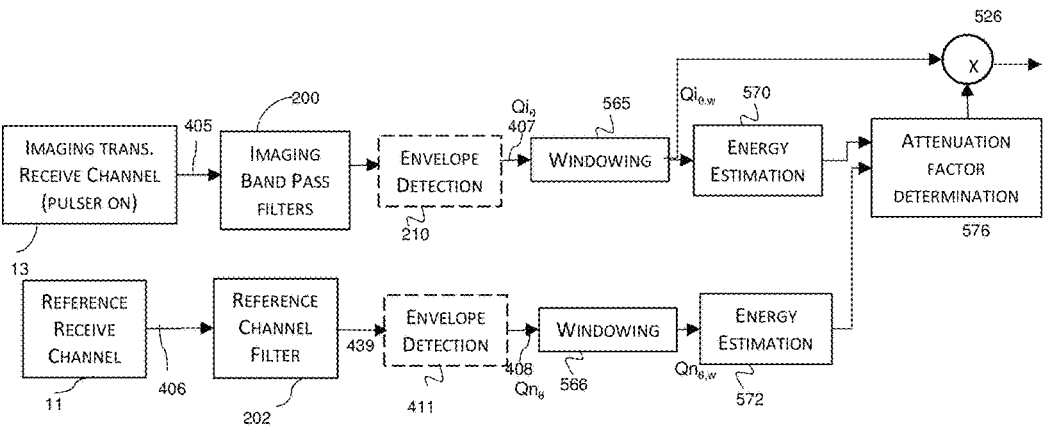
FIG. 6I illustrates an example system configuration for noise reduction on an input waveform based on noise measured in a filtered reference waveform measured with a reference receive channel, in which different time windows of an in-band imaging waveform are corrected, based on the processing of a respective window of the filtered reference waveform, and where noise windows of the in-band imaging waveform are corrected by an attenuation factor dependent on the amount of power within the window of the filtered reference waveform.

Referring now to FIGS. 6G, 6H and 6J, alternative example embodiments are shown in which a reference receive channel is used when performing noise characterization (FIG. 6G) and for the determination of a suitable subtrahend value (FIG. 6H) or attenuation factor (FIG. 6J) for noise suppression during imaging. In FIG. 6G, a reference noise characterization waveform 409 is employed, instead of the detection-band noise characterization waveform of FIG. 6A, when performing noise characterization. The reference channel filter could be an imaging band pass filter. Alternatively, if the noise estimation benefits from input of out-of-band noise, then the reference channel filter may be different from an imaging band pass filter. In FIG. 6H, a reference noise-detection waveform 439 is employed, instead of the detection-band imaging waveform of FIG. 6B, to determine subtrahend values and apply a noise reduction by subtraction. Similarly, in FIG. 6I, a reference noise-detection waveform 439 is employed, instead of the detection-band imaging waveform of FIG. 6B, to determine and apply an attenuation factor for noise reduction. The methods described above, with reference to FIGS. 6A to 6F, may thus be adapted to the present example embodiment by replacing the detection-band noise-characterization waveform 408 (and associated power measures) with the reference noise-characterization waveform 409 shown in FIG. 6G, and replacing the detection-band imaging waveform 438 (and associated array and power measures) with the reference noise-detection waveform 439 shown in FIG. 6H and FIG. 6I.

Embodiment 6: Noise Reduction of Pseudo-Periodic Noise Sources

In the present example embodiment, noise reduction is performed by estimating and subtracting in-band noise, where the noise is expected to originate from a pseudo-periodic noise source or a pseudo-periodic sequence of noise sources. The in-band noise is estimated based on measurements made during a noise characterization stage when an imaging transducer receive circuit is not receiving imaging energy.

According to a first stage of the present example method, waveforms are detected within both an imaging band and a noise-detection band in the absence of imaging energy (e.g. when an ultrasound transducer is not receiving imaging energy) and sampled, thereby obtaining a pair of co-incidental in-band and detection-band (out-of-band) noise characterization arrays.

Figure 8A:
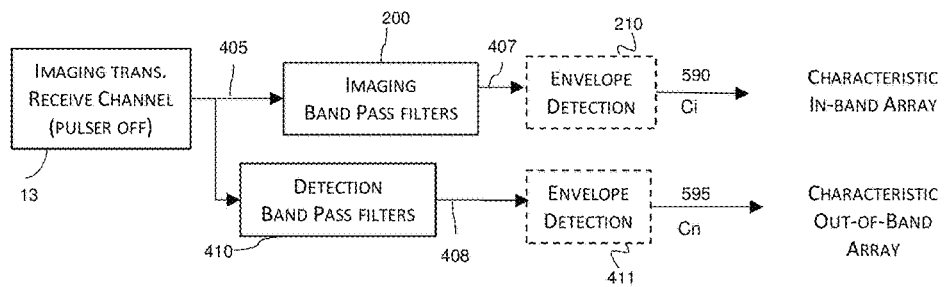
FIGS. 8A and 8B illustrate an example system configuration for noise reduction on an input waveform based on noise detected in an out-of-band waveform, in which different time windows of an in-band waveform undergo noise reduction according to the estimated in-band noise that is temporally aligned prior to reduction.

As shown in FIG. 8A, an in-band noise-characterization waveform 590 may be obtained by applying an imaging band pass filter 200 to an input waveform detected from an imaging transducer receive channel 13, and optionally detecting an envelope 210 of the filtered data. A detection-band noise-characterization waveform 595 may be obtained by applying a noise-detection bandpass filter 410 to an input waveform from an imaging transducer receive channel (where at least one noise-detection band comprises signal from outside of the imaging band), and optionally detecting an envelope 411 of the filtered data. The in-band noise-characterization waveforms and detection-band noise characterization waveforms, measured in the absence of imaging energy, may be sampled to obtain in-band noise-characterization arrays and detection-band noise characterization arrays, denoted as Ci and Cn, respectively. Ci (and Cn) should capture one or more periods of a periodic noise source.

Having obtained the in-band and detection-band noise characterization arrays in a noise characterization stage, the correlation between the detection-band characterization array and a detection-band imaging array may be used to estimate adjustment parameters for subtracting the in-band characterization array from the in-band imaging array.

Figure 8B:
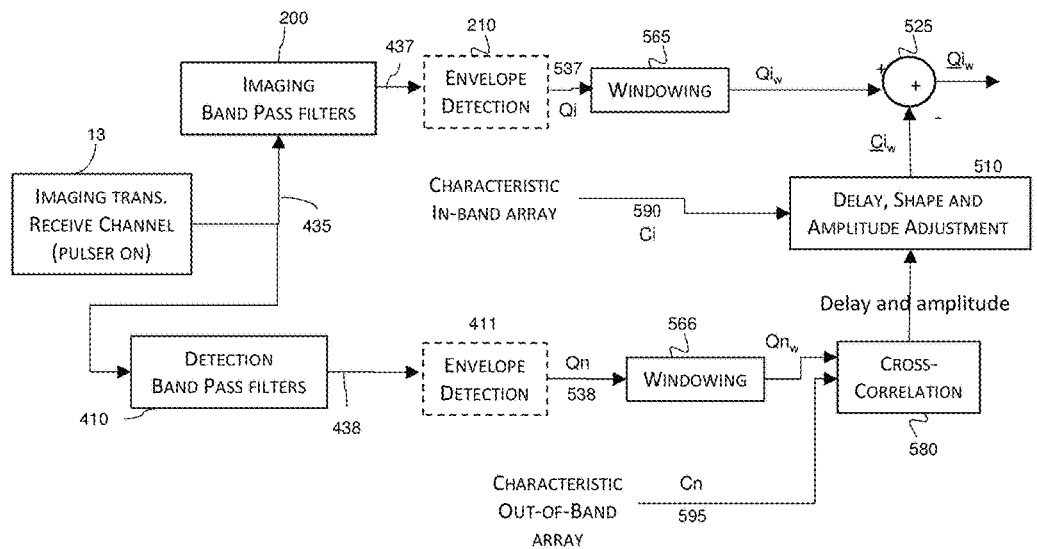

As shown in FIG. 8B, when performing imaging, the input waveforms from an imaging transducer receive circuit 13 are filtered as shown at 200 and 410 to provide in-band imaging waveforms and detection-band imaging waveforms. These waveforms may be sampled (before or after performing envelope detection) to obtain an in-band imaging array 537 and a detection-band imaging array 538. The in-band and detection-band imaging arrays are denoted as Qi and Qn, respectively.

According to the present method, each in-band imaging array is processed for noise reduction using the in-band noise-characterization array Ci to subtract noise from the in-band imaging array Qi. However, in order to perform noise reduction via subtraction, the in-band noise characterization array Ci should be temporally aligned with the in-band imaging array Qi such that noise is co-incidental. Such alignment is possible in the case of a periodic noise source that generates noise in the imaging band that is correlated with noise in a noise-detection-band.

The temporal alignment may be achieved, for example, by segmenting the in-band and -detection-band imaging arrays Qi and Qn into a plurality of time windows at 565 and 566 (as described in the preceding example embodiments). The windows should preferably be long enough to capture one or more periods of the periodic noise source. The imaging arrays, temporally segmented according to the windows, are denoted as $Qi_w$ and $Qn_w$, where the subscript w is an integer denoting the window number.

In one example embodiment, temporal alignment may be achieved on a per-window basis. In the present example implementation, the temporal alignment may be achieved by calculating, within each window, the cross-correlation between the detection-band noise characterization array Cn and the detection-band imaging array $Qn_w$, and selecting the relative time delay $\tau$ corresponding to the maximum cross-correlation, as shown at 580. Due to the co-incidental relation between the noise in the imaging band and noise in the noise-detection band, this time delay $\tau$ can also be applied to align the in-band noise characterization array Ci relative to the in-band imaging array $Qi_w$, on a per-window basis as shown at 510. A scaling factor may also be applied to the aligned in-band noise characterization array.

A windowed portion of the aligned in-band noise characterization array which is denoted by $\underline{Ci}_w$, is then subtracted from the in-band imaging array $Qi_w$, resulting in a noise-reduced in-band imaging array, $\underline{Qi}_w$ optionally after having taken the absolute value post-subtraction or applying a floor function in order to eliminate negative values. This process may then be repeated for each additional window for which noise reduction is desired.

In one example implementation, in which adjacent windows overlap, a scaling factor may be applied when subtracting the aligned windowed segment of the in-band noise characterization array $\underline{Ci}_w$ from the in-band imaging array $Qi_w$. For example, the subtraction (and optional modulus) may be calculated according to: $\underline{Qi}_w = Qi_w - \alpha \underline{Ci}_w$, where a is the scaling factor to account for windowing, and where $\alpha=1-\beta$, where $\beta$ is the overlap factor. For example, with $\beta=0.75$, the scaling factor would be $\alpha=0.25$. It will be understood that the present implementation is provided to illustrate an example method of scaling the subtracted component, and that other functional forms may alternatively be employed.

Figure 8C:
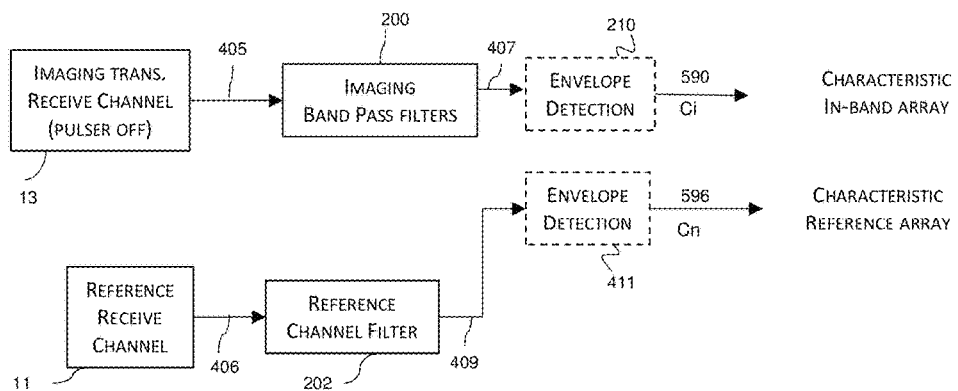
FIGS. 8C and 8D illustrate an example system configuration for noise reduction on an input waveform based noise detected in a filtered reference waveform, in which different time windows of an in-band waveform undergo noise reduction according to the estimated in-band noise that is temporally aligned prior to reduction.
Figure 8D:
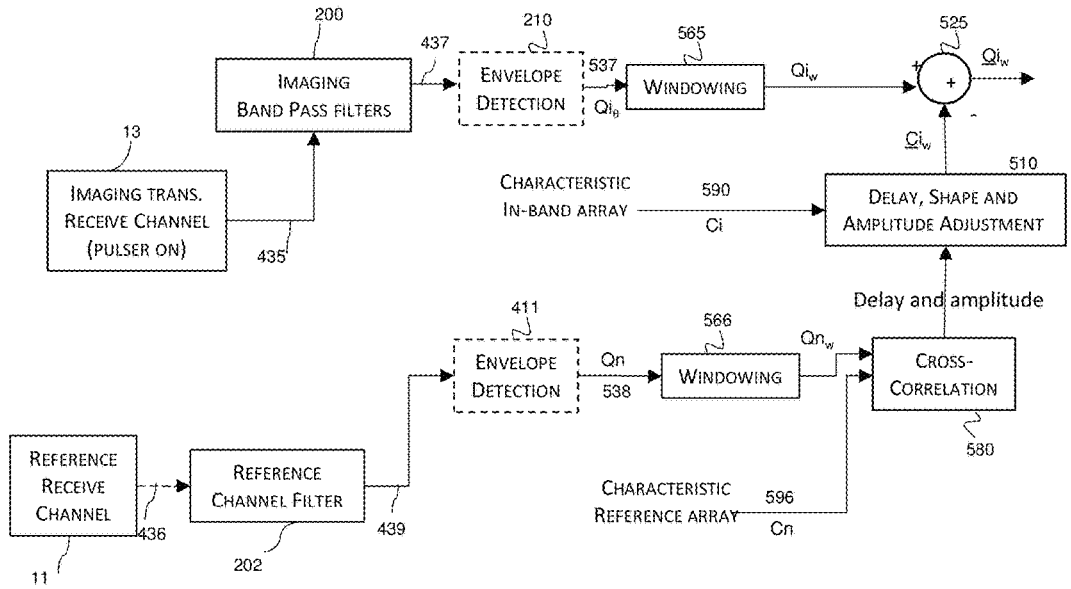

Referring now to FIGS. 8C and 8D, an alternative example embodiment is shown in which a reference receive channel is used when performing noise characterization and for the determination of a suitable amplitude adjustment for noise suppression during imaging. In FIG. 8C, a reference noise characterization waveform 596 is employed, instead of the detection-band noise-characterization waveform 595 of FIG. 8A, when performing noise characterization. Similarly, in FIG. 8D, a filtered reference noise-detection waveform 439 is employed, instead of the detection-band imaging waveform of FIG. 8B, to determine and apply the amplitude adjustment. The methods described above, with reference to FIGS. 8A and 8B, may thus be adapted to the present example embodiment by replacing the detection-band noise characterization waveform 408 with the reference noise-characterization waveform 409 shown in FIG. 8C, and replacing the detection-band imaging waveform 438 (and associated arrays) with the reference noise-detection waveform 439 shown in FIG. 8D.

Embodiment 7: Noise Reduction Using a Plurality of Scans by Changing Scan Rate

The system may be configured such that a set of two or more in-band imaging arrays associated with imaging energy from the same scan line or with scan lines with substantial spatial overlap are obtained. The imaging energy within the set of in-band imaging arrays will have redundant temporal/depth dependency. Averaging (or performing some other statistical processing, such as evaluating the minimum value) the set of redundant in-band imaging arrays may suppress noise if the noise itself is not time-locked to the trigger that prompts the imaging transducer receive circuit to start receiving imaging energy for each scan line. For example, if the pulse repetition frequency of the voltage pulse that excites an imaging ultrasound transducer is 200 us, a periodic noise that repeats every 2 us and will always have a component at 0 us, 2 us, 4 us and so forth for each in-band imaging array. However, if the pulse repetition frequency is adjusted to 199 us, a first imaging array will have noise components at 0 us, 2 us, 4 us and so forth, and a second imaging array will have noise components at 1 us, 3 us, 5 us and so forth. Noise may be suppressed by averaging two successive redundant in-band imaging arrays, optionally after performing envelope detection.

In this example embodiment, noise in a detection-band waveform (out-of-band) may be used to determine the period of one or more in-band noise sources. The system may be prompted to adjust its scan rate so that imaging scan period is not an integer multiple of the period of a noise source. For example, an auto-correlation function may be used to detect periodicity in a detection-band imaging waveform while an imaging transducer receive circuit is receiving imaging energy. Alternatively, the period of one or more noise sources may be determined from a detection-band noise-characterization waveform or reference noise-characterization waveform in a noise characterization stage when the imaging transducer is not receiving imaging energy, or may be loaded from a pre-stored database. The system may then be prompted to adjust its scan rate so that imaging scan period is not an integer multiple of the period of a noise source.

Once the optimal scan rate is determined and the scan rate is adjusted, in-band imaging waveforms obtained from a plurality of scan lines are sampled after performing envelope detection to obtain a set of in-band imaging arrays. An in-band imaging array is denoted as $Qi_\theta$, where $\theta$ is a scan line. A sample from an in-band imaging array is denoted as $Qi_\theta[k]$, where $k=1 \ldots K$ is the sample index and K is the number of samples in the array. The system may be configured to suppress noise by averaging (or performing another statistical measurement, such as taking the minimum) across a plurality of arrays associated with adjacent scan lines or scan lines with significant spatial overlap. For example, if the system is configured to group 3 in-band imaging arrays, a sample $Qi_\theta[k]$ may be replaced by the average of $[Qi_{\theta-1}[k], Qi_\theta[k], Qi_{\theta+1}[k]]$. Optionally, a sample $Qi_\theta[k]$ may be selectively retained after performing some other numerical analysis on the set $[Qi_{\theta-1}[k], Qi_\theta[k], Qi_{\theta+1}[k]]$ and determining whether the sample warrants noise reduction. For example, if for $[Qi_{\theta-1}[k], Qi_\theta[k], Qi_{\theta+1}[k]]$ the minimum value is greater than half the maximum value, the range of sample values may not be large enough to warrant noise reduction by averaging and that the sample is therefore left unchanged.

Such a scheme may also be useful in MRI imaging in the presence of a periodic noise source, by ensuring that RF excitation pulses are initiated at times that do not correlate with the timing or periodicity of noise sources in the local environment.

Additional Feature: Selectively Choosing Samples to Undergo Noise Reduction when Using a Plurality of Scans In the present example embodiment, the scan rate is adjusted as described above, and noise reduction is performed by selectively replacing portions of an in-band imaging array based on statistical measurements (such as average or minimum) from arrays from a plurality of adjacent scan lines, where there is sufficient overlap in the scan region associated with the adjacent scan lines. Only segments of the in-band imaging array that are assessed as noisy using detection-band measurements are replaced.

Figure 8E:
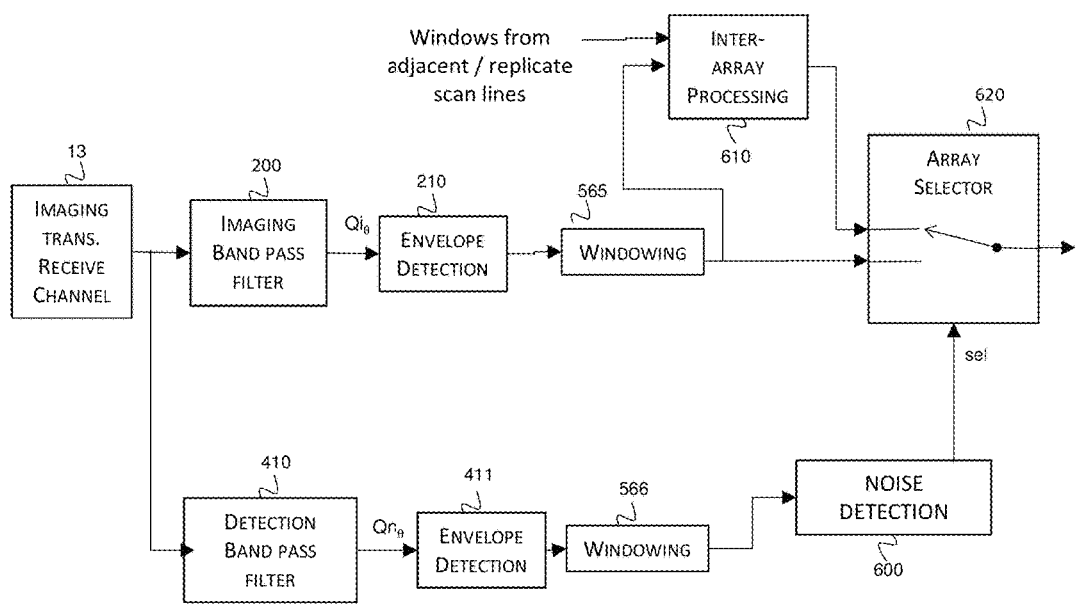
FIG. 8E shows an example system configuration for noise reduction on an input waveform based on noise detected in an out-of-band waveform, in which measures from adjacent or replicate scan lines are employed when performing noise correction.

As shown in FIG. 8E, input waveforms, filtered as shown at 200 and 410 to provide in-band waveforms and detection-band-waveforms may be sampled after performing envelope detection to obtain in-band imaging arrays and detection-band imaging arrays.

Data corresponding to a plurality of scan lines is recorded as sets of arrays for each scan line. A set of arrays are obtained for each scan line, where one in-band imaging array is obtained in an imaging band for each scan line, and at least one out-of-band imaging array is obtained for each scan line. The in-band and detection-band imaging arrays in a pair are denoted as $Qi_\theta$ and $Qn_\theta$, respectively, where $\theta$ is a scan line. A sample from the in-band imaging array and detection-band imaging array is denoted as $Qi_\theta[k]$ and $Qn_\theta[k]$, respectively where $k=1 \ldots K$ is the sample index and K is the number of samples in the array.

The detection-band imaging arrays are segmented into a plurality of windows, each containing J samples of $Qn_\theta$. An array segmented according to windows is denoted as $Qn_{\theta,w}$, where the subscript w is an integer denoting the window number, $\theta$ is an index denoting the scan line, and $Qn_{\theta,w}$ contains samples $[Qn_\theta[k_w], Qn_\theta[k_w+1], \ldots Qn_\theta[k_w+J-1]]$, where $k_w$ is an index of the first sample in the window.

Each window $Qn_{\theta,w}$ in the detection band is assessed for the presence of or absence of noise, as shown at 600. If noise (determined, for example, by measurements of waveform energy such as peak, RMS, etc.) exceeds a threshold, the window is deemed noisy. The threshold may be selected in a noise characterization stage.

According to the present example embodiment, for each detection-band array window $Qn_{\theta,w}$ classified as being noisy, all the co-incidental in-band samples (i.e. $Qi_\theta[k_w]$, $Qi_\theta[k_{w+1}], \ldots Qi_\theta[k_{w+J-1}]$) may be identified as samples that are suitable for noise reduction.

When windows overlap, a given sample $Qi_\theta[k]$ may be associated with more than one window. There may be instances when the sample is associated with both noisy and noise-free windows. In these cases, the system may be configured to pool noise assessments from multiple out-of-band windows before determining if the sample is suitable for noise reduction.

Samples deemed suitable for noise reduction may be replaced at 620 using statistical measures (such as duplicate values, average, minimum, and the like) from samples from arrays associated with adjacent scan lines, computed as shown at 610. For example, if sample $Qi_\theta[k]$ is deemed suitable for noise reduction, and the system is configured to group arrays from 3 scan lines, sample $Qi_\theta[k]$ may be replaced by the minimum of $[Qi_{\theta-1}[k], Qi_\theta[k], Qi_{\theta+1}[k]]$.

Figure 8F:
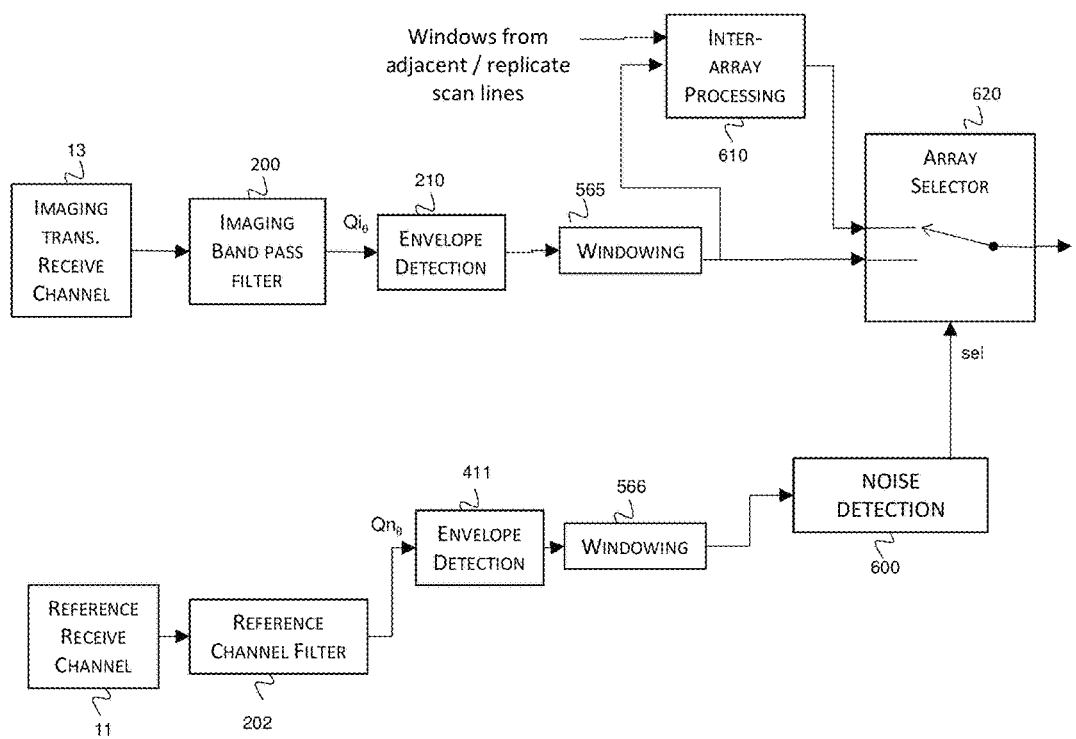
FIG. 8F shows an example system configuration for noise reduction on an input waveform based on noise detected in a filtered reference waveform, in which measures from adjacent or replicate scan lines are employed when performing noise correction.

Referring now to FIG. 8F, an alternative example embodiment is shown in which a reference waveform employed, instead of the detection-band imaging waveform of FIG. 8E, when performing noise reduction during imaging. The methods described above, with reference to FIG. 8D, may thus be adapted to the present example embodiment by replacing the detection-band imaging waveform (and associated arrays) with the filtered reference noise-detection waveform.

Time-Domain Vs. Frequency Domain Processing

The preceding example embodiments have been disclosed within the context of time-domain processing. However, many of the example embodiments disclosed herein may employ frequency-domain or time-frequency domain processing during one or more steps. For example, in FIGS. 6A and 6C, in steps 570 and 572, instead of using maximum power and ratio of maximum power in the imaging band and noise-detection band, short-term Fourier Transform or wavelet transforms can be performed on the in-band waveform and the out-of-band waveform on a per window or per array basis. Analysis of the transform coefficients (e.g. average, mean square, and the like) can then be used to characterize noise or detect windows when noise is present or absent. When noise is detected, instead of attenuating the signal in the time domain in 526, the transform coefficients for the current window can be attenuated. Then, an inverse transform can be performed on the attenuated frequency-domain signal to obtain a noise reduced time-domain signal.

In FIG. 2A (step 510), FIGS. 8B and 8D (step 580), or any other embodiment where cross-correlation between two time-series waveforms is required, Fourier transform algorithms may be used for efficient computation of cross-correlation.

Furthermore, as explained above with reference to FIGS. 7A-7D, machine learning algorithms may be used to classify noise patterns in step 570. These patterns may be defined by frequency domain and/or time-frequency domain features, which will require frequency domain or time-frequency domain processing of time-series waveforms.

Generalization Beyond Ultrasound

Although the preceding example systems and methods for image noise reduction have been illustrated within the context of ultrasound imaging, it will be understood that the embodiments disclosed herein may be adapted to a wide variety of imaging devices, systems and methods.

Figure 9:
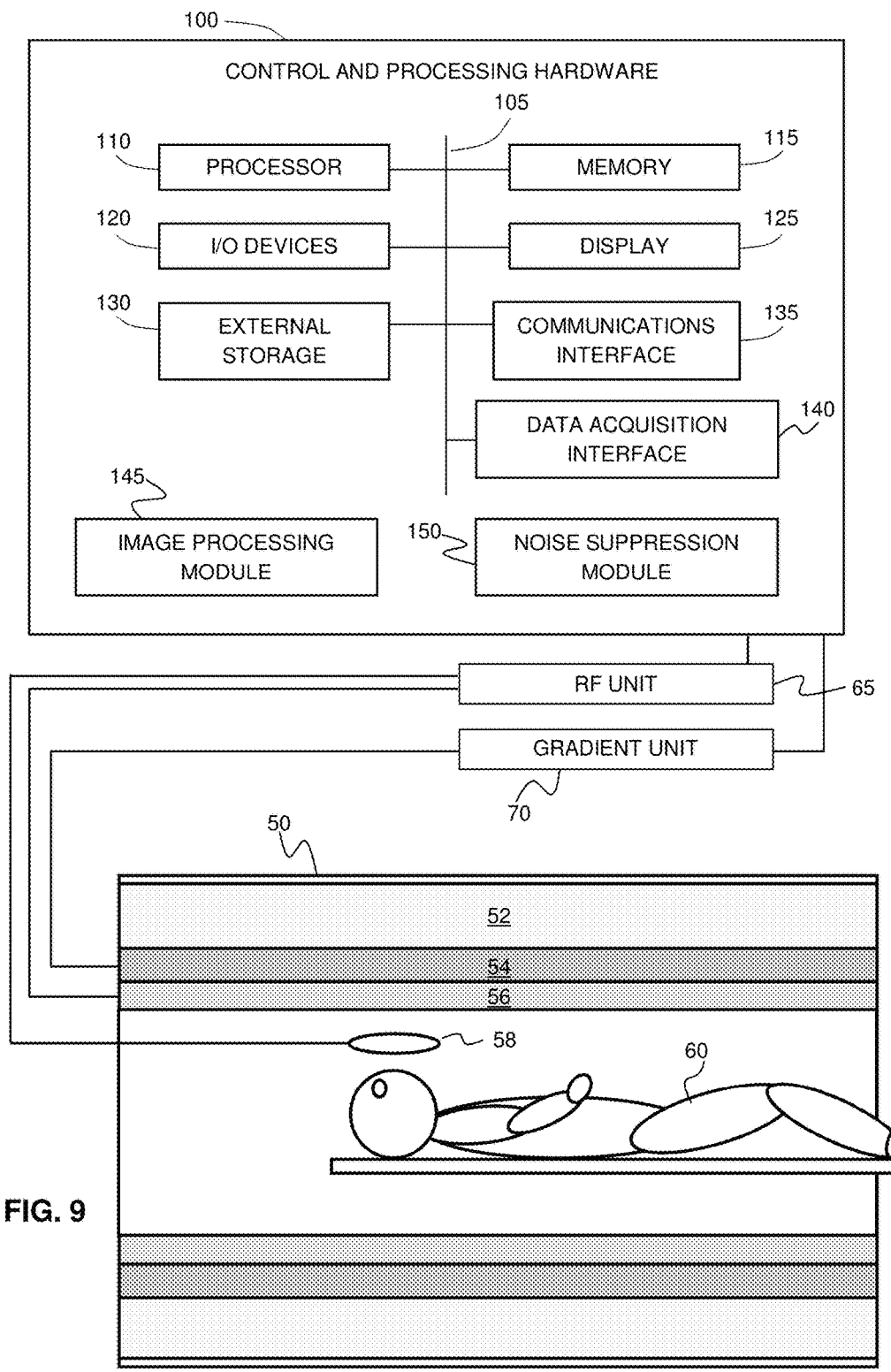
FIG. 9 shows an example of a magnetic resonance imaging system configured for noise suppression.

Another example of an imaging system that may be adapted for noise reduction according to the aforementioned embodiments is a magnetic resonance imaging system. Referring now to FIG. 9, an alternative example system is illustrated in which the signals that undergo noise reduction are obtained from a magnetic resonance (MR) system. The example system includes a magnetic resonance scanner 50 that employs a main magnet 52 to produce a main magnetic field B0, which generates a polarization in a patient 60 or the examined subject. The example system includes gradient coils 54 for generating magnetic field gradients. A reception coil 58 detects the MR signals from patient 60. The reception coil 58 can also be used as a transmission coil. Alternatively, body coil 56 may be employed to radiate and/or detect radio frequency (RF) pulses. The RF pulses are generated by an RF unit 65, and the magnetic field gradients are generated by a gradient unit 70. The manner by which MR signals are detected using the sequence of RF pulses and magnetic field gradients, and how MR images are reconstructed in general, are known to those skilled in the art.

A reference receive circuit may comprise a coil that is in the same room as the scanner, but is not located immediately adjacent to the imaged sample (such as a patient) from which the sought-after MRI signals are emitting. Electromagnetic noise that is traveling near the MRI machine will be detected by both the imaging reception coil 58 and the reference receive circuit. The coil of a reference receive circuit might be oriented and positioned such that it is likely to receive some of the same noise as the imaging reception coil, but be distant enough from the imaged sample such that there is negligible imaging energy detected by the reference receive circuit.

The reference receive circuit coil may be tuned to have the same bandwidth as the imaging reception coil 58, or it may have a different bandwidth that is still able to collect noise signals in the environment that are correlated with noise that might be coupled into the imaging reception coil.

The reference receive circuit may further comprise a collection of receive coils, such as 3 coils whose alignments are orthogonal to each other. This would allow the collection of electromagnetic noise in a manner that a weighted sum of the noise collected in each of the 3 coils might more closely match the noise collected in the imaging reception coil, thus taking into account the directionality of dominant sources of electromagnetic noise in the MRI environment.

It will be understood that the MR system can have additional units or components that are not shown for clarity, such as, but not limited to, additional control or input devices, and additional sensing devices, such as devices for cardiac and/or respiratory gating. Furthermore, the various units can be realized other than in the depicted separation of the individual units. It is possible that the different components are assembled into units or that different units are combined with one another. Various units (depicted as functional units) can be designed as hardware, software or a combination of hardware and software.

In the example system shown in FIG. 9, control and processing hardware 100 obtains magnetic resonance images of patient 60 according to a suitable pulse sequence. Control and processing hardware 100 is interfaced with magnetic resonance imaging scanner 50 for receiving acquired images and for controlling the acquisition of images. Control and processing hardware 100 receives image data from RF unit 65 and processes the imaging data according to the methods described below.

Control and processing hardware 100 may be programmed with a set of instructions which when executed in the processor causes the system to perform one or more methods described in the disclosure in order to reduce noise in signals obtained from the magnetic resonance imaging system. For example, as shown in FIG. 9, control and processing hardware 100 may be programmed with instructions in the form of a set of executable image processing modules, such as, but not limited to, a pulse sequence generation module (not shown), an image acquisition module (not shown), an image processing module 145, and a noise suppression module 150. The pulse sequence generation, image acquisition and image processing modules may be implemented using algorithms known to those skilled in the art for pulse sequence generation, image acquisition, and image reconstruction, respectively. RF data is received from RF coils 56 and/or 58, and optionally one or more reference receive circuits. Data may be sampled and filtered to obtain an in-band waveform. In addition, either a reference waveform via a reference receive circuit or a noise-detection-band waveform measured via filtering of RF from coils 56 and/or 58 are collected. One or more noise suppression methods described in FIGS. 2-8 may be employed for noise suppression at 100. The pulse generation module establishes the sequence of RF pulses and magnetic field gradients depending on the desired imaging sequence, and the image acquisition module stores the MR signals detected by the coils 56 and/or 58 in raw data space. The image processing module 145 processes the acquired optionally noise-suppressed RF data to perform image reconstruction of an MR image.

By being able to detect noise that is correlated to noise in the bandwidth of the imaging signal (either via a reference receive channel or a noise-detection band) the ability to estimate in-band noise and improve the imaging signal by removing the estimated noise from the imaging signal is provided.

This would allow for either an improved SNR in a typical cage for shielding the MRI from environmental noise, or for operation of the MRI system in a more open/unshielded environment that is typically more subject to noise.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Noise Reduction of Unknown Noise Source Via Attenuation Factor (Example of Embodiment 5)

The present example involved the collection of ultrasound data using an intra-cardiac echo (ICE) system, in the presence of two noise sources. The transducer was configured to detect ultrasound energy at frequency of 9 MHz. Two band pass filters were used in parallel to separate the radio-frequency (RF) signal into an imaging band of 7-13 MHz, and a noise-detection band of 15-25 MHz which is beyond the frequency range of the emitted ultrasound.

The first noise source was an electroanatomic mapping system (Carto® 3). The system has an electromagnetic tracking module and an impedance-based tracking module, for which patches to measure impedance and estimate device position are attached to a patient. These patches can couple a significant amount of noise into the imaging band of the ICE images. In the present experiments, a heart phantom was used in a saline bath. The electrodes from the impedance patches were submerged in the bath. The second noise source was from powering on an ablation generator that was connected to the Carto® 3 console. The noise generated from this second noise source was determined to likely be noise propagating from the ablation generator, through the Carto® 3 console and through the patch electrodes into the saline bath when the generator was powered on.

FIG. 10A shows an ultrasound image collected in the absence of either noise source, while FIGS. 10B and 10C show the effect of the first and second noise sources, respectively, on the imaging quality.

Noise reduction of ultrasound waveforms detected by the ultrasound transducer of the ICE console was performed according to an implementation of the method illustrated in FIGS. 6A and 6D.

During a first baseline noise characterization stage of the present experiment, energy was detected within an imaging band and in the absence of receiving imaging energy and in the absence of receiving noise energy, thereby obtaining an in-band baseline noise characterization array, denoted as Gi. The in-band baseline noise characterization array was obtained from sampling an in-band waveform for 125 us at 200 MS/s. A sliding and overlapping window (window size=64 samples, 20% overlap) was employed, and in-band power measures were calculated for each window. A representative maximum power (90th percentile across all windows) was calculated, and its value was assigned to threshold Ti.

During a second noise characterization stage of the present experiment, energy was detected within both the imaging band and the noise-detection-band in the absence of the receiving of imaging energy (i.e. when the transducer was not being pulsed with a voltage, and was d hence not receiving ultrasound energy), thereby obtaining correlated measurements of in-band noise and noise-detection-band noise, denoted as Ci and Cn. The noise-detection band was configured as the frequency band spanning approximately 15 to 25 MHz.

In the present example implementation involving an ICE system, 512 waveforms (each 125 us in duration sampled at 200 MS/s) were obtained. Accordingly, 512 in-band and detection-band noise-characterization waveform pairs were employed to estimate noise characteristics. A sliding and overlapping window (window size=64, 20% overlap) was employed for both the imaging band and the noise-detection band to obtain windowed pairs of in-band and detection-band noise characterization arrays, denoted as $Ci_w$ and $Cn_w$, where the subscript w is an integer denoting the window number. For each pair of $Ci_w$ and $Cn_w$, the power in the imaging band and the power in the noise-detection-band were calculated. Only windows whose in-band power was greater than threshold Ti were selected for further noise characterization.

Statistical noise power measurements were calculated during noise characterization. A set of windows of the in-band noise characterization array whose power falls between the $96^{th}$ and $99^{th}$ percentiles of in-band noise-characterization array power values was selected. Within this set, the window with the near-minimum noise-detection band power ($20^{th}$ percentile within the set) was chosen as w_max, and power values $P(Cn_{w\_max})$ and $P(Ci_{w\_max})$ were calculated and denoted as $Pn_{max}$ and $Pi_{max}$, respectively. Similarly, a set of windows of the in-band noise characterization array whose in-band power falls between the $1^{st}$ and $5^{th}$ percentiles of in-band noise-characterization array power values was selected. Within this set, the window with the near-minimum noise-detection band power ($20^{th}$ percentile within the set) was chosen as w_min, and power values P($Cn_{w\_min}$) and P($Ci_{w\_min}$) were calculated and denoted as $Pn_{min}$ and $Pi_{min}$, respectively.

As shown in FIG. 6B, a slope m, and y-intercept c, of the line passing through the points ($Pn_{max}$, $Pi_{max}$) and ($Pn_{min}$, $Pi_{min}$). A relaxation parameter β was set as unity. A function f was defined as:

$$f(Pn) = \begin{cases} 0, & Pn < Pn_{min} \\ (\beta.m.Pn) + c, & Pn_{min} \le Pn \le Pn_{max} \\ Pi_{max}, & Pn > Pn_{max} \end{cases}$$

wherein $Pn_w$ is the power in the detection band. It will be understood that the present implementation is provided to illustrate an example algorithm for selecting a functional relationship between the relative powers in the imaging and detection bands, and that other functional forms may alternatively be employed.

The function f( ) was employed to perform noise reduction of in-band imaging waveforms obtained during imaging (i.e. when the pulser was periodically emitting imaging energy, and ultrasound energy was being received by the transducer receive circuit).

Waveforms in the imaging band and the noise-detection band were sampled to obtain pairs of in-band imaging arrays and detection-band imaging arrays, denoted as $Qi_\theta$ and $Qn_\theta$. θ is an index identifying a period of acquisition corresponding to a scan line. The imaging arrays were temporally segmented according to the windows, denoted as $Qi_{\theta,w}$ and $Qn_{\theta,w}$, where the subscript w is an integer denoting the window number. For each windowed portion of the in-band imaging array and the out-of-band imaging array, powers P($Qi_{\theta,w}$) and P($Qn_{\theta,w}$), were calculated, and denoted as $Pi_{\theta,w}$ and $Pn_{\theta,w}$ respectively.

For each window, out-of-band imaging power $Pn_{\theta,w}$ was used to estimate a noise energy, $\hat{Pi}_{N\theta,w}$, within the in-band imaging window $Qi_{\theta,w}$. $\hat{Pi}_{N\theta,w}$ was calculated as $f(Pn_{\theta,w})$, where β was set to unity and parameters m, c, $Pn_{max}$ and $Pn_{min}$, were obtained in the noise characterization stage. $\hat{Pi}_{N\theta,w}$ was clamped below $Pi_{\theta,w}$. An attenuating factor was calculated as $[Pi_{\theta,w} - \hat{Pi}_{N\theta,w}]/Pi_{\theta,w}$. The attenuating factor was clamped above 0.02. The attenuating factor was multiplied with the array $Qi_{\theta,w}$ to obtain a noise reduced array $\underline{Qi}_{\theta,w}$. $\underline{Qi}_\theta$ for all 512 scan lines were enveloped and processed by an image generator (step 230).

The aforementioned algorithm was employed to reduce noise in the in-band imaging waveforms when performing imaging in the presence of the first noise and second noise sources. FIGS. 11A and 11B show the images obtained in the presence of the first noise source, without (A) and with (B) the application of the present noise reduction algorithm. FIGS. 12A and 12B show the images obtained in the presence of the second noise source, without (A) and with (B) the application of the present noise reduction algorithm. A clear improvement in the signal-to-noise ratio (approximately 6 dB improvement) was observed in both cases. As a further illustration, FIGS. 11C, 11D, and 11E show the images obtained in the presence of the first noise source with the application of the present noise reduction method when the relaxation parameter β of function f( ) was set as 0.5 (C), unity (D) and 1.5 (E).

Example 2: Noise Reduction of Periodic Noise Source with Delay Correction (Embodiment 6)

Figure 13A:
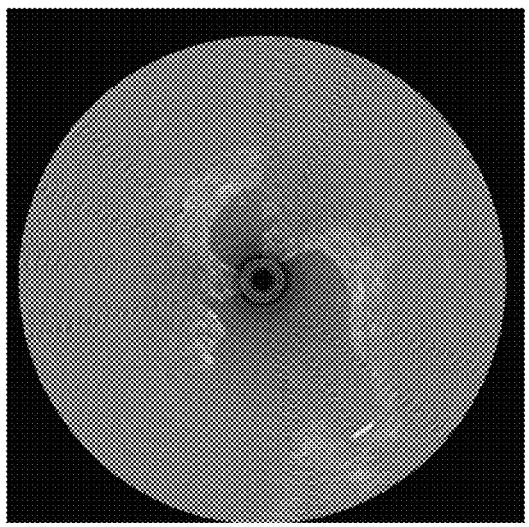
FIGS. 13A-B show the images in obtained in the presence of noise from a magnetic tracking system, without (A) and with (B) the application of a noise reduction method.

In the present example, noise reduction of ultrasound waveforms detected by the ultrasound transducer of the ICE console was performed according to an implementation of the method illustrated in FIGS. 8A and 8B. The data for this example was collected with an ICE console with the presence of an electromagnetic tracker. The control unit of the electromagnetic tracker was observed to generate a pseudo-periodic noise pattern in the ultrasound image data, as shown in FIG. 13A.

In the present example implementation involving an ICE system, one waveform (125 us in length sampled at 200 MS/s) was obtained when collecting data in raw/RF mode while the imaging transducer is not receiving imaging energy.

Data was saved as a pair of arrays (i.e. sampled waveforms), the first array consisting of an in-band noise-characterization waveform (7-13 MHz) sampled after having performed envelope detection, and a corresponding array consisting of an out-of-band noise-characterization waveform in the 15-25 MHzband sampled after having performed envelope detection. These in-band and detection band noise-characterization arrays are denoted as Ci and Cn, respectively.

The correlated in-band noise and out-of-band noise was then used to perform noise reduction of the in-band imaging waveform during the acquisition of imaging data i.e. while the ultrasound transducer is receiving ultrasound energy.

While imaging, a pair of arrays were obtained for several periods of acquisition corresponding, each period corresponding to a scan line, θ. For each array pair, one array was obtained in the imaging band (7-13 MHZ), and one array was obtained in the noise-detection-band (15-25 MHz). Each array was 125 us in length sampled at 200 MS/s. The arrays, referred to as the in-band imaging and out-of-band imaging arrays, and denoted as $Qi_\theta$ and $Qn_\theta$, respectively, were measured during imaging, i.e. while the transducer was receiving imaging energy.

Each in-band imaging array was processed for noise reduction using the in-band noise characterization array to reduce noise from the in-band imaging array.

The in-band and out-of-band imaging arrays $Qi_\theta$ and $Qn_\theta$ were segmented into a plurality of time windows. In the present example implementation, the window size was 800 samples (in this case 4 μs at a rate of 200 MS/s), with a 75% overlap between adjacent windows. The imaging arrays, temporally segmented according to the windows, are denoted as $Qi_{\theta,w}$ and $Qn_{\theta,w}$, where the subscript w is an integer denoting the window number.

Temporal alignment between $Qn_{\theta,w}$ and Cn was achieved on a per-window basis. The temporal alignment was achieved by calculating, the cross-correlation between the out-of-band noise characterization array Cn and the out-of-band imaging array $Qn_{\theta,w}$, and selecting the relative time delay τ corresponding to the maximum cross-correlation. Due to the correlation between the in-band noise and the out-of-band noise, this time delay τ was also applied to align the in-band noise characterization array relative to the windowed in-band imaging array. The aligned in-band noise characterization array is then windowed (denoted by $\underline{Ci}_w$).

A scaling factor was applied to the in-band noise characterization array $\underline{Ci}_w$ before it was subtracted from the in-band imaging array $Qi_{\theta,w}$. A noise reduced in-band imaging array, $\underline{Qi}_{\theta,w}$, was calculated according to $\underline{Qi}_{\theta,w} = Qi_{\theta,w} - \alpha \underline{Ci}_w$, where $\alpha = 0.25$ was the scaling factor to account for windowing. Negative values were replaced with 0.

This process was repeated for each additional window, for each scan line.

Figure 13B:
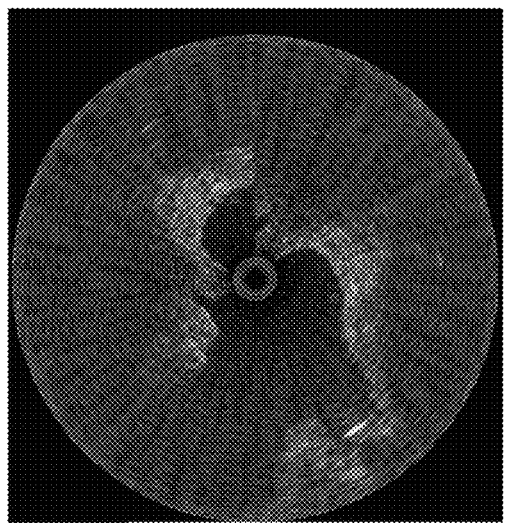

The aforementioned method was employed to reduce noise of the data obtained when performing imaging in the presence of an Aurora™ electromagnetic tracking system (Northern Digital Inc), which acted as a noise source. FIGS. 13A and 13B show the images in obtained in the presence of the noise source, without (A) and with (B) the application of the present noise reduction method. A clear improvement in the signal-to-noise ratio (approximately 5 dB) was observed when the noise reduction method was implemented.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of denoising imaging signals detected in the presence of broadband noise, the method comprising:
   in the absence of receiving imaging energy, detecting energy waves with an imaging transducer receive circuit, thereby obtaining a noise characterization waveform, and filtering the noise characterization waveform to generate an in-band noise characterization waveform residing within an imaging band and an out-of-band noise characterization waveform residing within a noise-detection band that lies, at least in part, beyond the imaging band;
   segmenting the in-band noise characterization waveform and the out-of-band noise characterization waveform according to one or more time windows;
   for at least one time window, processing the in-band noise characterization waveform and the out-of-band noise characterization waveform to determine a relationship between noise in the imaging band and noise in the noise-detection band;
   detecting imaging signals with the imaging transducer receive circuit thereby obtaining one or more imaging waveforms;
   for at least one imaging waveform:
   a) filtering the imaging waveform to generate an in-band imaging waveform residing within the imaging band and an out-of-band noise-detection imaging waveform residing within the noise-detection band;
   b) segmenting the in-band imaging waveform and the out-of-band noise-detection imaging waveform according to one or more time windows;
   c) employing the relationship and the out-of-band noise-detection imaging waveform to estimate, within at least one time window, a measure associated with the amount of noise in the in-band imaging waveform; and
   d) for at least one time window processed in c), applying a denoising correction to the portion of the in-band imaging waveform within the time window.

2. The method according to claim 1 wherein the step of detecting imaging signals comprises detecting imaging signals with the imaging transducer receive circuit along a plurality of scan lines, the method further comprising:
   obtaining a plurality of imaging waveforms respectively associated with the plurality of scan lines; and
   generating an image based on denoised in-band imaging waveforms respectively associated with the plurality of scan lines.

3. The method according to claim 1 wherein step d) is performed when the measure is greater than a threshold.

4. The method according to claim 1 wherein the relationship between noise in the imaging band and noise in the noise-detection band is associated with a measure of relative energy in the in-band noise characterization waveform and the out-of-band noise characterization waveform.

5. The method according to claim 4 wherein two or more time windows are processed to determine the relationship between noise in the imaging band and noise in the noise-detection band.

6. The method according to claim 1 wherein the measure associated with the amount of noise in the in-band imaging waveform is based on the relationship and the amount of power of the in-band noise characterization waveform.

7. The method according to claim 1 wherein the denoising correction comprises a subtrahend value.

8. The method according to claim 7 wherein the subtrahend value associated with a given time window increases with the amount of energy detected within the out-of-band noise-detection imaging waveform for the given time window.

9. The method according to claim 1 wherein the denoising correction comprises of multiplication with an attenuation factor.

10. The method according to claim 9 wherein the attenuation factor associated with a given time window is decreases with the measure associated with the amount of noise in the in-band imaging waveform for the given time window, thereby attenuating portions of the in-band imaging waveform associated with noise.

11. The method according to claim 3 wherein, prior to applying the denoising corrections, each time window having a measure exceeding the threshold is reassessed relative to spatially adjacent time windows corresponding to spatially adjacent scan lines, such that samples corresponding to a given time window that are initially estimated to be associated with the presence of noise are replaced with samples from spatial adjacent time windows in the event that the adjacent time windows are estimated to be associated with the absence of noise.

12. The method according to claim 3 wherein, prior to applying the denoising corrections, each time window having a measure exceeding the threshold is reassessed relative to temporally adjacent time windows, such that a given time window that is initially estimated to be associated with the absence of noise is reassessed as being associated with the presence of noise in the event that the adjacent time windows are estimated to be associated with the presence of noise.

13. The method according to claim 1 wherein the denoising correction applied for a given time window is dependent on the depth of the given time window within the in-band imaging waveform.

14. The method according to claim 3 wherein the threshold is determined based on baseline measurements made in the absence of imaging energy and noise.

15. The method according to claim 1 further comprising repeating noise characterization to re-establish the relationship between noise in the imaging band and noise in the noise-detection band.

16. The method according to claim 15 wherein the noise characterization is repeated according to user input.

17. The method according to claim 15 wherein the noise characterization is repeated automatically when the absence of imaging energy is detected.

18. The method according to claim 1 further comprising monitoring one or more parameters associated with the out-of-band noise-detection imaging waveform in order to detect changes in the noise within the noise-detection band.

19. The method according to claim 18 further comprising generating an alert or message when a change at least one parameter has been detected.

20. The method according to claim 1 further comprising:
    performing noise suppression on the in-band imaging waveform during the absence of imaging energy;
    generating an error value based on the energy in the in-band imaging waveform after noise correction; and
    generating an alert for repeating the noise characterization when the error value exceeds a pre-selected threshold.

21. The method according to claim 1 wherein the imaging transducer receive circuit comprises an ultrasound transducer.

22. The method according to claim 1 wherein the imaging transducer receive circuit comprises a coil for detecting a magnetic field.

* * * * *